(12) United States Patent
Sheiko et al.

(10) Patent No.: US 11,970,560 B2
(45) Date of Patent: Apr. 30, 2024

(54) SELF-ASSEMBLED ELASTOMERS WITH MOLECULARLY ENCODED TISSUE-LIKE SOFTNESS, STRAIN-ADAPTIVE STIFFENING AND COLORATION

(71) Applicant: The University of North Carolina at Chapel Hill, Chapel Hill, NC (US)

(72) Inventors: Sergei Sheiko, Chapel Hill, NC (US); Mohammad Vatankhah-Varnosfaderani, Coatesville, PA (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 633 days.

(21) Appl. No.: 16/643,736

(22) PCT Filed: Sep. 3, 2018

(86) PCT No.: PCT/US2018/049300
§ 371 (c)(1),
(2) Date: Mar. 2, 2020

(87) PCT Pub. No.: WO2019/046840
PCT Pub. Date: Mar. 7, 2019

(65) Prior Publication Data
US 2020/0399414 A1    Dec. 24, 2020

Related U.S. Application Data

(60) Provisional application No. 62/634,843, filed on Feb. 24, 2018, provisional application No. 62/585,124, filed on Nov. 13, 2017, provisional application No. 62/553,870, filed on Sep. 3, 2017.

(51) Int. Cl.
| | | |
|---|---|---|
| C09D 153/00 | (2006.01) | |
| A61L 27/16 | (2006.01) | |
| C08F 293/00 | (2006.01) | |
| C09J 153/00 | (2006.01) | |

(52) U.S. Cl.
CPC .......... *C08F 293/005* (2013.01); *A61L 27/16* (2013.01); *C09D 153/00* (2013.01); *C09J 153/00* (2013.01); *C08F 2438/01* (2013.01)

(58) Field of Classification Search
CPC ............. C08F 293/005; C08F 2438/01; C09D 153/00; C09J 153/00; A61L 27/16
USPC ........................................................ 524/838
See application file for complete search history.

(56) References Cited

U.S. PATENT DOCUMENTS

| 5,506,320 A | 4/1996 | Yu |
| 2004/0110893 A1 | 6/2004 | Matyjaszewski et al. |
| 2006/0018872 A1 | 1/2006 | Tew et al. |
| 2011/0171712 A1 | 7/2011 | Rivron et al. |
| 2015/0125646 A1 | 5/2015 | Tournilhac et al. |
| 2017/0183629 A1 | 6/2017 | Alsberg et al. |

FOREIGN PATENT DOCUMENTS

| WO | WO-2014/081819 A1 | 5/2014 |
| WO | WO-2017/015614 A1 | 1/2017 |
| WO | WO-2019/046810 A1 | 3/2019 |
| WO | WO-2019/152537 A1 | 8/2019 |

OTHER PUBLICATIONS

Daniel et al. ["Bottlebrush-Guided Polymer Crystallization Resulting in Supersoft and Reversibly Moldable Physical Networks", Macromolecules, Feb. 24, 2017 (Feb. 24, 2017), vol. 50, pp. 2103-2111].*
Froes-Salgado et al ["Influence of the base and diluent monomer on network characteristics and mechanical properties of neat resin and composite materials", Odontology, Apr. 12, 2014(Apr. 12, 2014), vol. 103, pp. 160-168].*
Zhang et al. ["Anti-fouling Coatings of Poly(dimethylsiloxane) Devices for Biological and Biomedical Applications", Journal of Medical and Biological Engineering, Apr. 1, 2015(Apr. 1, 2015), vol. 35, pp. 143-155].*
U.S. Appl. No. 62/634,843, filed Feb. 24, 2018, Sergey Sheiko.
U.S. Appl. No. 62/623,878, filed Jan. 30, 2018, Sergey Sheiko.
U.S. Appl. No. 62/666,318, filed May 3, 2018, Sergei Sheiko.
U.S. Appl. No. 62/910,089, filed Oct. 3, 2019, Sergei Sheiko.
PCT, PCT/US2018/049300 (WO 2019/046810), Sep. 3, 2018 (Mar. 7, 2019), The University of North Carolina at Chapel Hill.
PCT, PCT/US2019/015877 (WO 2019/152537), Jan. 30, 2019 (Aug. 8, 2019), The Universtiy of North Carolina at Chapel Hill.
Balani et al. 'Physical, Thermal, and Mechanical Properties of Polymers', Biosurfaces: A Materials Science and Engineering Perspective, (2014), Chapter AI, pp. 329-344.
Daniel et al. 'Bottlebrush-Guided Polymer Crystallization Resulting in Supersoft and Reversibly Moldable Physical Networks', Macromolecules, (2017), vol. 50, pp. 2103-2111 (Abstract).
Daniel et al. 'Solvent-free, supersoft and superelastic bottlebrush melts and networks', Nature Material, (2015), vol. 15, pp. 183-190.
Froes-Salgado et at Influence of the base and diluent monomer on network characteristics and mechanical properties of neat resin and composite materials, Odontology, (2014), vol. 103, pp. 160-168.
Sokolowski et al. 'Medical applications of shape memory polymers', Biomedical Materials, (2007), vol. 2, pp. S23-S27.
Vatankhah-Varnosfaderani et al. 'Chameleon-like elastomers with molecularly encoded strain-adaptive stiffening and coloration', Science, (2018), vol. 359, pp. 1509-1513.

(Continued)

*Primary Examiner* — Kelechi C Egwim
(74) *Attorney, Agent, or Firm* — Ballard Spahr LLP

(57) ABSTRACT

The invention generally relates to linear-bottlebrush-linear copolymer blocks and methods of making and using same. The disclosed copolymer blocks can be useful in, for example, the formation of polymer networks that replicate biological stress-strain behavior. This abstract is intended as a scanning tool for purposes of searching in the particular art and is not intended to be limiting of the present invention.

16 Claims, 37 Drawing Sheets

(56) References Cited

OTHER PUBLICATIONS

Zhang et al. 'Anti-fouling Coatings of Poly(dimethylsiloxane) Devices for Biological and Biomedical Applications', Journal of Medical and Biological Engineering vol. 35, pp. 143-155(2015).
International Search Report and Written Opinion were mailed on Jan. 31, 2019 by the International Searching Authority for International Application No. PCT/US2018/049300, filed on Sep. 3, 2018 and published as WO 2019/046810 on Mar. 7, 2019 (Applicant—The University of North Carolina at Chapel Hill) (10 Pages).
International Preliminary Report on Patentability was mailed on Mar. 3, 2020 by the International Searching Authority for International Application No. PCT/US2018/049300, filed on Sep. 3, 2018 and published as WO 2019/046810 on Mar. 7, 2019 (Applicant—The University of North Carolina at Chapel Hill) (9 Pages).
International Search Report and Written Opinion were mailed on Apr. 15, 2019 by the International Searching Authority for International Application No. PCT/US2019/015877, filed on Jan. 30, 2019 and published as WO 2019/152537 on Aug. 8, 2019 (Applicant—The University of North Carolina at Chapel Hill) (6 Pages).
Lendlein et al. (2005) "Shape-Memory Polymer Networks from Oligo($\varepsilon$-caprolactone)Dimethacrylates," Journal of Polymer Science: Part A: Polymer Chemistry, 43: 1369-1381.
Nochel et al. (2013) "Shape-memory properties of hydrogels having a poly($\varepsilon$-caprolactone) crosslinker and switching segment in an aqueous environment," European Polymer Journal, 49: 2457-2466.
Xu et al. (2016) "Fluorinated bottlebrush polymers based on poly(trifluoroethyl methacrylate): synthesis and characterization," *Polym. Chem.* 7: 680-688.

\* cited by examiner

| Sample | $n_{sc}^a$ | $n_x^b$ | $n_g^c$ | $E$ (kPa)$^d$ | $\beta^e$ | $E_0$ (kPa)$^f$ | $\lambda_{max}^g$ | $\lambda_{max,ex}^h$ |
|---|---|---|---|---|---|---|---|---|
| Series 1 Bottlebrush | 14 | 400 | 1 | 3.3±0.3 | 0.08±0.01 | 3.7 | 3.5±0.2 | 3.5±0.3 |
|  | 14 | 200 | 1 | 8.4±0.3 | 0.11±0.01 | 9.9 | 3.0±0.2 | 2.9±0.2 |
|  | 14 | 100 | 1 | 18.6±0.6 | 0.17±0.01 | 24.2 | 2.4±0.1 | 2.1±0.2 |
|  | 14 | 67 | 1 | 30.0±1.2 | 0.23±0.01 | 43.7 | 2.1±0.1 | 1.9±0.2 |
|  | 14 | 50 | 1 | 40.5±1.5 | 0.28±0.02 | 65.6 | 1.9±0.1 | 1.5±0.1 |
| Series 2 Bottlebrush | 28 | 400 | 1 | 2.4±0.2 | 0.14±0.04 | 3.0 | 2.7±0.1 | 2.6±0.5 |
|  | 28 | 200 | 1 | 3.8±0.2 | 0.17±0.04 | 4.9 | 2.4±0.1 | 2.5±0.5 |
|  | 28 | 100 | 1 | 8.6±0.3 | 0.31±0.01 | 14.9 | 1.8±0.1 | 1.6±0.2 |
|  | 28 | 50 | 1 | 21.3±1.5 | 0.44±0.02 | 52.4 | 1.5±0.1 | 1.4±0.1 |
| Series 3 Comb | 14 | 300 | 1 | 10.3±0.1 | 0.074±0.003 | 11.4 | 3.7±0.1 | 3.8±0.2 |
|  | 14 | 300 | 2 | 16.5±0.3 | 0.037±0.002 | 17.4 | 5.2±0.1 | 4.2±0.6 |
|  | 14 | 300 | 4 | 36.3±0.4 | 0.035±0.003 | 48.0 | 5.3±0.3 | 4.3±0.5 |
|  | 14 | 300 | 16 | 98.7±2.8 | 0.030±0.002 | 164.0 | 5.8±0.2 | 4.4±0.7 |
|  | 14 | 300 | 32 | 115.5±2.4 | 0.030±0.001 | 206.4 | 5.7±0.1 | 4.6±0.6 |
|  | 14 | 300 | 64 | 124.2±0.4 | 0.027±0.002 | 228.5 | 6.1±0.2 | 5.0±0.5 |

FIG. 22

| | | | | | | | |
|---|---|---|---|---|---|---|---|
| Series 4 Comb | 14 | 600 | 1 | 2.7±0.1 | 0.066±0.004 | 3.0 | 3.9±0.1 | 4.5±0.2 |
| | 14 | 600 | 2 | 7.9±0.2 | 0.032±0.002 | 8.3 | 5.6±0.2 | 5.5±0.4 |
| | 14 | 600 | 4 | 24.6±0.8 | 0.027±0.001 | 26.7 | 6.1±0.1 | 5.5±0.3 |
| | 14 | 600 | 8 | 42.9±2.0 | 0.022±0.001 | 64.3 | 6.8±0.1 | 6.4±0.1 |
| | 14 | 600 | 16 | 60.3±2.1 | 0.017±0.002 | 106.7 | 7.7±0.2 | 6.6±0.5 |
| | 14 | 600 | 32 | 70.8±1.1 | 0.017±0.001 | 138.5 | 7.6±0.1 | 8.0±0.1 |
| | 14 | 600 | 64 | 79.5±1.0 | 0.015±0.004 | 165.1 | 8.2±0.9 | 7.7±0.4 |
| Series 5 Comb | 14 | 1200 | 1 | 1.4±0.2 | 0.039±0.001 | 1.5 | 5.1±0.1 | 5.9±0.1 |
| | 14 | 1200 | 2 | 3.0±0.4 | 0.020±0.002 | 3.1 | 7.1±0.4 | 7.2±0.8 |
| | 14 | 1200 | 4 | 10.7±0.3 | 0.014±0.001 | 15.4 | 8.4±0.3 | 7.8±0.4 |
| | 14 | 1200 | 16 | 32.1±0.7 | 0.012±0.001 | 86.9 | 9.1±0.4 | 11.7±1.0 |
| | 14 | 1200 | 32 | 37.2±0.4 | 0.011±0.001 | 126.6 | 9.5±0.4 | 7.6±0.7 |
| | 14 | 1200 | 64 | 42.7±0.2 | 0.011±0.001 | 155.2 | 9.4±0.4 | 10.7±0.5 |

FIG. 22
(Continued)

| | | | | | | | | |
|---|---|---|---|---|---|---|---|---|
| Series 6 | 14 | 1800-2 | 1 | 2.7±0.1 | 0.39±0.02 | 4.8 | 1.6±0.1 | 2.1±0.1 |
| Plastomer | 14 | 1200-2 | 1 | 4.2±0.1 | 0.26±0.02 | 4.5 | 2.0±0.1 | 3.7±0.3 |
| $\phi_{MMA} = 0.06$ | 14 | 900-2 | 1 | 3.9±0.2 | 0.26±0.01 | 3.9 | 2.0±0.1 | 4.5±0.3 |
| | 14 | 600-2 | 1 | 3.6±0.1 | 0.29±0.03 | 4.1 | 1.9±0.1 | 4.1±0.2 |
| | 14 | 300-2 | 1 | 6.3±0.2 | 0.54±0.03 | 21.6 | 2.6±0.1 | 1.4±0.1 | a-c) Degrees of polymerization of side chains, backbone of the network strand, and spacer between side chains along the backbone, respectively. d,e) Young's modulus (E) and strand extension ratio ($\beta$) obtained by fitting the experimental tensile stress-strain curves using Eq. 1 in the main text. f) Apparent Young's modulus measured as a tangent to the corresponding stress-strain curves at $\lambda \rightarrow 1$. g,h) Expected ($\lambda_{max} \cong \beta^{-0.5}$) and measured elongation-at-break values.

FIG. 22
(Continued)

| Sample | $n_{bb}$ (1) | $n_A$ (2) | $\phi_A$ (3) | $E$ (kPa) (4) | $\beta$ (4) | $\lambda_{fit}$ (5) | $E_0$ (kPa) (6) | $\lambda_{max}$ (7) |
|---|---|---|---|---|---|---|---|---|
| | | | | PMMA-bbPDMS-PMMA | | | | |
| M300-1 | 302 | 57 | 0.03 | 4.5±0.3 | 0.48±0.02 | 1.75 | 12.8 | 2.7 |
| M300-2 | | 117 | 0.06 | 5.5±0.5 | 0.56±0.04 | 1.40 | 20.4 | 2.5 |
| M300-3 | | 181 | 0.09 | 5.6±0.5 | 0.69±0.02 | 1.40 | 41.5 | 2.0 |
| M300-4 | | 369 | 0.17 | 6.6±0.2 | 0.76±0.02 | 1.30 | 77.4 | 1.8 |
| M600-1 | 602 | 295 | 0.07 | 2.9±0.2 | 0.30±0.03 | 2.00 | 4.9 | 3.7 |
| M600-2 | | 351 | 0.09 | 3.6±0.2 | 0.35±0.02 | 1.85 | 6.9 | 3.8 |
| M600-3 | | 677 | 0.16 | 4.4±0.3 | 0.42±0.03 | 1.50 | 10.1 | 3.1 |
| M600-4 | | 803 | 0.18 | 5.0±0.1 | 0.51±0.02 | 1.65 | 15.3 | 2.5 |
| M900-1 | 938 | 190 | 0.03 | 3.3±0.1 | 0.29±0.01 | 1.80 | 5.4 | 3.8 |
| M900-2 | | 325 | 0.05 | 3.6±0.1 | 0.33±0.01 | 1.75 | 6.5 | 4.4 |
| M900-3 | | 656 | 0.10 | 4.7±0.1 | 0.45±0.01 | 1.70 | 11.8 | 3.3 |
| M900-4 | | 1235 | 0.18 | 6.2±0.3 | 0.67±0.02 | 1.55 | 39.3 | 2.1 |

FIG. 23

| Sample | | | | | | | | |
|---|---|---|---|---|---|---|---|---|
| M1200-1 | 1065 | 360 | 0.05 | 3.3±0.2 | 0.26±0.02 | 2.40 | 5.1 | 4.5 |
| M1200-2 | | 480 | 0.06 | 3.8±0.1 | 0.30±0.01 | 1.95 | 6.4 | 3.7 |
| M1200-3 | | 810 | 0.10 | 3.9±0.2 | 0.36±0.02 | 1.85 | 7.8 | 3.2 |
| M1200-4 | | 930 | 0.11 | 4.1±0.3 | 0.40±0.03 | 2.10 | 9.0 | 2.9 |
| M1500-3 | 1483 | 867 | 0.09 | 2.1±0.1 | 0.33±0.02 | 2.00 | 3.7 | 3.1 |
| M1800-1 | | 365 | 0.03 | 1.5±0.2 | 0.40±0.02 | 1.75 | 3.4 | 2.8 |
| M1800-2 | 1765 | 545 | 0.05 | 1.8±0.2 | 0.48±0.04 | 1.55 | 5.0 | 2.4 |
| M1800-3 | | 780 | 0.07 | 1.9±0.2 | 0.58±0.05 | 1.60 | 7.9 | 1.8 |
| PBzMA-hbPDMS-PBzMA | | | | | | | | |
| B1000-1 | 1010 | 170 | 0.05 | 1.5±0.1 | 0.35±0.02 | 2.0 | 3.0 | 2.6 |
| B1000-2 | | 230 | 0.06 | 2.1±0.1 | 0.37±0.02 | 2.0 | 3.9 | 2.0 |
| B1000-3 | | 340 | 0.10 | 2.3±0.1 | 0.40±0.02 | 1.9 | 5.1 | 2.5 |
| B1000-4 | 940 | 1100 | 0.25 | 1.6±0.1 | 0.66±0.03 | 1.5 | 9.7 | 2.1 |

FIG. 23
(Continued)

SELF-ASSEMBLED ELASTOMERS WITH MOLECULARLY ENCODED TISSUE-LIKE SOFTNESS, STRAIN-ADAPTIVE STIFFENING AND COLORATION

CROSS-REFERENCE TO RELATED APPLICATIONS

This Application is a U.S. National Phase of International Application No. PCT/US2018/049300, filed on Sep. 3, 2018, which claims the benefit of U.S. Provisional Application No. 62/553,870, filed on Sep. 3, 2017, U.S. Provisional Application No. 62/585,124, filed on Nov. 13, 2017, and U.S. Provisional Application No. 62/634,843, filed on Feb. 24, 2018, the contents of which are incorporated herein by reference in their entireties.

STATEMENT REGARDING FEDERALLY SPONSORED RESEARCH

This invention was made with government support under Grant Nos. DMR 1407645, DMR 1436201, and DMR 1624569 awarded by the National Science Foundation and under Grant No. DE-SC0001011 awarded by the U.S. Department of Energy. The government has certain rights in the invention.

BACKGROUND

The mechanical and optical properties of biological tissues emerge from distinct physical origins, but act in concert to serve living organisms such as chameleons, cephalopods, and amphibians (Teyssier et al. (2015) *Nat. Comm.* 6: 6368; Mäthger et al. (2009) *J. R. Soc. Interface* 6: 149-163; Cuthill et al. (2017) *Science* 357, eaan0221). For example, initially soft and compliant tissues such as skin stiffen rapidly during deformation to prevent injury. Within narrow intervals of strain, their elastic moduli increase by several orders of magnitude at rates far beyond those observed in conventional elastomers, gels, and thermoplastics. These tissues may also simultaneously convert white light into colorful patterns through the constructive interference of light waves coherently scattered by periodic or quasi-periodic structures (Teyssier et al. (2015) Nat. Comm. 6: 6368). Collectively, these functions constitute remarkable defense and signaling mechanisms that have inspired the design of various biomimetic materials that either possess tissue-like mechanics (Teyssier et al. (2015) *Nat. Comm.* 6: 6368; Mäthger et al. (2009) *J. R. Soc. Interface* 6: 149-163; Cuthill et al. (2017) *Science* 357, eaan0221; Vigneron and Simonis (2012) *Phys B Condens Matter.* 407: 4032-4036; Vantankhah-Varnosfaderani et al. (2017) *Nature* 549: 497-501; Grindy et al. (2015) *Nat. Mater.* 14: 1210-1216; Yu et al. (2016) *Nature Mater.* 15: 911-918) or display structural colors (Grindy et al. (2015) *Nat. Mater.* 14: 1210-1216; Yu et al. (2016) *Nature Mater.* 15: 911-918; So et al. (2014) *Adv. Funct. Mater.* 24: 7197-7204). However, integrating both attributes into the molecular structure of a single material proves extremely challenging.

The mechanics of biological tissues arise from their composite nature, defined by the distinct mechanical response of two proteins—collagen and elastin (Yu et al. (2016) *Nature Mater.* 15: 911-918). A scaffold of stiff collagen fibers resists deformation, while an interwoven elastin network ensures elastic recoil. This structural duet produces a characteristic, two-phase mechanical response (Yu et al. (2016) *Nature Mater.* 15: 911-918): (i) exponential stiffening that switches to a (ii) linear response ( ) halfway before rupture as exhibited by plotting differential modulus $$\partial \sigma_{true}/\partial \lambda$$

as a function of $$\lambda.$$

The resulting sigmoid shape of the $$\partial \sigma_{true}/\partial \lambda$$

curves contrasts with the steady increase in stiffness displayed by synthetic elastomers and gels. While various molecular and macroscopic constructs implement the basic principles of strain-stiffening (Grindy et al. (2015) *Nat. Mater.* 14: 1210-1216; Yu et al. (2016) *Nature Mater.* 15: 911-918; So et al. (2014) *Adv. Funct. Mater.* 24: 7197-7204; Yang et al. (2014) *Nature Comm.* 6, 6649/1-10; Jaspers et al. (2017) *Nature Comm.* 8: 15478; Ducrot (2014) *Science* 344: 186-189), none replicate tissue's deformation response completely and precisely. For example, various silicone rubbers, such as Ecoflex® and Dragon Skin®, which are widely used in orthotics and cinematography (Yu et al. (2016) *Nature Mater.* 15: 911-918), possess skin-like softness but lack its strain-stiffening characteristics. Polymeric gels are similarly incapable of replicating tissue mechanics and further suffer from solvent leakage upon deformation (Yu et al. (2016) *Nature Mater.* 15: 911-918).

Recently, softness and strain-stiffening were simultaneously enhanced by employing brush-like architecture in solvent-free elastomers (Yu et al. (2016) *Nature Mater.* 15: 911-918). The attachment of side-chains to network strands yielded a dual mechanical effect: (i) moduli reduced to 100 Pa via chain disentanglement and (ii) strain-stiffening increased by an order of magnitude via strand extension due to side-chain steric repulsion (Yu et al. (2016) *Nature Mater.* 15: 911-918). While this enables mechanical replicas of gel-like tissues such as lung and jellyfish (Vantankhah-Varnosfaderani et al. (2017) *Nature* 549: 497-501), the strain-stiffening of these systems pales when compared to that of soft connective tissues like skin. In parallel, various chromogenic polymers have been created (Yu et al. (2016) *Nature Mater.* 15: 911-918; So et al. (2014) *Adv. Funct. Mater.* 24: 7197-7204), but fail to incorporate tissue-like mechanical properties. This conventional divide presents a material design challenge aimed at mimicking skin tissue: soft on touch, stiff upon deformation, and colored for appeal or camouflage. Accordingly, there remains a need for synthetic elastomers that mimic biological stress-strain behavior. These needs and others are met by the present invention.

SUMMARY

In accordance with the purpose(s) of the invention, as embodied and broadly described herein, the invention, in one aspect, relates to linear-bottlebrush-linear copolymer blocks and linear-comb-linear copolymer blocks that can be useful in, for example, coalescing biological coloration and mechanical response into moldable elastomers.

Disclosed are copolymer blocks comprising a first linear polymer block, a brush-like polymer block, and a second linear polymer block, wherein the brush-like polymer block is positioned between the first and second linear polymer blocks. In various aspects, the first linear polymer block and/or the second linear polymer block are linear multi-block copolymers. In various aspects, the brush-like polymer block is a brush-like multi-block copolymer. Thus, in various aspects, a disclosed copolymer block can be represented as LnL2L IBnB2B1(Initiator)B1B2BnL1L2Ln, wherein LnL2L1 and L1 L2Ln are first and second linear polymer blocks, respectively, composed of linear multi-block copolymers and wherein BnB2B1(Initiator)B1B2Bn is a brush-like polymer block composed of brush-like multi-block copolymers.

Also disclosed are methods of making a disclosed copolymer block, the method comprising the step of synthesizing the copolymer block from a first residue of the first linear homo and co-polymer block, a residue of the brush-like homo and co-polymer block, and a second residue of the second linear homo and co-polymer block, wherein synthesizing is via free radical polymerization (FRP), atom transfer radical polymerization (ATRP), SARA ATRP, anionic polymerization, or reversible addition-fragmentation chain-transfer polymerization (RAFT) and click reactions such as azide/alkyne-TCO, thiol/alkene or combination of these techniques.

Also disclosed are methods of making a disclosed copolymer block, the method comprising the step of synthesizing the copolymer block from a first residue of the first linear polymer block, a residue of the brush-like polymer block, and a second residue of the second linear polymer block, wherein synthesizing is via free radical polymerization (FRP), atom transfer radical polymerization (ATRP), SARA ATRP, anionic polymerization, or reversible addition-fragmentation chain-transfer polymerization (RAFT).

Also disclosed are polymer networks comprising a plurality of disclosed copolymer blocks.

Also disclosed are articles formed from a disclosed polymer network.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

FIG. 22 shows the mechanical properties of all PDMS-based elastomers synthesized in Experimental 1.

FIG. 23 shows a summary of the molecular and mechanical parameters of the studied plastomers.

Figure 1B:
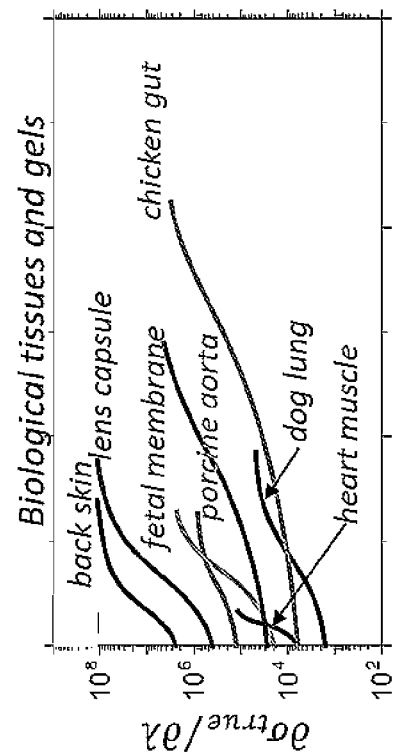
FIG. 1A and FIG. 1B show representative data illustrating the distinct mechanics of biological tissue.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

The present invention now will be described more fully hereinafter with reference to the accompanying drawings, in which illustrative aspects of the invention are shown. In the drawings, the relative sizes of regions or features may be exaggerated for clarity. This invention may, however, be embodied in many different forms and should not be construed as limited to the aspects set forth herein; rather, these aspects are provided so that this disclosure will be thorough and complete, and will fully convey the scope of the invention to those skilled in the art.

The disclosures of all patent references cited herein are hereby incorporated by reference to the extent they are consistent with the disclosure set forth herein. As used herein in the description of the invention and the appended claims, the singular forms "a," "an," and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular aspects only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in various aspects of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

The term "about," as used herein when referring to a measurable value, such as, for example, an amount or concentration and the like, is meant to encompass variations of ±20%, ±10%, ±5%, ±1%, ±0.5%, or even±0.1% of the specified amount. A range provided herein for a measureable value may include any other range and/or individual value therein.

As used herein, "polymer network" refers to a polymer in which covalent cross-linking or non-covalent cross-linking (e.g., via chain entanglements, hydrogen bonding, or microphase separation) has occurred. Examples of polymer networks include, but are not limited to, polymer gels and elastomers.

As used herein, "polymer" refers to the product of a polymerization reaction in which one or more monomers are linked together. A polymer includes both homopolymers and copolymers. Additionally, a polymer can be linear, brush-like, crosslinked, or a mixture thereof.

As used herein, "homopolymer" refers to a polymer resulting from the polymerization of a single monomer.

As used herein, "copolymer" refers to a polymer resulting from the polymerization of two or more chemically distinct monomers.

As used herein, "linear polymer" refers to a polymer having side chains that are shorter than the spacer between neighboring side chains along the backbone or main chain of the polymer. When the spacer is negligibly short, "linear polymer" refers to a polymer having side chains that are shorter than the persistence length of the side chains. For example, a polymer chain with side chains, in which the spacer consists of two covalent bonds and side chain persistence length is ten covalent bonds long, is considered as a "linear polymer." Examples of linear polymers include, but are not limited to, vinyl polymers with relatively short side chains or small side groups. When the side chains become longer than their persistence length, the polymer is no longer considered a linear polymer. Rather, the polymer is now considered a brush-like polymer as further detailed below. For example, poly(butyl acrylate) with n-butyl side groups is a linear polymer whereas poly(octadecyl acrylate) with n-octadecyl side chains is a brush-like polymer.

As used herein, "comb-like polymer block" refers to a brush-like polymer block in which the spacer length is significantly shorter than the side chain contour length, yet it is longer than the square-root of the side chain length. For example, a comb-like polymer block could have poly(butyl acrylate) side chains with a degree of polymerization of 100 separated by a poly(butyl acrylate) spacer with a degree of polymerization of 30 (30<<100).

As used herein, "bottlebrush-like polymer block" refers to a polymer block having side chains that are significantly longer than the spacer between neighboring side chains along the backbone or main chain of the polymer. Thus, without wishing to be bound by theory, the side chains can be at least more than two monomeric units long, more than 3 monomeric units long, more than 4 monomeric units long, more than 5 monomeric units long, more than 6 monomeric units long, more than 7 monomeric units long, or more than 8 monomeric units long, so long as the spacer is shorter than the square-root of the side chain length. For example, a bottlebrush-like polymer block could have poly(butyl acrylate) side chains with a degree of polymerization of 100 separated by a poly(butyl acrylate) spacer with a degree of polymerization of 2 ($2<<<\sqrt{(100)}$)).

As used herein, "amorphous" refers to a state of matter that is not crystalline, i.e., that has no lattice structure that is characteristic of a crystalline state. Thus, in various aspects, a polymer block can be at least 1% amorphous, at least 5% amorphous, at least 10% amorphous, at least 15% amorphous, at least 20% amorphous, at least 30% amorphous, at least 40% amorphous, at least 50% amorphous, at least 60% amorphous, at least 70% amorphous, at least 80% amorphous, at least 90% amorphous, or even at least 99% amorphous. Without wishing to be bound by theory, an amorphous block enables better control of network structure and network formation process via microphase separation.

As used herein, "binding functionality" refers to a chemical group capable of binding polymer blocks, e.g., linear polymer blocks. In various aspects, a binding functionality is capable of covalently binding polymer blocks; however, non-covalent binding (e.g., via hydrogen bonds, ionic bonds, and Van der Waals forces) are also envisioned. Examples of binding functionalities include, but are not limited to, maleimide moieties, vinyl moieties, acrylate moieties, methacrylate moieties, hydroxyl moieties, amino moieties, carboxylic acid moieties, amide moieties, urea moieties, and furan moieties.

As used herein, "elastic modulus" refers to the degree of stiffness of a polymer network). Thus, in various aspects, a polymer network has an elastic modulus of less than about $10^6$ Pa, less than about $10^1$ Pa, or less than about $10^4$ Pa.

As used herein, "strain stiffening parameter" refers to the ability of a polymer network to increase its stiffness (i.e., increase in the polymer network's elastic modulus) during deformation.

As used herein, "reversible molding" refers to the ability of a polymer network to make a shape and then disassemble that shape, if needed, followed by re-assembly into a different shape. Without wishing to be bound by theory, molding can be done from solution state or from melt state.

As used herein, "biocompatible" refers to materials that are not unduly reactive or harmful to a subject upon administration.

B. Copolymer Blocks

In one aspect, disclosed are copolymer blocks comprising a first linear polymer block, a brush-like polymer block, and a second linear polymer block, wherein the brush-like polymer block is positioned between the first and second linear polymer blocks.

In a further aspect, the first linear polymer residue is a residue of a polymer selected from poly(butyl acrylate), poly(butyl methacrylate), poly(butyl norbornene), polystyrene, polydimethylsiloxane, poly(N-isopropylacrylamide), polyoxazolines, polyolefins, polyimides, and polyethylene glycol, and the brush-like polymer block comprises the reaction product of: (a) a first monomer having a structure represented by a formula:

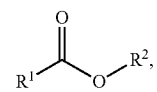

wherein $R^1$ is a structure represented by a formula selected from:

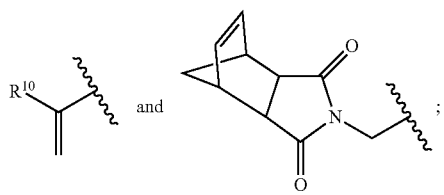

wherein $R^{10}$, when present, is selected from hydrogen and methyl; wherein $R^2$ is a first linear polymer residue; and (b) a diluent monomer.

In a further aspect, the second linear polymer residue is a residue of a polymer selected from polydimethylsiloxane, polycaprolactone, polystyrene, and poly(butyl acrylate), and the brush-like polymer block comprises the reaction product of: (a) a first monomer having a structure represented by a formula:

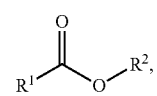

wherein $R^1$ is a structure represented by a formula selected from:

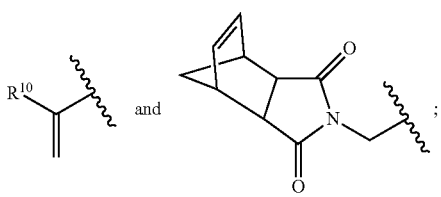

wherein $R^{10}$, when present, is selected from hydrogen and methyl; wherein $R^2$ is a first linear polymer residue; and
(b) a diluent monomer.

In a further aspect, the copolymer block is a tri-block copolymer. In a still further aspect, the tri-block copolymer is represented by a formula A-B-A', wherein A is the first linear block homo or block co-polymer, B is the brush-like homo or block co-polymer, and A' is the second linear block homo or block co-polymer.

In a further aspect, the copolymer block is a tri-block copolymer. In a still further aspect, the tri-block copolymer is represented by a formula A-B-A', wherein A is the first linear polymer block, B is the brush-like polymer block, and A' is the second linear polymer block.

In a further aspect, the copolymer block has a purity of at least about 80%, at least about 85%, at least about 90%, at least about 95%, or at least about 99%.

1. Linear Polymer Blocks

In one aspect, disclosed are linear polymer blocks. As used herein, "linear polymer block" refers to a polymer block having side chains that are shorter than the spacer between neighboring side chains along the backbone or main chain of the polymer as further detailed above. A linear polymer block can be a homopolymer or a copolymer (i.e., can contain the same or different monomeric units). In various aspects, a linear polymer block is a linear block copolymer. Alternatively, a linear polymer block is a multi linear block. In various aspects, a linear polymer block can have a binding functionality as further described herein. Examples of a linear polymer blocks include, but are not limited to, vinyl polymers (e.g., polystyrene, poly(vinyl acetate), poly(acrylo nitrile), and poly(vinyl alcohol)), alkyl acrylate derivatives, alkyl methacrylate derivatives (e.g., poly(methyl methacrylate) and poly(benzyl methacrylate)), ether acrylate derivatives, ether methacrylate derivatives (e.g., poly(oligo(ethylene glycol) monomethyl ether methacrylate), olefin acrylate derivatives, olefin methacrylate derivatives, and olefin norbornene derivatives.

In a further aspect, the first linear homo or co-polymer block and the second linear homo or co-polymer block are the same. In a still further aspect, the first linear homo or co-polymer block and the second linear homo or co-polymer block are different.

In a further aspect, the first linear polymer block and the second linear polymer block are the same. In a still further aspect, the first linear polymer block and the second linear polymer block are different.

In a further aspect, each linear block is amorphous.

In a further aspect, each linear block is either a methacrylate derivative, an acrylate derivative, a methacrylate derivative, a styrene derivative, an oxazoline derivative, an acrylamide derivative, an imide derivative, or a norbornene derivative. In a still further aspect, each linear block is independently selected from poly(methyl methacrylate), poly(benzyl methacrylate), polystyrene, poly(vinyl acetate), polyacrylamide, polyoxazoline, polyolefin, polyimide, polycarbonate, and poly(oligo(ethylene glycol) monomethyl ether methacrylate.

In a further aspect, the first linear polymer block is a residue of a polymer selected from poly(butyl acrylate), poly(butyl methacrylate), poly(butyl norbornene), poly(N-isopropylacrylamide), polystyrene, polydimethylsiloxane, and polyethylene glycol.

In a further aspect, the second linear polymer block is a residue of a polymer selected from polydimethylsiloxane, polycaprolactone, and poly(butyl acrylate).

In a further aspect, the first and second linear polymer blocks have a number average degree of polymerization of from about 100 to about 1500. In a still further aspect, the first and second linear polymer blocks have a number average degree of polymerization of from about 100 to about 1250, of from about 100 to about 1000, of from about 100 to about 750, of from about 100 to about 500, of from about 100 to about 250, of from about 250 to about 1500, of from about 500 to about 1500, of from about 750 to about 1500, of from about 1000 to about 1500, of from about 1250 to about 1500, of from about 250 to about 1250, or of from about 500 to about 1000. In yet a further aspect, the first and second linear polymer blocks have a number average degree of polymerization of about 57, about 117, about 170, about 181, about 230, about 340, about 1100, about 190, about 295, about 325, about 351, about 360, about 365, about 480, about 545, about 656, about 677, about 780, about 803, about 810, about 930, or about 1235. In various aspects, the number average degree of polymerization is determined by $^1$H NMR. Alternatively, in various aspects, the number average degree of polymerization is determined by AFM.

In a further aspect, the first linear polymer block has a volume fraction of from about 0.01 to about 0.50. In a still further aspect, the first linear polymer block has a volume fraction of from about 0.01 to about 0.40, of from about 0.01 to about 0.30, of from about 0.01 to about 0.20, of from about 0.01 to about 0.10, of from about 0.01 to about 0.05, of from about 0.05 to about 0.50, of from about 0.10 to about 0.50, of from about 0.20 to about 0.50, of from about 0.30 to about 0.50, of from about 0.40 to about 0.50, of from about 0.03 to about 0.40, of from about 0.03 to about 0.20, or of from about 0.03 to about 0.10. In yet a further aspect, the first linear polymer block has a volume fraction of about 0.03, 0.05, about 0.06, about 0.07, about 0.08, about 0.09, 0.10, 0.11, 0.16, 0.18, 0.19, or about 0.36.

In a further aspect, the second linear polymer block has a volume fraction of from about 0.01 to about 0.50. In a still further aspect, the second linear polymer block has a volume fraction of from about 0.01 to about 0.40, of from about 0.01 to about 0.30, of from about 0.01 to about 0.20, of from about 0.01 to about 0.10, of from about 0.01 to about 0.05, of from about 0.05 to about 0.50, of from about 0.10 to about 0.50, of from about 0.20 to about 0.50, of from about 0.30 to about 0.50, of from about 0.40 to about 0.50, of from about 0.03 to about 0.40, of from about 0.03 to about 0.20, or of from about 0.03 to about 0.10.

2. Brush-Like Polymer Blocks

In one aspect, disclosed are brush-like polymer blocks. As used herein, "brush-like polymer block" refers to both bottlebrush-like polymer blocks and comb-like polymer blocks as further detailed herein. Thus, in various aspects, a brush-like polymer block can be a sparsely grafted comb. Alternatively, a brush-like polymer block can be a densely grafted bottlebrush (i.e., a brush-like polymer block in which the degree of polymerization of the spacer is significantly smaller than the square root of the degree of polymerization of the side chains). Brush-like polymer blocks can include both homopolymer and copolymer side chains (i.e., can contain the same or different units).

In a further aspect, the brush-like polymer block is a comb-like polymer block. In a still further aspect, the brush-like polymer block is a bottlebrush-like polymer block.

In a further aspect, the brush-like polymer block comprises the reaction product of: (a) a first monomer having a structure represented by a formula:

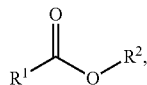

wherein $R^1$ is a structure represented by a formula selected from:

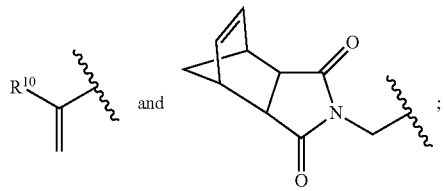

wherein $R^{10}$, when present, is selected from hydrogen and methyl; wherein $R^2$ is a first linear polymer residue; and (b) a diluent monomer.

In a further aspect, the brush-like polymer block comprises at least one residue having a structure represented by a formula selected from:

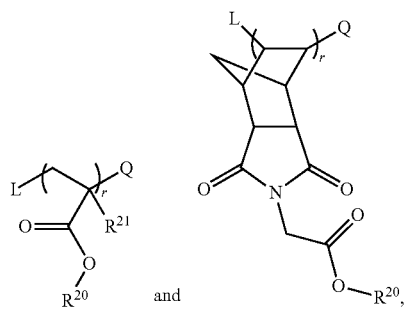

wherein r is an integer selected from 2 to 800; wherein L is an active site of polymerization or a residue of a radical initiator; wherein Q is an active site of polymerization or a residue of a radical intiator; wherein each occurrence of $R^{20}$ is independently selected from a first linear polymer residue and a diluent monomer residue, provided that at least one occurrence of $R^{20}$ is a first linear polymer residue and at least one occurrence of $R^{20}$ is a diluent monomer residue; and wherein each occurrence of $R^{21}$, when present, is independently selected from hydrogen and methyl.

In a further aspect, L and Q are the same. In a still further aspect, L and Q are different. Examples of active sites of polymerization include, but are not limited to, active functional groups such as hydroxyl, thiol, carboxylic acid, carboxylate, azide, furan, and propargyl and inactive groups such as hydrogen, methyl, and alkyl. In a still further aspect, L is halogen. In yet a further aspect, L is —Br. In yet a further aspect, Q is halogen. In an even further aspect, Q is —Br. In a still further aspect, each of L and Q are halogen. In yet a further aspect, each of L and Q is —Br.

In a further aspect, the brush-like polymer block comprises at least one residue having a structure represented by a formula:

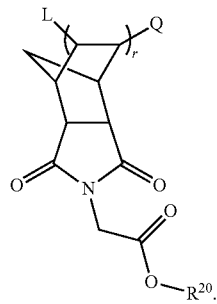

In a further aspect, the brush-like polymer block comprises at least one residue having a structure represented by a formula:

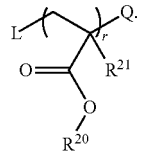

In a further aspect, the brush-like polymer block is a polydimethylsiloxane derivative.

In a further aspect, the brush-like polymer block has a number average degree of polymerization of from about 200 to about 2000. In a still further aspect, the brush-like polymer block as a number average degree of polymerization of from about 200 to about 1750, of from about 200 to about 1500, of from about 200 to about 1250, of from about 200 to about 1000, of from about 200 to about 750, of from about 200 to about 500, of from about 500 to about 2000, of from about 750 to about 2000, of from about 1000 to about 2000, of from about 1250 to about 2000, of from about 1500 to about 2000, of from about 1750 to about 2000, of from about 500 to about 1500, or of from about 750 to about 1250. In yet a further aspect, the brush-like polymer block has a number average degree of polymerization of about 302, about 602, about 938, about 940, about 1010, about 1065, or about 1765. In an even further aspect, the brush-like polymer block has a number average degree of polymerization of about 585, about 902, or about 1163. In various aspects, the number average degree of polymerization is determined by $^1$H NMR. Alternatively, in various aspects, the number average degree of polymerization is determined by AFM. 100891 In a further aspect, the brush-like polymer block has a number average molecular weight of from about 500,000 g/mol to about 1,500,000 g/mol. In a still further aspect, the brush-like polymer block has a number average molecular weight of from about 500,000 g/mol to about 1,250,000 g/mol, of from about 500,000 g/mol to about 1,000,000 g/mol, of from about 500,000 g/mol to about 750,000 g/mol, of from about 750,000 g/mol to about 1,500,000 g/mol, of from about 1,000,000 g/mol to about 1,500,000 g/mol, of from about 1,250,000 to about 1,500,000 g/mol, or of from about 750,000 g/mol to about 1,250,000 g/mol. In yet a further aspect, the brush-like polymer block has a number average molecular weight of about 585,000 g/mol, about 902,000 g/mol, or about 1,163,000 g/mol.

In a further aspect, the brush-like polymer block has a weight average of from about 500,000 g/mol to about 1,500,000 g/mol. In a still further aspect, the brush-like polymer block has a weight average of from about 500,000 g/mol to about 1,250,000 g/mol, of from about 500,000 g/mol to about 1,000,000 g/mol, of from about 500,000 g/mol to about 750,000 g/mol, of from about 750,000 g/mol to about 1,500,000 g/mol, of from about 1,000,000 g/mol to about 1,500,000 g/mol, of from about 1,250,000 to about 1,500,000 g/mol, or of from about 750,000 g/mol to about 1,250,000 g/mol. In yet a further aspect, the brush-like polymer block has a weight average of about 585,000 g/mol, about 902,000 g/mol, or about 1,163,000 g/mol.

In a further aspect, the brush-like polymer block has a volume fraction of from about 0.5 to about 0.99. In a still further aspect, the brush-like polymer block has a volume fraction of from about 0.99 to about 0.60, of from about 0.99 to about 0.70, of from about 0.99 to about 0.80, of from about 0.99 to about 0.90, of from about 0.99 to about 0.95, of from about 0.95 to about 0.50, of from about 0.90 to about 0.50, of from about 0.80 to about 0.50, of from about 0.70 to about 0.50, of from about 0.60 to about 0.50, of from about 0.97 to about 0.60, of from about 0.97 to about 0.80, or of from about 0.97 to about 0.90.

In a further aspect, the brush-like polymer block has a polydispersity of from about 1.00 to about 1.50. In a still further aspect, the brush-like polymer block has a polydispersity of from about 1.00 to about 1.45, of from about 1.00 to about 1.40, of from about 1.00 to about 1.35, of from about 1.00 to about 1.30, of from about 1.00 to about 1.25, of from about 1.00 to about 1.20, of from about 1.00 to about 1.15, of from about 1.15 to about 1.50, of from about 1.20 to about 1.50, of from about 1.25 to about 1.50, of from about 1.30 to about 1.50, of from about 1.35 to about 1.50, of from about 1.40 to about 1.50, or of from about 1.45 to about 1.50. In yet a further aspect, the brush-like polymer block has a polydispersity of about 1.08, about 1.16, or about 1.18.

In one aspect, r is an integer selected from 2 to 800. In a further aspect, r is an integer selected from 2 to 750, 2 to 700, 2 to 650, 2 to 600, 2 to 550, 2 to 500, 2 to 450, 2 to 400, 2 to 350, 2 to 300, 2 to 250, 2 to 200, 2 to 150, 2 to 100, 2 to 50, 50 to 800, 100 to 800, 150 to 800, 200 to 800, 250 to 800, 300 to 800, 350 to 800, 400 to 800, 450 to 800, 500 to 800, 550 to 800, 600 to 800, 650 to 800, 700 to 800, or 750 to 800.

In one aspect, L is a residue of a radical initiator. Examples of radical initiators include, but are not limited to, dialkyl peroxides, diacylperoxides, hydroperoxides, peresters, peroxide dicarbonates, perketals, ketone peroxides, azo compounds, CC-cleaving initiators, multiple-functionalized initiators and combinations thereof.

In one aspect, Q is a residue of a quenching agent. Examples of quenching agents include, but are not limited to, agents that have chain transfer ability such as, for example, a mercaptan.

a. $R^1$ Groups

In one aspect, $R^1$ is a structure represented by a formula selected from:

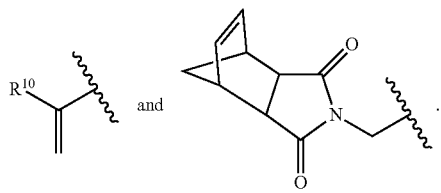

In a further aspect, $R^1$ is a structure:

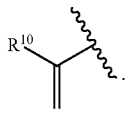

In a further aspect, $R^1$ is a structure:

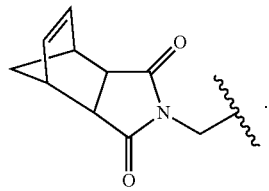 [SMILES: *CN1C(=O)C2C3C=CC(C3)C2C1=O]

b. $R^2$ Groups

In one aspect, $R^2$ is a first linear polymer residue. Examples of linear polymer residues include, but are not limited to, residues of vinyl polymers (e.g., polystyrene, poly(vinyl acetate), poly(acrylo nitrile), and poly(vinyl alcohol)), residues of alkyl acrylate derivatives, residues of alkyl methacrylate derivatives (e.g., poly(methyl methacrylate) and poly(benzyl methacrylate)), residues of ether acrylate derivatives, residues of ether methacrylate derivatives (e.g., poly(oligo(ethylene glycol) monomethyl ether methacrylate), residues of olefin acrylate derivatives, residues of olefin methacrylate derivatives, and residues of olefin norbornene derivatives.

c. $R^{10}$ Groups

In one aspect, $R^{10}$, when present, is selected from hydrogen and methyl. In a further aspect, $R^{10}$, when present, is hydrogen. In a further aspect, $R^{10}$, when present, is methyl.

d. $R^{20}$ Groups

In one aspect, each occurrence of $R^{20}$ is independently selected from a first linear polymer residue and a diluent monomer residue, provided that at least one occurrence of $R^{20}$ is a first linear polymer residue and at least one occurrence of $R^{20}$ is a diluent monomer residue.

Examples of linear polymer residues include, but are not limited to, residues of vinyl polymers (e.g., polystyrene, poly(vinyl acetate), poly(acrylo nitrile), and poly(vinyl alcohol)), residues of alkyl acrylate derivatives, residues of alkyl methacrylate derivatives (e.g., poly(methyl methacrylate) and poly(benzyl methacrylate)), residues of ether acrylate derivatives, residues of ether methacrylate derivatives (e.g., poly(oligo(ethylene glycol) monomethyl ether methacrylate), residues of olefin acrylate derivatives, residues of olefin methacrylate derivatives, and residues of olefin norbornene derivatives.

Examples of diluent monomer residues include, but are not limited to, residues of alkyl acrylate monomers (e.g., butyl acrylate, butyl methacrylate, isopropyl acrylate, n-propyl acrylate, and ethyl acrylate), residues of methacrylate monomers (e.g., isopropyl methacrylate, n-propyl methacrylate, and ethyl methacrylate), and residues of norbornene monomers.

e. $R^{21}$ Groups

In one aspect, each occurrence of $R^{21}$, when present, is independently selected from hydrogen and methyl. In a further aspect, each occurrence of $R^{21}$, when present, is hydrogen. In a still further aspect, each occurrence of $R^{21}$, when present, is methyl.

f. Diluent Monomers

In one aspect, disclosed are diluent monomers. As used herein, "diluent monomer" refers to a relatively small monomer (i.e., smaller than macromonomers used for polymerization of comb-like polymers and bottlebrush-like polymers) that is useful for adjusting viscosity and exhibits one or more of good weatherability, high reactivity, low shrinkage, good adhesion, and a non-rigid structure. Examples of diluent monomers include, but are not limited to, alkyl acrylate monomers (e.g., butyl acrylate, butyl methacrylate, isopropyl acrylate, n-propyl acrylate, and ethyl acrylate), methacrylate monomers (e.g., isopropyl methacrylate, n-propyl methacrylate, and ethyl methacrylate), and norbornene monomers.

In a further aspect, the molar ratio of the diluent monomer to the macromonomer is about 1:1. In a still further aspect, the ratio of the monomer to the diluent monomer is about 2:1. In yet a further aspect, the ratio of the monomer to the diluent monomer is about 4:1. In an even further aspect, the ratio of the monomer to the diluent monomer is about 10:1. In a still further aspect, the ratio of the monomer to the diluent monomer is about 20:1. In yet a further aspect, the ratio of the monomer to the diluent monomer is about 50:1. In an even further aspect, the ratio of the monomer to the diluent monomer is about 100:1.

C. Methods of Making Copolymer Blocks

In one aspect, disclosed are methods of making a disclosed copolymer block. Thus, in various aspects, disclosed are methods of making a copolymer block comprising a first linear polymer block, a brush-like polymer block, and a second linear polymer block, wherein the brush-like polymer block is positioned between the first and second linear polymer blocks, the method comprising the step of synthesizing the copolymer block from a first residue of the first linear polymer block, a residue of the brush-like polymer block, and a second residue of the second linear polymer block, wherein synthesizing is via free radical polymerization (FRP), atom transfer radical polymerization (ATRP), SARA ATRP, anionic polymerization, or reversible addition-fragmentation chain-transfer polymerization (RAFT).

In a further aspect, synthesizing is via ATRP.

In a further aspect, synthesizing is in the presence of a catalytically effective amount of a radical initiator. In a still further aspect, the radical initiator is an alkyl halide. In yet a further aspect, the alkyl halide is an alkyl polyhalide. In an even further aspect, the alkyl halide is an alkyl dihalide.

In a further aspect, the radical initiator is a photoinitiator.

In a further aspect, the residue of the brush-like polymer block acts as a radical initiator.

In a further aspect, the catalytically effective amount of the radical initiator is of from about 25 mol % to about 250 mol %. In a still further aspect, the catalytically effective amount of the radical initiator is of from about 25 mol % to about 200 mol %. In yet a further aspect, the catalytically effective amount of the radical initiator is of from about 25 mol % to about 150 mol %. In an even further aspect, the catalytically effective amount of the radical initiator is of from about 25 mol % to about 100 mol %. In a still further aspect, the catalytically effective amount of the radical initiator is of from about 25 mol % to about 50 mol %. In an even further aspect, the catalytically effective amount of the radical initiator is of from about 50 mol % to about 250 mol %. In a still further aspect, the catalytically effective amount of the radical initiator is of from about 100 mol % to about 250 mol %. In yet a further aspect, the catalytically effective amount of the radical initiator is of from about 150 mol % to about 250 mol %. In an even further aspect, the catalytically effective amount of the radical initiator is of from about 200 mol % to about 250 mol %. In a still further aspect, the catalytically effective amount of the radical initiator is of from about 50 mol % to about 200 mol %. In yet a further aspect, the catalytically effective amount of the radical initiator is of from about 75 mol % to about 175 mol %. In an even further aspect, the catalytically effective amount of the radical initiator is of from about 100 mol % to about 150 mol %. In a still further aspect, the catalytically effective amount of the radical initiator is of from about 50 mol % to about 200 mol %.

In a further aspect, synthesizing is in the presence of a catalytically effective amount of a transition metal catalyst. Examples of transition metal catalysts include, but are not limited to, copper catalysts and iron catalysts.

In a further aspect, the transition metal catalyst is a copper catalyst. Examples of copper catalysts include, but are not limited to, copper (0), copper (I) sulfide, copper (I) telluride, copper (I) selenide, copper (I) chloride, copper (II) chloride, copper (I) bromide, and copper (II) bromide, or a mixture thereof. In a still further aspect, the copper catalyst is copper (I) chloride.

In a further aspect, the catalytically effective amount of the transition metal catalyst is of from about 0.001 mol % to about 0.2 mol %. In a still further aspect, the catalytically effective amount of the transition metal catalyst is of from about 0.001 mol % to about 0.15 mol %. In yet a further aspect, the catalytically effective amount of the transition metal catalyst is of from about 0.001 mol % to about 0.1 mol %. In an even further aspect, the catalytically effective amount of the transition metal catalyst is of from about 0.001 mol % to about 0.05 mol %. In a still further aspect, the catalytically effective amount of the transition metal catalyst is of from about 0.001 mol % to about 0.01 mol %. In yet a further aspect, the catalytically effective amount of the transition metal catalyst is of from about 0.001 mol % to about 0.005 mol %. In an even further aspect, the catalytically effective amount of the transition metal catalyst is of from about 0.005 mol % to about 0.2 mol %. In a still further aspect, the catalytically effective amount of the transition metal catalyst is of from about 0.01 mol % to about 0.2 mol %. In yet a further aspect, the catalytically effective amount of the transition metal catalyst is of from about 0.05 mol % to about 0.2 mol %. In an even further aspect, the catalytically effective amount of the transition metal catalyst is of from about 0.1 mol % to about 0.2 mol %. In a still further aspect, the catalytically effective amount of the transition metal catalyst is of from about 0.15 mol % to about 0.2 mol %. In yet a further aspect, the catalytically effective amount of the transition metal catalyst is of from about 0.005 mol % to about 0.1 mol %. In an even further aspect, the catalytically effective amount of the transition metal catalyst is of from about 0.01 mol % to about 0.05 mol %. In a still further aspect, the catalytically effective amount of the transition metal catalyst is of from about 0.005 mol % to about 0.1 mol %.

In a further aspect, synthesizing is in the presence of a ligand. Examples of ligands include, but are not limited to, 2,2'-bipyridine (byp), 4,4'-di-5-nonyl-2,2'-bipyridine (dNbpy), 4,4',4"-tris(5-nonyl)-2,2,6',2"-terpyridin (tNtpy), N,N,N',N',N"-pentamethyldiethylenetriamine (PMDETA), 1,1,4,7,10,10-hexamethyltriethylenetetramine, tris(2-dimethylaminoethyl)amine, N,N-bis(2-pyridylmethyl)octadecylamine, N,N,N',N'-tetra[(2-pyridal)methyl]ethylenediamine, tris[(2-pyridyl)methyl]amine, tris(2-aminoethyl) amine ($Me_6TREN$), tris(2-bis(3-butoxy-3-oxopropyl) aminoethyl)amine, tris(2-bis(3-(2-ethylhexoxy)-3-oxopropyl)aminoethyl)amine, and tris(2-bis(3-dodecoxy-3-oxopropyl)aminoethyl)amine, or a mixture thereof. Thus, in various aspects, the ligand is $Me_6TREN$.

Residues of linear polymer blocks can be prepared as disclosed elsewhere herein or as known by one of ordinary skill in the art. In various aspects, the first residue of the first linear polymer block has a purity of at least about 80%, at least about 85%, at least about 90%, at least about 95%, or at least about 99%. In various aspects, the second residue of the second linear polymer block has a purity of at least about 80%, at least about 85%, at least about 90%, at least about 95%, or at least about 99%.

Residues of brush-like polymer blocks can be prepared as disclosed elsewhere herein or as known by one of ordinary skill in the art. In various aspects, the residue of the brush-like polymer block has a purity of at least about 80%, at least about 85%, at least about 90%, at least about 95%, or at least about 99%.

In a further aspect, a copolymer block prepared via a disclosed method has a purity of at least about 80%, at least about 85%, at least about 90%, at least about 95%, or at least about 99%.

D. Polymer Networks

In one aspect, disclosed are polymer networks comprising a plurality of disclosed copolymer blocks. Thus, in various aspects, disclosed are polymer networks comprising a plurality of copolymer blocks, wherein each copolymer block comprises a first linear polymer block, a brush-like polymer block, and a second linear polymer block, wherein the brush-like polymer block is positioned between the first and second linear polymer blocks.

In a further aspect, the copolymer blocks undergo microphase separation to form physically distinct domains composed of linear polymer blocks dispersed within a matrix of the brush-like polymer blocks.

In a further aspect, the copolymer blocks undergo self-assembly to form a physically cross-linked network.

In a further aspect, the first linear polymer block and/or the second linear polymer block has a binding functionality, wherein the binding functionality on one first linear block and/or one second linear block can bond to the binding functionality on a different first linear block and/or different second linear block. Examples of binding functionalities include, but are not limited to, alcohols, thiols, alkenyls, alkynyls, amines, amides, esters, carboxylic acids, sulphonic acids, phosphoric acids, and carbamates.

In a further aspect, the binding functionality on one first linear block and/or one second linear block is bonded to the binding functionality on a second first linear block and/or second linear block, thereby forming a plastomer.

In a further aspect, the polymer network exhibits structural coloration. In a still further aspect, the polymer network's structural coloration changes upon deformation of the polymer network.

In a further aspect, the polymer network is a solvent-free elastomer.

In a further aspect, the solvent-free elastomer has an elastic modulus of about $10^5$ Pa or less. In a still further aspect, the solvent-free elastomer has an elastic modulus of about $10^4$ Pa or less, of about $10^3$ Pa or less, of about $10^2$ Pa or less, or of about $10^1$ Pa or less.

In a further aspect, the solvent-free elastomer has a strain-stiffening parameter of from about 0.1 to about 1. In a still further aspect, the solvent-free elastomer has a strain-stiffening parameter of from about 0.1 to about 0.9, of from about 0.1 to about 0.8, of from about 0.1 to about 0.7, of from about 0.1 to about 0.6, of from about 0.1 to about 0.5, of from about 0.1 to about 0.4, of from about 0.1 to about 0.3, of from about 0.1 to about 0.2, of from about 0.2 to about 1, of from about 0.3 to about 1, of from about 0.4 to about 1, of from about 0.5 to about 1, of from about 0.6 to about 1, of from about 0.7 to about 1, of from about 0.8 to about 1, of from about 0.9 to about 1, of from about 0.2 to about 0.9, of from about 0.3 to about 0.8, or of from about 0.4 to about 0.7.

In a further aspect, the solvent-free elastomer can undergo uniaxial elongation from about 2-fold to about 10-fold. In a still further aspect, the solvent-free elastomer can undergo uniaxial elongation from about 2-fold to about 9-fold, from about 2-fold to about 8-fold, from about 2-fold to about 7-fold, from about 2-fold to about 6-fold, from about 2-fold to about 5-fold, from about 2-fold to about 4-fold, from about 2-fold to about 3-fold, from about 3-fold to about 9-fold, from about 4-fold to about 9-fold, from about 5-fold to about 9-fold, from about 6-fold to about 7-fold, from about 8-fold to about 9-fold, from about 3-fold to about 8-fold, or from about 4-fold to about 7-fold.

In a further aspect, the solvent-free elastomer can undergo reversible molding into a desired shape.

In a further aspect, the polymer network has a structural modulus of from about 0.1 kPa to about 100.0 kPa. In a still further aspect, the polymer network has a structural modulus of from about 0.1 kPa to about 50.0 kPa, of from about 0.1 kPa to about 10.0 kPa, of from about 0.1 kPa to about 5.0 kPa, of from about 0.1 kPa to about 2.0 kPa, of from about 0.1 kPa to about 1.0 kPa, of from about 0.1 kPa to about 0.5 kPa, of from about 0.5 kPa to about 10.0 kPa, of from about 1.0 kPa to about 10.0 kPa, of from about 1.0 kPa to about 10.0 kPa, or of from about 2.0 kPa to about 10.0 kPa, In a further aspect, the polymer network has a strain-stiffening parameter of from about 0.1 to about 0.9. In a still further aspect, the polymer network has a strain-stiffening parameter of from about 0.1 to about 0.9, of from about 0.2 to about 0.8, of from about 0.2 to about 0.7, of from about 0.2 to about 0.6, of from about 0.2 to about 0.5, of from about 0.2 to about 0.4, of from about 0.3 to about 0.9, of from about 0.4 to about 0.9, of from about 0.5 to about 0.9, of from about 0.6 to about 0.9, or of from about 0.3 to about 0.8, or of from about 0.3 to about 0.7.

In a further aspect, the polymer network has an apparent Young's modulus of from about 0.1 kPa to about 1000.0 kPa. In a still further aspect, the polymer network has an apparent Young's modulus of from about 0.1 kPa to about 500.0 kPa, of from about 0.1 kPa to about 200.0 kPa, of from about 0.1 kPa to about 100.0 kPa, of from about 0.1 kPa to about 50.0 kPa, of from about 0.1 kPa to about 20.0 kPa, of from about 0.1 kPa to about 10.0 kPa, of from about 0.1 kPa to about 5.0 kPa, of from about 0.1 kPa to about 1.0 kPa, of from about 0.1 kPa to about 0.5 kPa, of from about 1.0 kPa to about 1000.0 kPa, of from about 1.0 kPa to about 1000.0 kPa, of from about 10.0 kPa to about 1000.0 kPa, of from about 50.0 kPa to about 1000.0 kPa, of from about 100.0 kPa to about 1000.0 kPa, of from about 200.0 kPa to about 1000.0 kPa, of from about 500.0 kPa to about 1000.0 kPa, of from about 1.0 kPa to about 100.0 kPa, of from about 1.0 kPa to about 10.0 kPa, of from about 10.0 kPa to about 100.0 kPa.

In a further aspect, the polymer network has an elongation at break of from about 1.1 to about 10.0. In a still further aspect, the polymer network has an elongation at break of from about 1.1 to about 9.0, of from about 1.1 to about 8.0, of from about 1.1 to about 7.0, of from about 1.1 to about 6.0, of from about 1.1 to about 5.0, of from about 1.1 to about 4.0, of from about 1.2 to about 10.0, of from about 1.5 to about 10.0, of from about 2.0 to about 10.0, of from about 3.0 to about 10.0, of from about 4.0 to about 10.0, of from about 5.0 to about 10.0, or of from about 1.5.0 to about 5.0.

E. Articles

In one aspect, disclosed are articles formed from a disclosed polymer network. In a further aspect, the present invention contemplates the use of the disclosed polymer networks in the manufacture of certain items such as articles. Thus, in various aspects, a disclosed polymer network has been formed as an article such as, for example, implant, a microneedle array, a wound dressing pad, a coating for a medical device (e.g., an implant), or a catheter.

In various aspects, disclosed are articles comprising a disclosed polymer network.

In a further aspect, the polymer network comprises a surface and wherein the surface of the polymer network is at least partially connected to a surface of an object. In a still further aspect, connected is via a non-covalent bond. In yet a further aspect, the elastic modulus of the polymer network is less than about $10^5$ Pa, at least at one temperature range of the object.

In a further aspect, the surface of the polymer network is not tacky at a temperature range of from about 0° C. to about 100° C.

A composition comprising at least one disclosed article, wherein the article forms at least one deformable surface and wherein the polymer network has an elastic modulus of less than about $10^5$ Pa, at least in one temperature range suitable for the composition. Without wishing to be bound by theory, deformation can be essential to the composition. In a further aspect, the deformation is recurrent.

In a further aspect, disclosed are compositions comprising at least one exterior surface formed a disclosed polymer network. In a still further aspect, the surface essentially stops permeation of solid, liquid, or gaseous substances.

In a further aspect, disclosed are devices comprising a disclosed article, wherein the polymer network receives pressure or suction and wherein the polymer network has an elastic modulus of no greater than $10^5$ Pa, at least at one temperature range acceptable for the device. In a still further aspect, the pressure or suction is applied via a biological liquid or tissue.

In a further aspect, the article is morphed to conform to an object's shape, and the elastic modulus of the polymer network is less than about $10^5$ Pa, at least at one temperature range of the object.

In a further aspect, the object is part of an animal or a human body.

In a further aspect, disclosed are compositions having a plurality of disjoint surface segments, wherein the composition comprises at least one disclosed device, wherein the device contacts the plurality of disjoint surface segments, and wherein the device prevents direct contact between the segments.

In a further aspect, the article is formed as a sheet fragment. In a still further aspect, the article is formed as a fiber fragment. In yet a further aspect, the article is formed as a tube fragment.

In a further aspect, disclosed are articles, wherein a part of the article is comprised of a disclosed polymer network. In a still further aspect, the part was stressed by elongation or compression along at least one direction on at least one segment of the part at temperature above phase transition temperature of disclosed residues, and cooled down to a temperature below a transition temperature while maintaining the stress. In a further aspect, the transition temperature is from about 4° C. to about 37° C.

1. Tissue Scaffolds

In one aspect, disclosed are tissue scaffolds formed from a disclosed polymer network. In a further aspect, the tissue scaffolds are two- or three-dimensional. In a still further aspect, the tissue scaffolds are two-dimensional. In yet a further aspect, the tissue scaffolds are three-dimensional.

2. Implants

In one aspect, disclosed are implants formed from a disclosed polymer network.

F. REFERENCES

Yu, B. et al. "An elastic second skin" *Nature Materials* 15, 911-918 (2016) DOI: 10.1038/NMAT4635.

Shergold, O. A., et al. "The uniaxial stress versus strain response of pig skin and silicone rubber at low and high strain rates." *International Journal of Impact Engineering* 32 (2006) 1384-1402.

Wang, Z. et al. "Bioinspired High Resilient Elastomers to Mimic Resilin." *ACS Macro Lett.* (2016) 5, 220-223.

Xu, B. et al. "Mechanically tissue-like elastomeric polymers and their potential as a vehicle to deliver functional cardiomyocytes." *J. Mechanical Behavior of Biomedical Materials* 28, 354-365 (2013).

Minev, I. R.; et al. Electronic dura mater for long-term multimodal neural interfaces." *Science* 347, 159 (2015).

Jeong, J.-W.; et al. "Soft Materials in Neuroengineering for Hard Problems in Neuroscience." *Neuron* 86, 175 (2015).

Georges, P. C., et al. "Matrices with Compliance Comparable to that of Brain Tissue Select Neuronal over Glial Growth in Mixed Cortical Cultures" *Biophysical Journal* 90 3012-3018 (2006).

Moshayedi, P. et al "Mechanosensitivity of astrocytes on optimized polyacrylamide gels analyzed by quantitative morphometry." *J. Phys.: Condens. Matter* 22 (2010) 194114 (11pp).

Sridharan, A.; et al. "Compliant intracortical implants reduce strains and strain rates in brain tissue in vivo" J. Neural Eng. 12 (2015) 036002 (12pp).

Nguyen, J. K.; et al. "Mechanically-compliant intracortical implants reduce the neuroinflammatory response" *J. Neural Eng.* 11 (2014) 056014 (15pp).

Xie, S.; et al. Nanoscaffold's stiffness affects primary cortical cell network formation." *J. Vac. Sci. Technol. B* 32(6), 06FD03-1 (2014). http://dx.doi.org/10.1116/1.4900420.

Knoth Tate, M. L. et al. "Engineering and commercialization of human-device interfaces, from bone to brain" *Biomaterials* 95, 35-46 (2016).

Scholten, K.; et al "Materials for microfabricated implantable devices: a review." *Lab Chip,* 15, 4256 (2015).

Lee, J. H.; et al. "Soft implantable microelectrodes for future medicine: prosthetics, neural signal recording and neuromodulation." *Lab Chip,* 16, 959 (2016).

Wang, W. et al "Camouflage and Display for Soft Machines" *Science* 337, 828-832 (2012).

Lim, G. T., et al. New biomaterial as a promising alternative to silicone breast implants J. Mechanical Behavior of Biomedical Materials 21, 47-56 (2013).

G. M. Whitesides, Soft Robotics. *Angew. Chem. Int. Ed.* 57, 2-18 (2018).

R. H. Baughman, Playing nature's game with artificial muscles. *Science* 308, 63-65 (2005).

S. M. Mirvakili, I. W. Hunter, Artificial Muscles: Mechanisms, Applications, and Challenges. *Adv. Mater.* 30, 1704407/1-28 (2017).

S. Wang, et al., Skin electronics from scalable fabrication of an intrinsically stretchable transistor array. *Nature.* 555, 83-88 (2018).

Trapmann, B. et al. "Extracellular-matrix tethering regulates stem-cell fate" Nature Materials 11, 642-649 (2012) DOI: 10.1038/NMAT3339

Ducrot, E. et al."Toughening elastomers with sacrificial bonds and watching them break." *Science* 344 186-189 (2014).

Mohammad, Faiz, ed. Specialty polymers: Materials and applications. IK International Pvt Ltd, 2007.

Anselmo, A. C.; et al. "Impact of particle elasticity on particle-based drug delivery systems." Advanced Drug Delivery Reviews" 108, 51-67 (2017).

Teo, A. J. T; et al. "Polymeric Biomaterials for Medical Implants and Devices" ACS Biomaterials Science and Engineering 2, 454-472 (2016).

Tenney, R. M.; et al. "Stem cells, microenvironment mechanics, and growth factor activation" Current Opinion in Cell Biology 21, 630-635 (2009).

Discher, D. E.; et al. "Tissue Cells Feel and Respond to the Stiffness of Their Substrate" SCIENCE 310, 1139 (2005).

G. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Experimental I—Mimicking Mechanical Behavior of Biological Materials a. Synthesis and Characterization (i) Materials n-Butyl acrylate (nBA, 99%) and methyl methacrylate (MMA, 98%) were obtained from Acros and purified using a basic alumina column to remove inhibitor. Potassium tert-butoxide (KOtBu) was obtained from Fluka and used as received. Monomethacryloxypropyl-terminated poly(dimethylsiloxane) (MCR-M11, average molar mass 1000 g/mol, PDI=1.15), monoaminopropyl-terminated poly(dimethylsiloxane) (MCR-A12, average molar mass 2000 g/mol, PDI=1.15), and $\alpha,\omega$-methacryloxypropyl-terminated poly(dimethylsiloxane) (DMS-R18, R22, with average molar masses 5000 and 10000 g/mol, respectively, PDI=1.15) were obtained from Gelest and purified using basic alumina columns to remove inhibitor. Methacryloyl chloride (MMACl,>97%), phenylbis(2,4,6-trimethyl-benzoyl)phosphine oxide (BAPOs), triethylamine (TEA), copper(I) chloride (CuCl, >99.995%), copper(I) bromide (CuBr, 99.999%), tris[2-(dimethylamino)ethyl]amine (Me6TREN), N,N,N',N'',N''-pentamethyldiethylenetriamine (PMDETA, 99%), ethyl $\alpha$-bromoisobutyrate (EBiB), $\alpha$-bromoisobutyryl bromide (BIBB, 98%), ethylene bis(2-bromoisobutyrate) (2-BiB, 97%), dimethyl formaldehyde (DMF), dimethyl acetamide (DMA), tetrahydrofuran (THF), p-xylene (PX), and acrylic acid (AA, 99%) were purchased from Aldrich and used as received, as were all other reagents and solvents.

(ii) Synthesis of Poly(N-BA16) Macromonomer

A 100 mL Schlenk flask equipped with a stir bar was charged with EBiB (4.875 g, 25 mmol), nBA (64.0 g, 0.5 mol), PMDETA (0.87 g, 5 mmol), and DMF (16.0 mL). The solution was bubbled with dry nitrogen for 1 hr. Then, CuBr (0.745 g, 5 mmol) was added to the reaction mixture under nitrogen atmosphere. The flask was closed, purged for 5 m with nitrogen, and immersed in an oil bath thermostated at 65° C. The polymerization was stopped after 5 hrs when monomer conversion reached 80 mol % (determined using $^1$H-NMR). The polymer solution was passed through a neutral aluminum oxide column and the unreacted monomers were evaporated by bubbling with nitrogen gas. The remaining polymer (50 g, 24.4 mmol) was dissolved in DMA (100 g) and transferred to a 250 mL flask. Potassium acrylate (8 g, 73.2 mmol) was synthesized by reaction of AA and KOtBu and added to the solution, which was stirred for 72 hrs at room temperature. The solution was filtered, diluted with methylene chloride (DCM, 100 mL), then washed with deionized (DI) water (3×100 mL). The macromonomer solution was dried by adding magnesium sulfate (MgSO4) and then by overnight evaporation in air.

(iii) Synthesis of Poly(N-BA$_{50}$) Macro-Crosslinker

A 25 mL Schlenk flask equipped with a stir bar was charged with 2f-BiB (0.6 g, 1.7 mmol), nBA (12.8 g, 0.1 mol), PMDETA (0.115 g, 0.665 mmol), and DMF (5.0 mL). The solution was bubbled with dry nitrogen for 1 hr. Then, CuBr (95 mg, 0.665 mmol) was added under nitrogen atmosphere. The flask was sealed, back-filled with nitrogen, purged for 5 minutes, and immersed in an oil bath thermostated at 65° C. The polymerization was stopped after 2 hrs when the monomer conversion reached 83 mol % (determined by $^1$H-NMR as above). The polymer solution was passed through a neutral aluminum oxide column and the unreacted monomers were evaporated by bubbling with nitrogen gas. The produced polymer (8 g, 1.25 mmol) was dissolved in 50 mL of DMA and transferred to a 100 mL flask. Potassium acrylate (0.8 g, 7.3 mmol) was added and the solution was stirred for 72 hrs at room temperature. The solution was filtered, diluted with DCM (50 mL), and then washed with DI water (3×100 mL). The macromonomer solution was dried by adding MgSO4 and then by overnight evaporation in air.

(iv) Synthesis of Monomethacrylamidopropyl-Terminated Poly(Dimethylsiloxane)

MCR-A12 (40 g, 20 mmol), anhydrous DCM (100 mL), and TEA (3.5 mL) were added to a 250 mL round-bottom flask under nitrogen. The reaction mixture was cooled using an ice bath, then injected with MMAC1 (2.3 g diluted with 3 mL DCM) over a 30 minute period. Next, the reaction mixture was allowed to reach room temperature and stirred overnight. The filtrate was washed with dilute sodium hydroxide solution ($H_2O_2$, 0.2 M, 3×150 mL) then by DI water (3×150 mL). The mixture was dried by adding MgSO4, passed through a basic alumina column, and stored in a freezer at −20° C.

(v) Synthesis of Poly(Dimethylsiloxane) Bottlebrushes

A 25 mL Schlenk flask equipped with a stir bar was charged with EBiB (2.4 mg, 12.5 µmol), MCR-M11 (15.0 g, 15.0 mmol), $Me_6TREN$ (2.9 mg, 3.3 µL), and PX (12.0 mL). The solution was bubbled with dry nitrogen for 1 hr, then CuCl (1.2 mg, 0.012 mmol) was quickly added to the reaction mixture under nitrogen atmosphere. The flask was sealed, back-filled with nitrogen, purged for 5 minutes, and then immersed in an oil bath thermostated at 45° C. The polymerization was stopped after 12 hrs at 75% monomer conversion, resulting in a bottlebrush PDMS polymer with degree of polymerization (DP) of the backbone ($n_{bb}$)~900. The polymer was precipitated three times from DMF to purify, and dried under vacuum at room temperature until a constant mass was reached. The AFM images, molecular weight, and PDI measurements of the product are shown in Table 1.

(VII) Bottlebrush PBA Elastomer Films

All bottlebrush PBA elastomers were prepared by one-step polymerization of monoacrylate-terminated poly(n-$BA_{16}$) macromonomer (2000 g/mol, DP=16) with different molar ratios of poly(n-$BA_{50}$) macro cross-linker (6400 g/mol, DP=50). The initial reaction mixtures contained: 56 wt % monomer, 1.5 wt % BAPOs photoinitiator, and 42.5 wt % anisole as solvent. Exact amounts of poly(n-$BA_{50}$) macro cross-linker ([poly(n-$BA_{50}$)-cross-linker]/[poly(n-$BA_{16}$)-monomer]=0.00125, 0.0025, 0.005, 0.0075, 0.01) were added to the mixtures and degassed by nitrogen bubbling for 30 minutes. The mixtures were molded, cured, and washed in a manner similar to that described above.

(VIII) Comb-Like Elastomer Films and Melts nBA and poly(n-$BA_{16}$) with different molar ratios (n-BA/poly(n-$BA_{16}$)=2, 4, 8, 16, 32, 64) were mixed in 20 mL flasks. Anisole solvent was added to the mixtures to give a solvent-to-monomer mass ratio of 0.75. BAPOs (2.5 wt % of monomer) photoinitiator and exact amounts of poly(n-$BA_{50}$) macro cross-linker ([poly(n-$BA_{50}$) macro cross-linker]/[poly(n-$BA_{16}$)-monomer]=0.00125, 0.0025, 0.005, 0.0075, 0.01) were added to the mixtures, which were then degassed by nitrogen bubbling for 30 minutes. The mixtures were molded, cured, and washed in a manner similar to that described elsewhere herein.

For synthesis comb polymer melt for determination of grafting distribution through polymer strand in different conversion and final conversion, nBA and poly(n-$BA_{16}$) with different molar ratios (n-BA/poly(n-$BA_{16}$)=2, 4, 8, 16, 32, 64) were mixed in 20 mL air free flasks. Anisole solvent was added to the mixtures to give a solvent-to-monomer mass ratio of 0.75. BAPOs (2.5 wt % of monomer) photoinitiator were added to the mixtures, which were then degassed by nitrogen bubbling for 30 minutes in a dark

TABLE 1

| Sample | $n_{bb}$ (NMR)[a] | $n_{bb}$ (AFM)[b] | $M_n$ (g/mol) | $M_w$ (g/mol) | Đ (AFM)[b] |
|---|---|---|---|---|---|
| PDMS-600 | 600 | 585 ± 40 | 585000 | 680000 | 1.16 |
| PDMS-900 | 900 | 902 ± 70 | 902000 | 1061000 | 1.18 |
| PDMS-1200 | 1200 | 11.63 ± 90 | 1163000 | 1267000 | 1.08 |
| PDMS-1500 | 1500 | 1315 ± 100 | 1315000 | 1494000 | 1.14 |

[a] Number average degree of polymerization of bottlebrush backbone ($n_{bb}$) determined by $^1$H NMR;
[b] $n_{bb}$ and dispersity of bottlebrush backbone determined by AFM as $n_{bb} = L_n/l_0$, where $L_n$ is number average contour length and $l_0 = 0.25$ nm is the length of the monomeric unit. In-house software was used to measure the contour length. Typically, 300 molecule ensembles were analyzed to ensure standard deviation of the mean below 10%.

(VI) Bottlebrush PDMS Elastomer Films

All bottlebrush elastomers were prepared by one-step polymerization of MCR-M11 (1000 g/mol, and MCR-M12 (2000 g/mol) with different molar ratios of cross-linker (DMS-R18 and DMS-R22 for Ml 1 and M12, respectively). The initial reaction mixtures contained: 56 wt % monomers (Ml 1 or M12), 1.5 wt % BAPOs photoinitiator, and 42.5 wt % PX as solvent. First, the mixtures were degassed by nitrogen bubbling for 30 minutes. Then, to prepare films, the mixtures were injected between two glass plates with a 2.3 mm PDMS spacer and polymerized at room temperature for 12 hrs under $N_2$ using a UV cross-linking chamber (365 nm UV lamp, 0.1 mW/$cm^{-2}$, 10 cm distance). Films were washed with chloroform (2× with enough to immerse and fully swell the films, each time for 8 hrs) in glass Petri dishes. The samples were then deswelled with ethanol and dried in a 50° C. oven. The conversion of monomers to elastomers (gel fraction) was between 90 to 98 wt % in every case.

chamber. The mixtures were moved and exposed to the UV light and samples were taken every 15 minutes and conversion and the ratio of unreacted monomers were measured by $^1$H-NMR. These experiments showed that (i) the grafting density along the comb-like network strands is uniform, (ii) conversion of monomers is >95%, and (iii) there are practically no unreacted monomers in the final product.

(IX) Linear-Bottlebrush-Linear (L-BB-L) Plastomer Film Preparation

To prepare L-B-L block copolymers, bottlebrush bifunctional macroinitiators with DP=300, 600, 900, 1200, 1800 were synthesized in a manner similar to that described in above, but with bifunctional ATRP initiator (2f-BiB) instead. The products were washed to remove unreacted monomers and passed through neutral aluminum oxide columns to remove residual catalyst. Then the PDMS bottlebrushes were used as bottlebrush ATRP initiators to grow side-blocks (e.g., PMMA) at both ends. The compositions of L-BB-L copolymers in the reaction flasks were measured by $^1$H-NMR and the samples were quenched when the mass ratio of linear-to-bottlebrush in the L-BB-L copolymer reached 4, 8, 16, and 32%. The products were diluted with DCM, passed through neutral aluminum oxide columns, and vacuumed overnight to remove unreacted monomers. Finally, the degree of polymerization of MMA at the both side of PDMS bottlebrush and mass ratio between bottle brush block and linear blocks were measured by $^1$H-NMR (CDCl$_3$, Bruker 400 MHz spectrometer) experiment for pMMAL-PDMSB.B-pMMAL (L$_{180}$-B.B$_{900}$-L$_{180}$). The dried samples were dissolved in chloroform and poured into Teflon petri-dishes (2 inches diameter). The dishes were placed in the hood overnight then in an oven at 50° C. for 2 hrs to dry. The samples were gently removed from the dishes and punched to prepare dog bone samples for mechanical property measurements.

(x) Uniaxial Tensile Stress Strain Measurements

Dog bone-shaped samples with bridge dimensions of 12 mm×2 mm×1 mm were loaded into an RSA-G2 DMA (TA Instruments) and subjected to uniaxial extension at a constant strain rate of 0.003 s$^{-1}$ and temperature of 20° C. To measure elongation-at-break (FIG. 20A-F), the samples were stretched until rupture occurred. To verify elasticity, the samples were subjected to repeated loading-unloading cycles. In each case, tests were conducted in triplicate to ensure accuracy of the data. Measurement errors are calculated by taking the standard deviation of the mean of values from three separate experiments. All figures in the main text show dependence of the true stress on the elongation (deformation) ratio $\lambda$. The elongation ratio $\lambda$ for uniaxial network deformation is defined as the ratio of the sample's instantaneous size L to its initial size L$_0$, $k=L/L_0$.

(XI) Elasticity and Viscoelasticity of Bottlebrush Elastomers

The highly elastic nature of brush-like architectures is described: a bottlebrush ($n_{sc}=14$, $n_x=200$, $n_g=1$) elastomer displays (i) fully reversible deformation and (ii) no sign of hysteresis after five cyclical deformations to 100% strain. The strain rate of 0.003 s$^{-1}$ corresponds to the elastic regime, which is validated by measuring the frequency spectra of the storage modulus. The displayed experimental master curves for a PDMS bottlebrush elastomer with $n_x=100$ were measured from 0.1 to 100 rad/s over temperatures ranging from 153 to 303 K and strains ranging from 0.1 to 5% (ARES-G2 rheometer, TA Instruments). Multiple measurements at different strains at a single temperature were performed to ensure a linear response. Using the Williams-Landel-Ferry (WLF) equation, the time-temperature superposition principle was used to construct the master curves with a reference temperature of 298 K. The samples display constant modulus in a wide range of frequencies, leading to strain rate independent properties at effective strain rates up to 0.8 s$^{-1}$. Following the terminal plateaus, the materials move through a series of relaxation transitions that were ascribed to a crossover from Rouse-like relaxations of thick brush filaments to the relaxations of individual linear chain segments (Daniel et al. (2016) *Nature Materials* 15: 183; Cao et al. (2016) *Macromolecules* 49: 8009).

Dynamics of bottlebrush networks in relation to their static properties was discussed elsewhere (Cao et al. (2016) *Macromolecules* 49: 8009). Here, it is important to point out that the value of the shear modulus in the low frequency plateau regime for $n_x=100$ is consistent with the value of the shear modulus obtained in the linear deformation regime. See FIG. 22.

b. Biological Tissues Used for Synthetic Mimics

In mapping the networks' elastic properties onto the strands' chemical structures specific values for the Kuhn length, bond length, or monomer excluded volume were not used. These parameters always enter the scaling equations in dimensionless combinations and are thus absorbed into numerical constants. These constants define the correlations between modulus E, parameters $\alpha$ and $\beta$, and the structural [$n_{sc}$, $n_g$, $n_x$] triplet for the particular (in terms of chemical structure) polymer library (see discussion of mapping procedure).

c. Mimicking Mechanical Behavior of Biological Materials

Biological materials display highly diverse combinations of mechanical properties: bone, for example, is rigid and brittle, while jellyfish are soft and elastic. Moreover, these combinations tend to deviate from the general trend for synthetic materials, whereby more rigid materials are less deformable. Specifically, for synthetic materials, larger values of the Young's elastic modulus, E, lead to lower values of extensibility (or 'elongation-at-break'), $\lambda_{max}$. Conventional linear-chain elastomers illustrate the ubiquity of this relationship. Here, the degree of polymerization of the network strand of elastomers ($n_x$) single-handedly determines both $E \sim n_x^{-1}$ and $\lambda_{max} \sim \sqrt{n_x}$ (see equations 1.1 and 1.2), resulting in a universal relationship, $E \sim \gamma_{max}^{-2}$, that confines the mechanical behavior of the vast majority of elastomeric materials to a single trend line, with a lower bound imposed by chain entanglements (Daniel et al. (2016) *Nat. Mater.* 15: 183; Patel et al. (1992) *Macromolecules* 25: 5241). Biological materials, by contrast, occupy a rich parameter space beneath this line that is apparently inaccessible to the linear-chain elastomers (Chen et al. (2013) *Prog. Polym. Sci.* 38: 584).

The possibility of accessing this untapped space of mechanical properties was first suggested when polymeric side chains were grafted onto linear backbones (Fetters et al. (2002) *Macromolecules* 35: 10096; Pakula et al. (2006) *Polymer* 47: 7198); this facilitated chain disentanglement in polymer melts (Daniel et al. (2016) *Macromolecules* 25: 5241; Daniels et al. (2001) *Macromolecules* 34: 7025; Kapnistos et al. (2005) *Macromolecules* 38: 7852) and unveiled the promise of brush-like architecture for making advanced elastomers (Vatankhah-Varnoosfaderani et al. (2017) *Adv. Mater.* 29: 1604209; Daniel et al. (2017) *Macromolecules* 50: 2103), thermoplastics (Zhang et al. (2016) *Macromolecules* 49: 9108), and molecular assemblies (Xia et al. (2009) *J. Am. Chem. Soc.* 131: 18525; Bolton and Rzayev (2014) *Macromolecules* 47: 2864). Unlike linear-chain networks, brush-like networks are defined by three independent structural parameters—the degrees of polymerization of the side chains ($n_{sc}$), of the spacer between neighboring side chains ($n_g$), and of the strand backbone ($n_x$). This transforms the one-dimensional parameter space of synthetic elastomers ($E \sim \lambda_{max}^{-2}$) into a multidimensional landscape of accessible E versus $\lambda$max correlations. In order to map this space, libraries of brush-like poly(dimethylsiloxane) (PDMS) and poly(n-butyl acrylate) (PBA) elastomers were synthesized with accurately controlled sets of [$n_{sc}$, $n_g$, $n_x$] parameters. Mechanical testing was then carried out in combination with analytical, calculations to characterize network equilibrium stress-strain behaviors for broad strain ranges, delineating correlations between triplet [$n_{sc}$, $n_g$, $n_x$] combinations and mechanical properties. Finally, these correlations were used to establish rules for selecting an appropriate [$n_{sc}$, $n_g$, $n_x$] triplet in order to specify, in a programmable fashion, the synthetic replication of any stress-strain curve in the "biological triangle".

Tensile tests of the PDMS and PBA libraries revealed four distinct correlations between E and $\lambda_{max}$. The arrows signify: (i) a conventional decrease in E as $\lambda_{max}$ increases; (ii) a unique concurrent increase in E and $\lambda_{max}$; (iii) variations in E at a constant $\lambda_{max}$; and (iv) variations in $\lambda_{max}$ at a constant E (shown in FIG. 20A-D, respectively). These correlations represent the possibility of controlling network architecture to achieve orders-of-magnitude variations in Young's modulus (from $10^1$ to $10^9$ Pa), elongation-at-break (from 1 to 100), and strain stiffening ($E^{-1} \partial\sigma/\partial\lambda \approx 1$–103) in solvent-free and single-component elastomers. Close agreement between the theoretically predicted and experimentally measured correlations (FIG. 20E) indicates narrow and uniform distributions of network mesh dimensions across the samples, and thereby validates the correlations. The ability of brush-like elastomers to regulate E and $\lambda_{max}$ independently (that is, to realize nearly any [E, $\lambda$max]pair) can be seen by plotting $E\lambda_{max}^2$ versus $n_g$ (FIG. 20F). Indeed, brush-like systems (exemplified here by PDMS networks with $n_{sc}$ values of 14) unfold the single point of linear-chain elastomers (where $E\lambda_{max}^2$ is constant) into a $E\lambda_{max}^2$ line defined by the independent control of the side-chain grafting density.

Figure 20B:
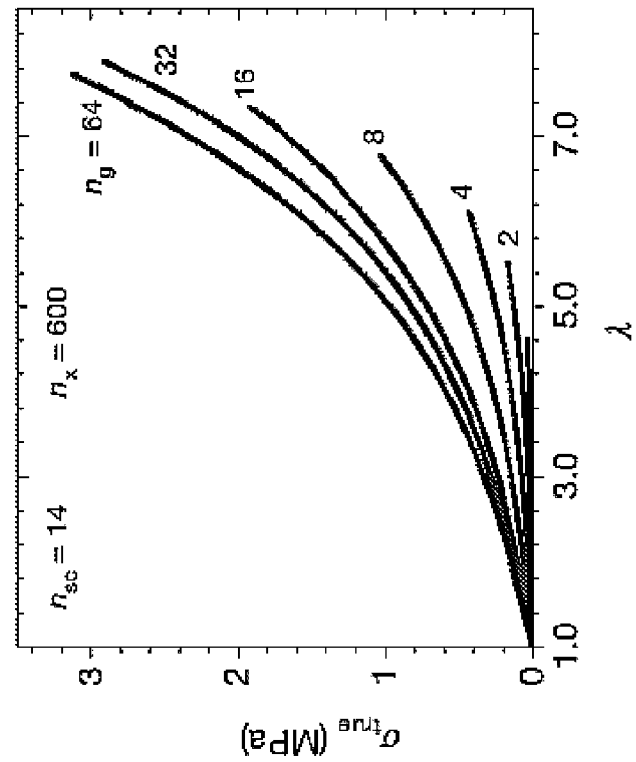
FIG. 20A-F show representative diagrams illustrating the mechanical diversity of the brush- and comb-like elastomer library.
Figure 20A:
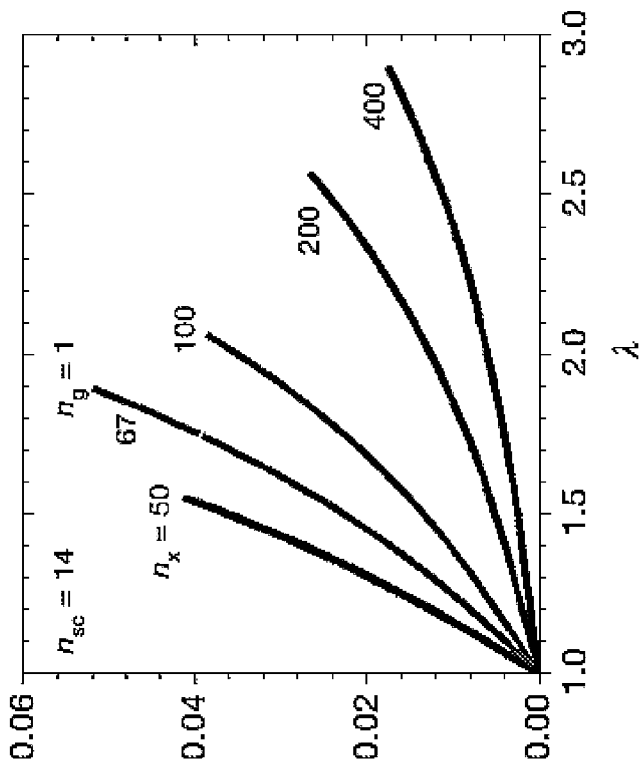
Figure 20C:
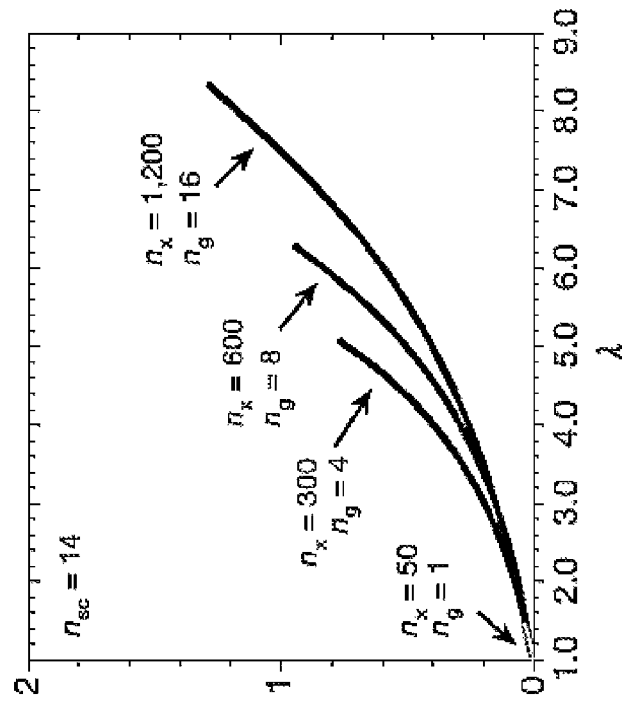
Figure 20D:
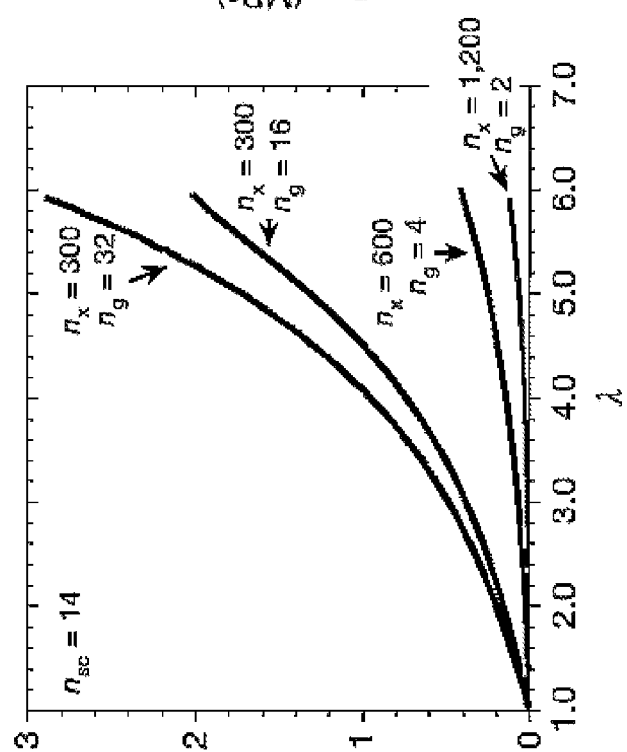
Figure 20F:
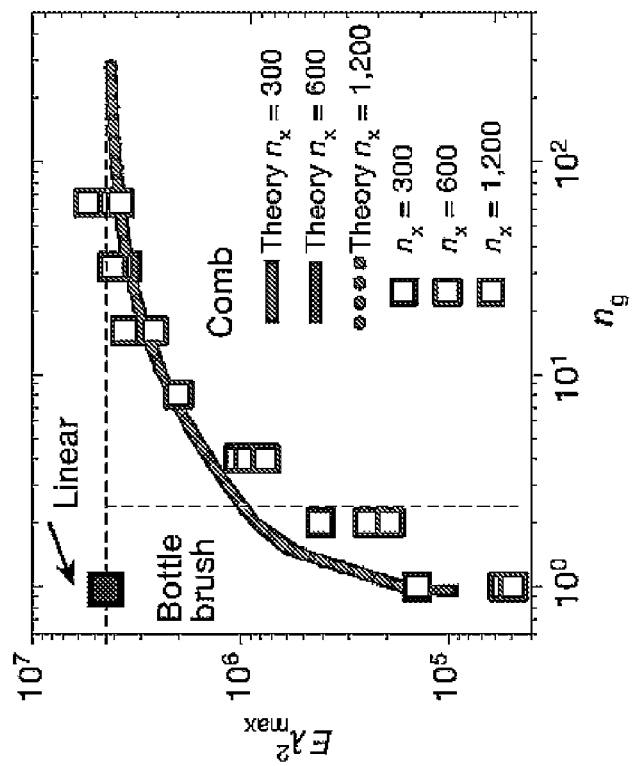

Referring to FIG. 20A-D, tensile testing (measuring true stress, $\sigma_{true}$, versus uniaxial elongation, $\lambda$) of brush-like PDMS elastomers that are defined by different [$n_{sc}$, $n_g$, $n_x$] triplets demonstrates the mechanical diversity of the brush- and comb-like elastomer library. When the strand length ($n_x$) is varied, E and $\lambda_{max}$ show conventional inverse variation (FIG. 20A). When the grafting density ($n_g$) is varied, E and $\lambda_{max}$ increase simultaneously (FIG. 20B). When both strand length and grafting density are varied, E varies but $\lambda_{max}$ remains constant (FIG. 20C), or $\lambda_{max}$ varies but E remains constant (FIG. 20D). These curves were generated as described above, and represent the average of at least three measurements, which showed excellent reproducibility with a relative standard deviation of less than 5%.

Figure 20E:
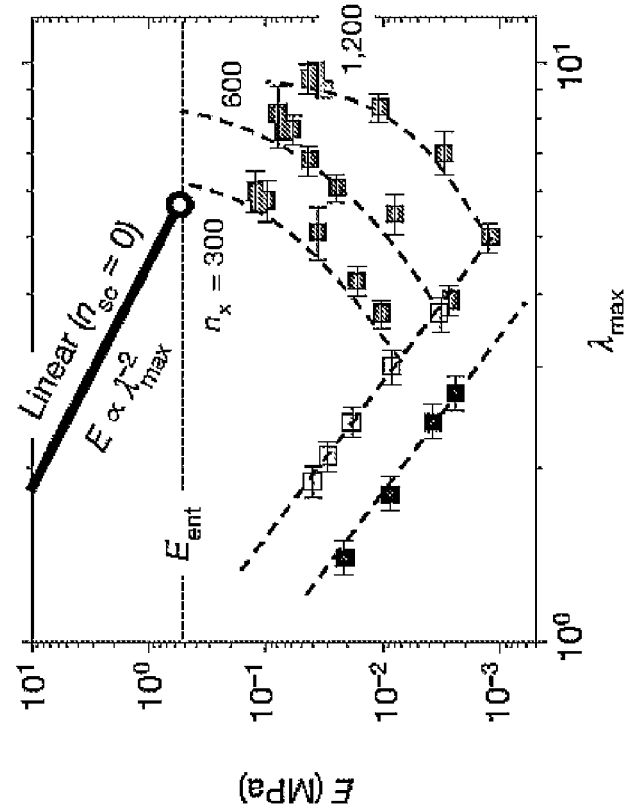

Referring to FIG. 20E, combined E versus $\lambda_{max}$ plots for comb and bottlebrush elastomers are shown. Dashed lines represent theoretical predictions. Squares denote experimental results; error bars show the standard deviation (s.d.) of the mean $\lambda_{max}$; s.d. values for E fall within the squares. The horizontal dotted line corresponds to the entanglement plateau modulus, $E_{ent}$, of conventional linear-chain melts.

Referring to FIG. 20F, universal $E\lambda_{max}^2$ versus $n_g$ correlations are shown. Varying $n_g$ alone allows, first, a crossover between the bottlebrush and comb regimes (vertical dashed line); and second, an upper entanglement plateau (horizontal dashed line). For linear-chain elastomers of variable $n_x$, $E\lambda_{max}^2$ is a constant (black square). The higher-dimensional nature of brush-like architectures relative to linear-chain elastomers produces close agreement between experiment and theory. Values on the y-axis were multiplied by a factor of 0.52 to account for chemical composition.

Using this variability in the mechanical properties of brush-like elastomer networks, synthetic materials that replicate the mechanical performance of select biological tissues were "reverse engineered." Without wishing to be bound by theory, it is noted that these materials mimic only the mechanical properties of their biological counterparts, and are not meant to be biologically compatible; however, this approach could be applied to biocompatible chemistries. The first step in the replication process is fitting the tissue-deformation curve to:

$$\sigma_{true}(\lambda) = \frac{E}{9}(\lambda^2 - \lambda^{-1})\left[1 + 2\left(1 - \frac{\beta(\lambda^2 + 2\lambda^{-1})}{3}\right)^{-2}\right] \quad (1)$$

where $\beta$ (the strand-extension ratio) and E (here, the structural Young's modulus) are fitting parameters, and $\sigma_{true}$ is the true stress. This equation serves as a constitutive fitting equation for all equilibrium network deformations and has been validated for a broad range of unentangled networks, including synthetic elastomers and biological gels (Carrillo et al. (2013) *Macromolecules* 46: 3679). The next step is to map these decoded macroscopic fitting parameters into the molecular model of brush-like elastomers, defined in terms of the architectural triplet. The strand-extension ratio, defined as $$\mu \equiv <R^2_{in}>/R^2_{max},$$

is the ratio of the mean square end-to-end distance of undeformed network strands, $R_{in}^2$, to the square of the contour length of a fully extended strand, $R_{max}$, which equals $n_x l$, in as-prepared elastomers (where l is the length of the monomeric unit of the brush backbone). By considering brush-like strands as semiflexible polymers, $\beta$ can be expressed in terms of $$\alpha^{-1} \equiv R_{max}/b_K$$

(where $b_K$ is the number of Kuhn lengths per network strand), as:

$$\beta = \alpha\left(1 - \frac{\alpha}{2}\left(1 - \exp\left(-\frac{2}{\alpha}\right)\right)\right)$$

Parameters $\beta$ and $\alpha$ depend on [$n_{sc}$, $n_g$, $n_x$] and control strain stiffening of the network and strand stiffness respectively. Note that $\beta$ is directly related to the maximum network elongation as $$\lambda_{max} \cong R_{max}/<R^2_{in}>^{0.5} \approx \beta^{-0.5},$$

illustrating that less extensible networks are subject to rapid strain stiffening. The structural Young's modulus, which is proportional to the density of a stress-supporting network strands, represents the second half of the model and is expressed as:

$$E = C\frac{\beta\alpha^{-1}}{(1 + n_{sc}/n_g)}(n_x^{-1} - B)$$

where B and C are numerical coefficients that account for network chemical structure and topology. Network libraries (FIG. 20A-D) were used to verify and calibrate the scaling relationships between [E, $\beta$] and [$n_{sc}$, $n_g$, $n_x$]. Solving these relationships with the decoded triplet completes the second step of the design process and primes synthetic replication.

Figure 4:
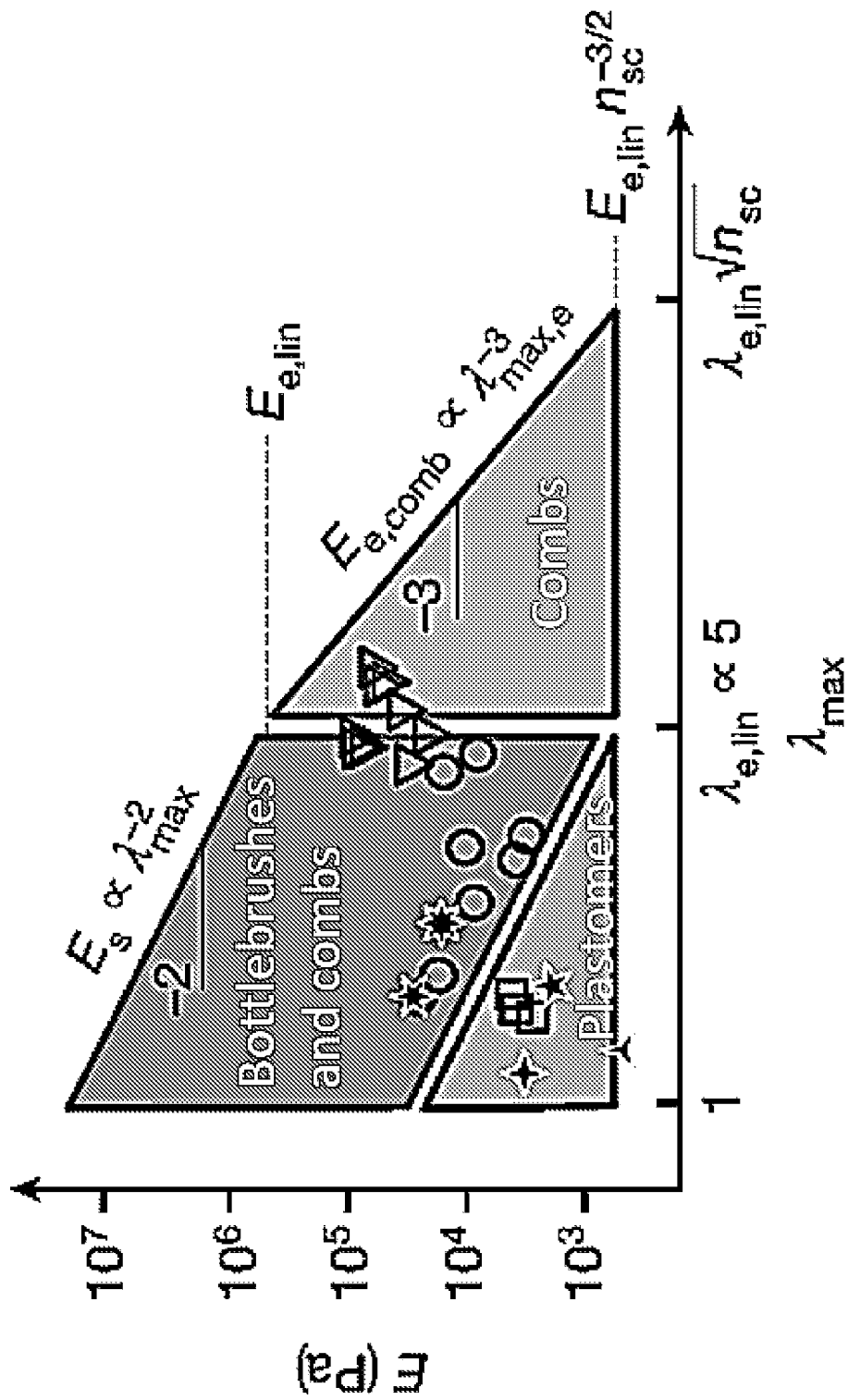
FIG. 4 shows a representative graph illustrating that the disclosed bottlebrushes, combs, and plastomers have mechanical properties of biological materials.
Figure 12B:
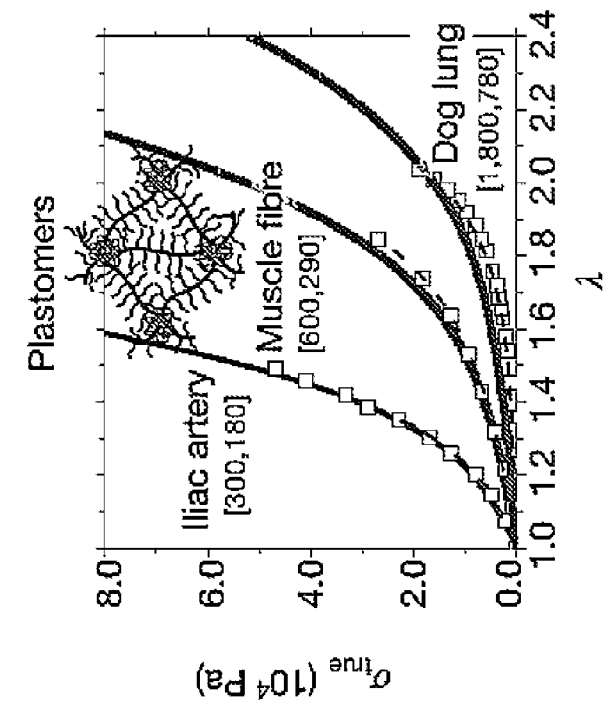
FIG. 12A and FIG. 12B show representative stress-strain data for alginate gel, jellyfish tissue, and poly(acrylamide-co-urethane gel) (FIG. 12A) or for iliac artery, muscle, and dog lung tissue (FIG. 12B).
Figure 12A:
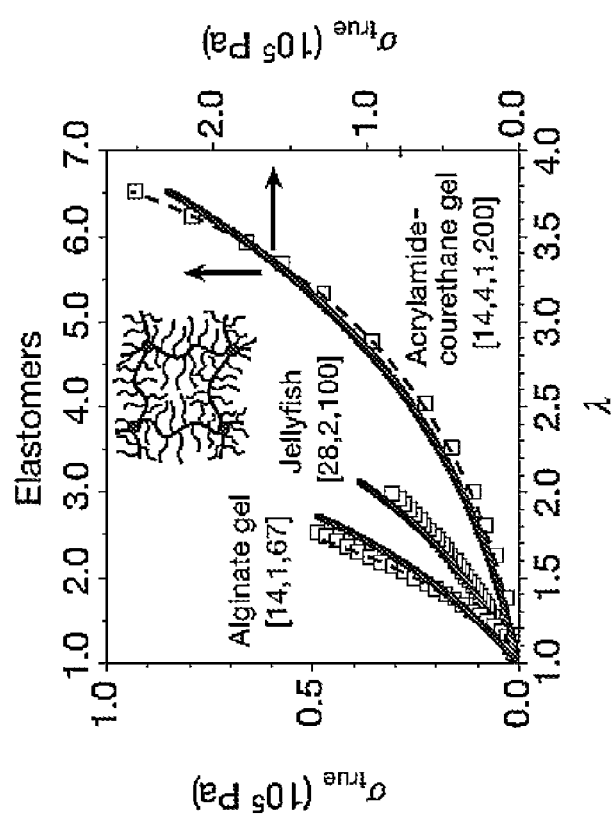

Applying this protocol to the synthesis of PDMS bottlebrushes, combs and plastomers (which combine properties of both elastomers and plastics), mechanical replicas of representative biological tissues were created (FIG. 4). FIG. 12A reveals successful mimicking of the stress-strain curves of alginate gel, jellyfish tissue and composite poly(acrylamide-co-urethane) gel, with [$n_{sc}$, $n_g$, $n_x$] combinations of [14, 1, 67], [28, 2, 100], and [14, 4, 1,200], respectively. Mimicking the composite gel is particularly important, in that it demonstrates the role a of comb-like elastomers in materials replication (FIG. 4). However, when turning to strain-adaptive biological tissues (such as arteries, muscles and lungs), either physically prohibitive or synthetically challenging [$n_{sc}$, $n_g$, $n_x$] combinations arose; for example, the triplet is [97, 1, 84] for arteries, [66, 1, 128] for muscle, and

[189, 1, 153] for lungs. These triplets reflect the combination of extreme softness and sharp strain stiffening that is characteristic of these biological tissues (FIG. 4). Mimicking such characteristics requires elastomers with simultaneously long and pre-extended network strands, which were obtained by synthesizing ABA copolymers, consisting of bottlebrush PDMS B-blocks and linear PMMA A-blocks. Like linear ABA systems (Gouinlock and Porter (1977) *Polym. Eng. Sci.* 17: 535; Takano et al. (2005) *Macromolecules* 38: 9718), linear-brush-linear copolymers form robust physical networks through strong segregation of the PMMA and PDMS blocks (Luo et al. (2015) *Macromolecules* 48: 3422). Aggregation of the linear tails in these triblock networks extends the middle blocks, which in turn extends the network strands (increasing ($R_{in}^2$)) and enhances strain stiffening (FIG. 12B). Specifically, by adding just 10-15 vol. % PMMA, a fourfold increase in strain stiffening was achieved relative to that in covalently crosslinked bottlebrush networks with the same Young's modulus ($\beta$ increased from around 0.1 to 0.4 for an E of about 5 kPa). Thus, using triblock copolymers with the same side-chain length ($n_{sc}$=14) but different lengths of the bottlebrush block ($n_{bb}$=300, 600 or 1800) enabled the synthesis of materials that mimic the mechanical properties of lung, muscle and artery tissues, respectively. Without wishing to be bound by theory, this addition of chemically dissimilar elements highlights how the fundamental architectural triplet can be expanded to mimic the mechanical complexity of biological tissues.

Referring to FIG. 4, PDMS bottlebrushes, combs, and plastomers with the mechanical properties of biological materials were synthesized. This graph shows these properties (squares, ABA copolymers; triangles, combs with ng>2; circles, bottlebrushes with $n_g$<2), along with the properties of brain (▲), arteries (✦), lungs (★), eye lens (✱) and jellyfish (✻). The $\lambda_{max}$ boundaries correspond to the elongations-at-break of conventional linear-chain networks ($\lambda_{e,lin} \approx 5$) and comb-like networks ($\lambda_{e,lin} \sqrt{n_{sc}}$) that result from entanglements of the network strands. The E boundaries correspond to the entanglement plateau moduli of linear chain ($E_{e,lin}$) and comb-like chain ($E_{e,lin} n_{sc}^{-3/2}$) melts. The diagonal boundaries are provided by inverse E and $\lambda_{max}$ relationships of linear and comb-like networks, ~$\lambda_{max}^{-2}$ and E~$\lambda_{max}^{-3}$, respectively. The lower boundary of the parallelogram, $E\lambda_{max}^2$>$10^4$ Pa, corresponds to bottlebrush networks with long side chains of about 100 units.

Referring to FIG. 12A, shown are stress-strain data (squares) for alginate gel, jellyfish tissue and poly(acrylamide-co-urethane) gel, together with fitting analysis of the data using equation (1), and curves for PDMS bottlebrush and combs synthesized via fitting analysis with the indicated architectural [$n_{sc}$, $n_g$, $n_x$] triplets (blue lines).

Referring to FIG. 12B, shown are stress-strain data (squares) for iliac artery, muscle, and dog lung tissue, together with fitting results obtained using equation (1), and stress-strain curves from PMMA-PDMS-PMMA mimics (solid blue lines) with different degrees-of-polymerization of the PDMS bottlebrush backbone ($n_{bb}$) and PMMA linear chains (N) as indicated by [$n_{bb}$, N]. Each experimental curve in FIG. 12A and FIG. 12B represents the average of at least three measurements with a relative standard deviation of less than 5%.

Figure 21B:
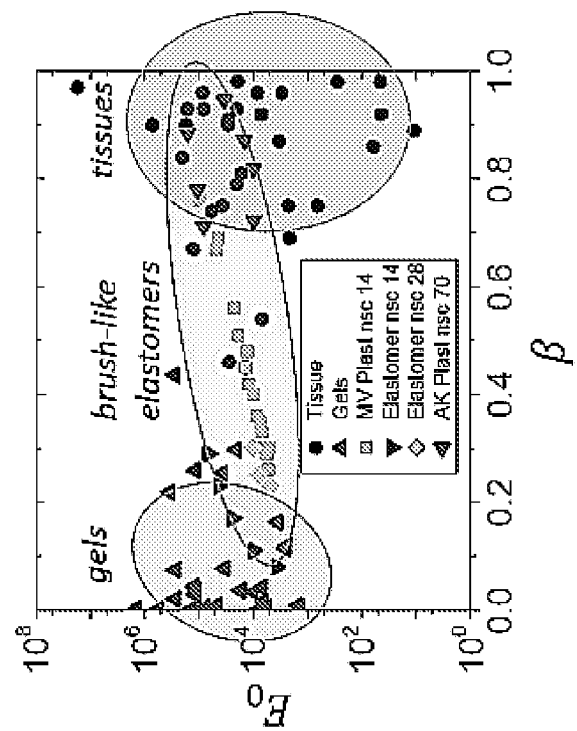
FIG. 21A and FIG. 21B show representative diagrams illustrating the ability of bottlebrush elastomers to mimic the mechanical diversity of polymeric gels and soft biological tissues.
Figure 21A:
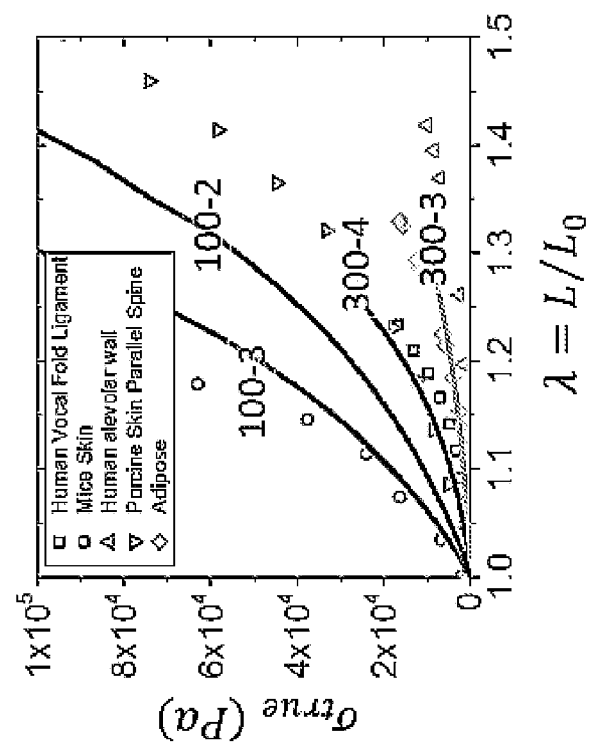

Referring to FIG. 21A, shown are stress-strain data for mice skin (circle), porcine skin (upper-pointed triangle), human vocal fold (square), adipose tissue (romb), and human alveolar wall (up-pointed triangle) together with synthetic replica of PMMA-PDMS-PMMA linear-bottle-brush-linear plastomers (all have PMDS side chains of degree of polymerization $n_{sc}$≅70) of different compositions as indicated: 100-3 ($n_{bb}$≅100 and $n_A$≅200, red line), 100-2 ($n_{bb}$≅100 and $n_A$≅150, blue line), 300-4 ($n_{bb}$≅300 and $n_A$≅800, black line), and 300-3 ($n_{bb}$≅300 and $n_A$≅300, green line).

Referring to FIG. 21A, shown are the Young's modulus ($E_0$) versus strain-stiffening parameter ($\beta$) diagram, which demonstrates the ability of brush-like elastomers (including covalently linked elastomers and physically linked plastomers) to precisely replicate both the Young's modulus values and strain-stiffening parameter values (encircled with an oval at the center of the diagram) of polymer gels (encircled with oval at the left hand-side) and soft biological tissues (encircled with oval at the right hand-side)

Two essential aspects of this replication process must be highlighted. First, numerous [$n_{sc}$, $n_g$, $n_x$] solutions might exist for a single [E, $\beta$] pair, because the number of unknowns in the model exceeds the number of equations. This plurality is advantageous, because it both allows synthetic flexibility and also offers scope for additional programming—for example, in the density of trapped entanglements (Carrillo et al. (2013) *Macromolecules* 46: 3679). Second, although dense bottlebrushes fill much of the E versus $\lambda_{max}$ space (FIG. 4, where $n_g$=1), their application is restricted in two cases: in the first case, high extensibilities are limited by network strand entanglements ($E\lambda_{max}$<$\lambda_{e,lin}$≅5); and in the second case, pairings of low modulus with low extensibility ($E\lambda_{max}$>$10^4$ Pa) are restrained by challenging combinations of short strands and long side chains ($n_x$<$n_{sc}$) (see equations 4.10 and 4.11; $\lambda_{e,lin}$ refers to the elongation-at-break of conventional linear-chain networks). The first constraint was alleviated by controlling grafting density (that is, by using combs where $n_g$>1), which expands the range of accessible extensibilities up to $\lambda_{max}$≈√($n_{sc}$) $\lambda_{e,lin}$≈50 for typical $\lambda_{e,lin}$ values of about 5 and $n_{sc}$ values of 100 (FIG. 4). Meanwhile, the second constraint was overcome by creating physical networks of triblock copolymers (FIG. 4).

Without wishing to be bound by theory, this design-by-architecture approach could lead to a configurable synthetic engine that is able, with iterative refinement, to encode stress-strain behavior within solvent-free elastomers of a required chemistry. Moreover, although the effects of chemical composition are secondary to the control of architectural properties, these effects might allow the mechanical properties to be fine-tuned—and become particularly vital when meeting application-specific needs such as biological compatibility, solubility and conductivity.

2. Experimental II—Design of Solvent-Free, Super-Soft Chromogenic Elastomers a. Synthesis and Characterization (i) Materials Methyl methacrylate (MMA, 99%) was obtained from Acros and purified using a basic alumina column to remove inhibitor. Monomethacryloxypropyl-terminated poly(dimethylsiloxane) (MCR-M11, average molar mass 1000 g/mol, degree polymerization (DP)=14, dispersity, D=1.15) was obtained from Gelest and purified using basic alumina columns to remove inhibitor. Benzyl Methacrylate (BzMA, 95%) was obtained from Sigma Aldrich and purified by passing through basic alumina columns to remove inhibitors. Copper(I) chloride (CuCl, >99.995%), copper(I) bromide (CuBr, 99.999%), tris[2-(dimethylamino)ethyl]amine (Me6TREN), ethylene bis(2-bromoisobutyrate) (2-BiB, 97%), tetrahydrofuran (THF), p-xylene (PX) and toluene were purchased from Sigma Aldrich and used as received.

(ii) Synthesis of Poly(Dimethylsiloxane) Bottlebrushes

A 100 mL Schlenk flask equipped with a stir bar was charged with 2-BiB (15 mg, 41.6 μmol), MCR-M11 (50.0 g, 50.0 mmol), Me6TREN (19.2 mg, 22.2 μL, 83.3 mol), and Toluene (45.0 mL). The solution was bubbled with dry nitrogen for 1.5 hr, then CuCl (8.3 mg, 83.3 μmol) was quickly added to the reaction mixture under nitrogen atmosphere. The flask was sealed, back-filled with nitrogen, purged for 15 minutes, and then immersed in a 45° C. oil bath. The polymerization was stopped after 12 hours at 74% monomer conversion (FIG. 17), resulting in a bottlebrush PDMS polymer with DP of the backbone ($n_{bb}$)~900. The polymer was precipitated three-five times from methanol to purify residual macromonomer and passed through neutral aluminum oxide columns to remove residual catalyst. The resulting purified polymer was dried under vacuum at room temperature until a constant mass was reached. Molecular weight and PDI measurements of the product are verified using AFM images shown in FIG. 18 and Table 2.

Figure 17:
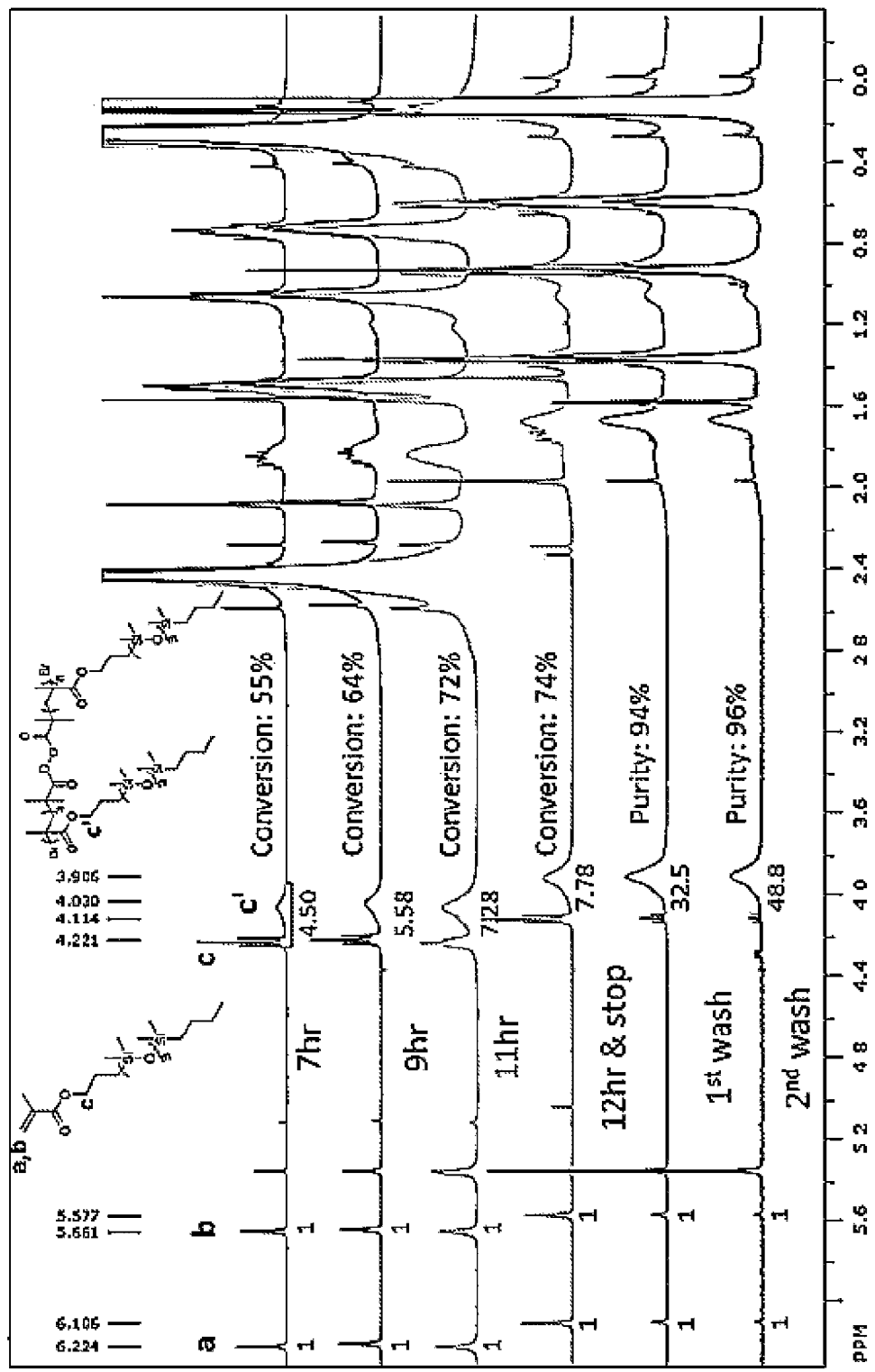
FIG. 17 shows a representative $^1$H NMR of poly(dimethylsiloxane) bottlebrushes at 55-74% conversion.

Referring to FIG. 17, $^1$H-NMRs of the corresponding reaction mixture at 55-74% conversion (400 MHz, CDCl3): 6.22, 5.66 ($CH_2$=$C(CH_3)C$=O, PDMS macromonomer, s, 2H), 4.22 (CO—$OCH_2$, PDMS macromonomer, t, 211), 3.96 (CO—$OCH_2$, reacted PDMS bottlebrush, m, 2H), conversion=[area(c+c')−area(2b)]/area(c+c')=74%. The last two NMRs show purification of un-reacted monomers after two washes.

Figure 18:
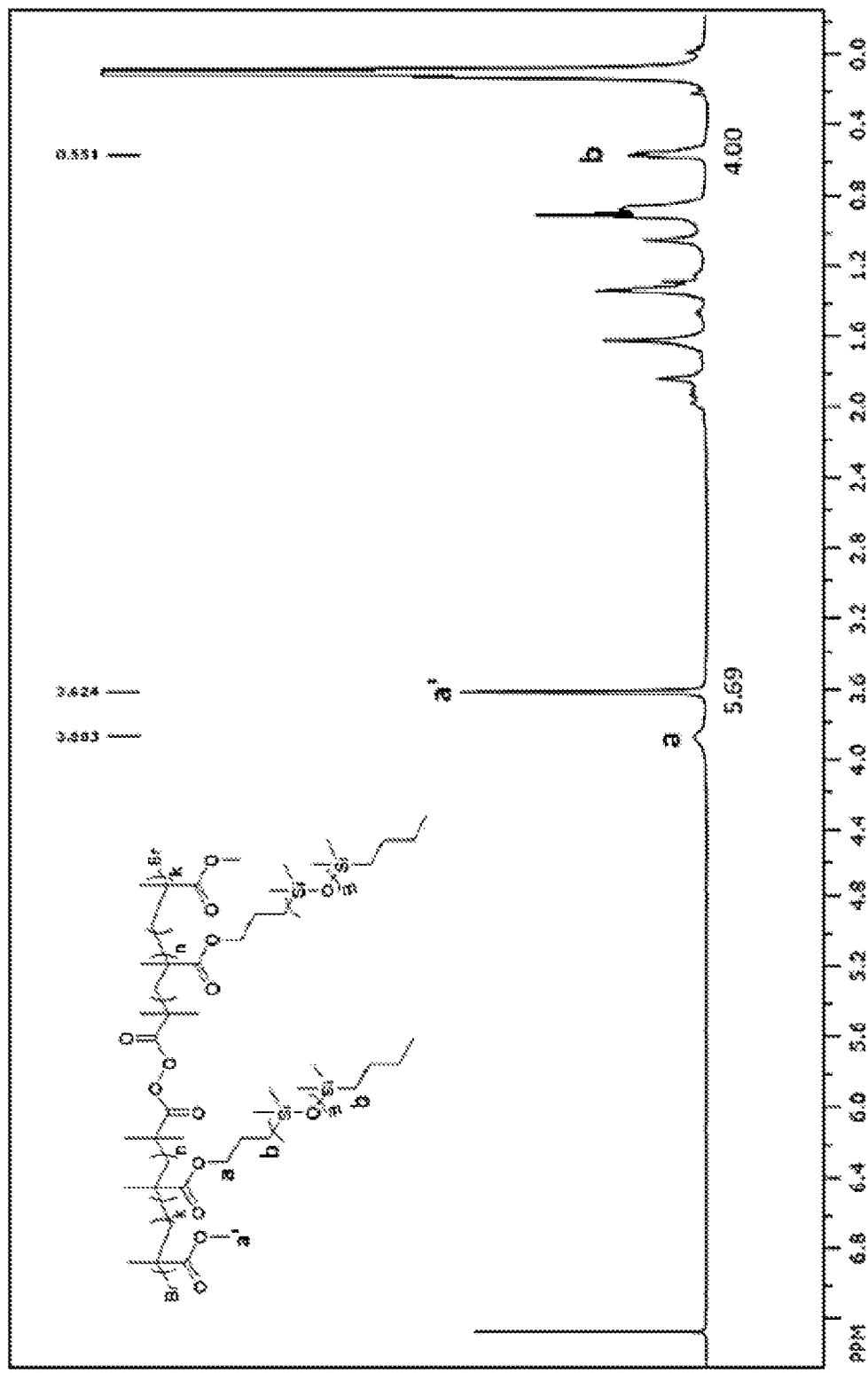
FIG. 18 shows a representative $^1$H NMR of PMMA-bbPDMS-PMMA.
Figure 19:
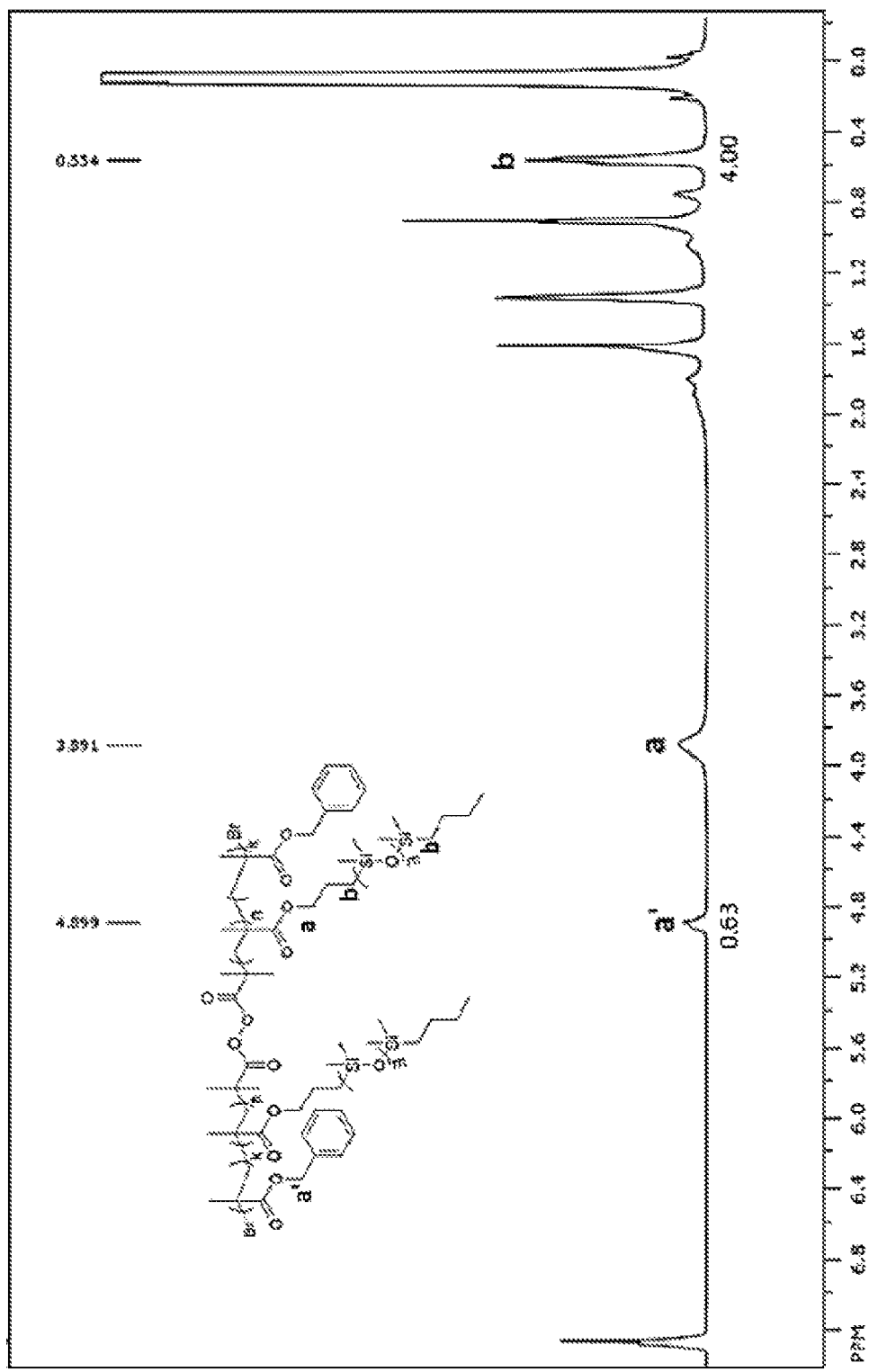
FIG. 19 shows a representative $^1$H NMR of PBzMA-bbPDMS-PBzMA.

(III) Linear-Bottlebrush-Linear (L-BB-L) Plastomer Synthesis and Film Preparation To prepare L-BB-L block copolymers, bottlebrush bifunctional macro-initiators were synthesized as described above. The resulting PDMS bottlebrushes were used as ATRP initiators to grow linear side-blocks (e.g., PMMA) at both ends. With a similar procedure as described above, equal weight macro-initiator, monomer, and $Me_6TREN$ were dissolved in toluene, degassed and followed with the addition of CuCl. The compositions of L-BB-L copolymers in the reaction flasks were measured by $^1$H-NMR and the samples were quenched with increasing linear-to-bottlebrush mass ratio as summarized in FIG. 23. The products were precipitated in methanol to remove unreacted monomers, dissolved in DCM to pass through neutral aluminum oxide columns, and vacuumed overnight. Finally, the DP and mass ratio of linear end bocks were measured by $^1$H-NMR (CDCl$_3$, Brüker 400 MHz spectrometer) as shown in FIG. 18 and FIG. 19 for PMMA-bbPDMS-PMMA and PBzMA-bbPDMS-PbzBA, respectively. Dried samples were dissolved in toluene and poured into Teflon petri-dishes (Welch Fluorocarbon) and left in the hood to dry for 3 days. The samples were gently removed from the dishes and punched to prepare samples for mechanical measurements. The M300-x samples in FIG. 13 were cast from tetrahydrofuran.

Referring to FIG. 18, the $^1$H-NMR of PMMA-bbPDMS-PMMA is shown. $\varphi_a$=0.13 (400 MHz, CDCl$_3$): 3.9 (—$CH_2$—O—C=O, br, 2H), 3.62 (COO—$CH_3$, s, 3H), 0.54 (COO—$CH_2$—$CH_2$—$CH_2$—$Si(CH_3)_2$, t, 4H). $DP_{MMA}$=Area (a'/3)/Area(b/4)*$DP_{PDMS}$.

Referring to FIG. 19, the $^1$H-NMR of PBzMA-bbPDMS-PBzMA is shown. $\varphi_a$=0.03 (400 MHz, CDCl$_3$): 4.89 (COO—$CH_2$-$C_6H_6$, s, 2H), 3.89 (COO—$CH_2$—$CH_2$—$CH_2$—$Si(CH_3)_2$, br, 2H), 0.55 (COO—$CH_2$—$CH_2$—$CH_2$—$Si(CH_3)_2$, t, 4H). $DP_{MMA}$=Area (a'2)/Area(b/4)*$DP_{PDMS}$.

b. Thermal Properties

Figure 11A:
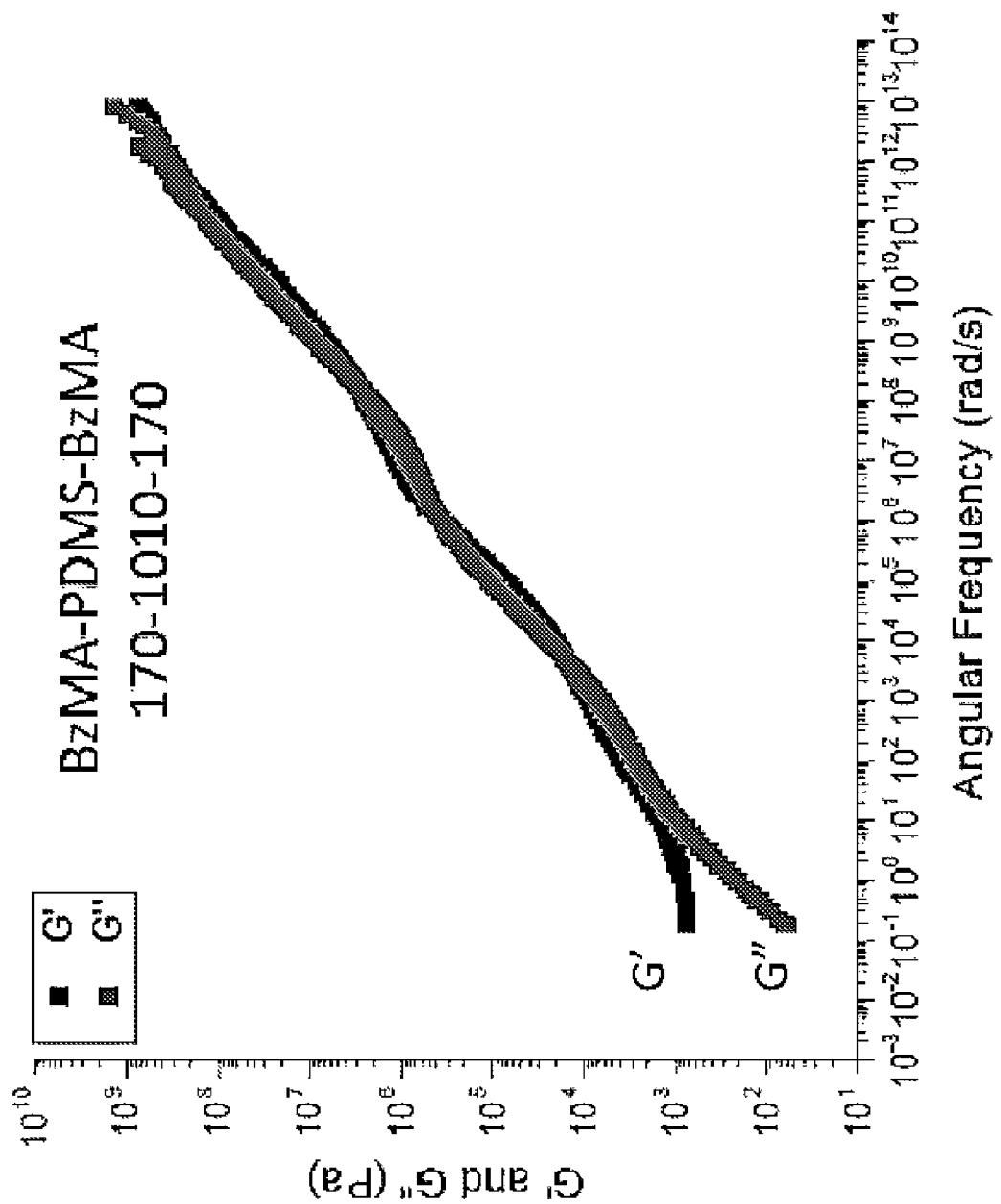
FIG. 11A shows representative master curves of storage and loss modulus as a function of frequency.

Referring to FIG. 11A, master curves at 25° C. of storage and loss modulus as a function of frequency the B1000-1 PBzMA-bbPDMS-PBzMA triblock-copolymer with $n_{sc}$=14, $n_{bb}$=1100, and $n_A$=170 (FIG. 23) were measured by oscillatory shear tests.

Figure 11B:
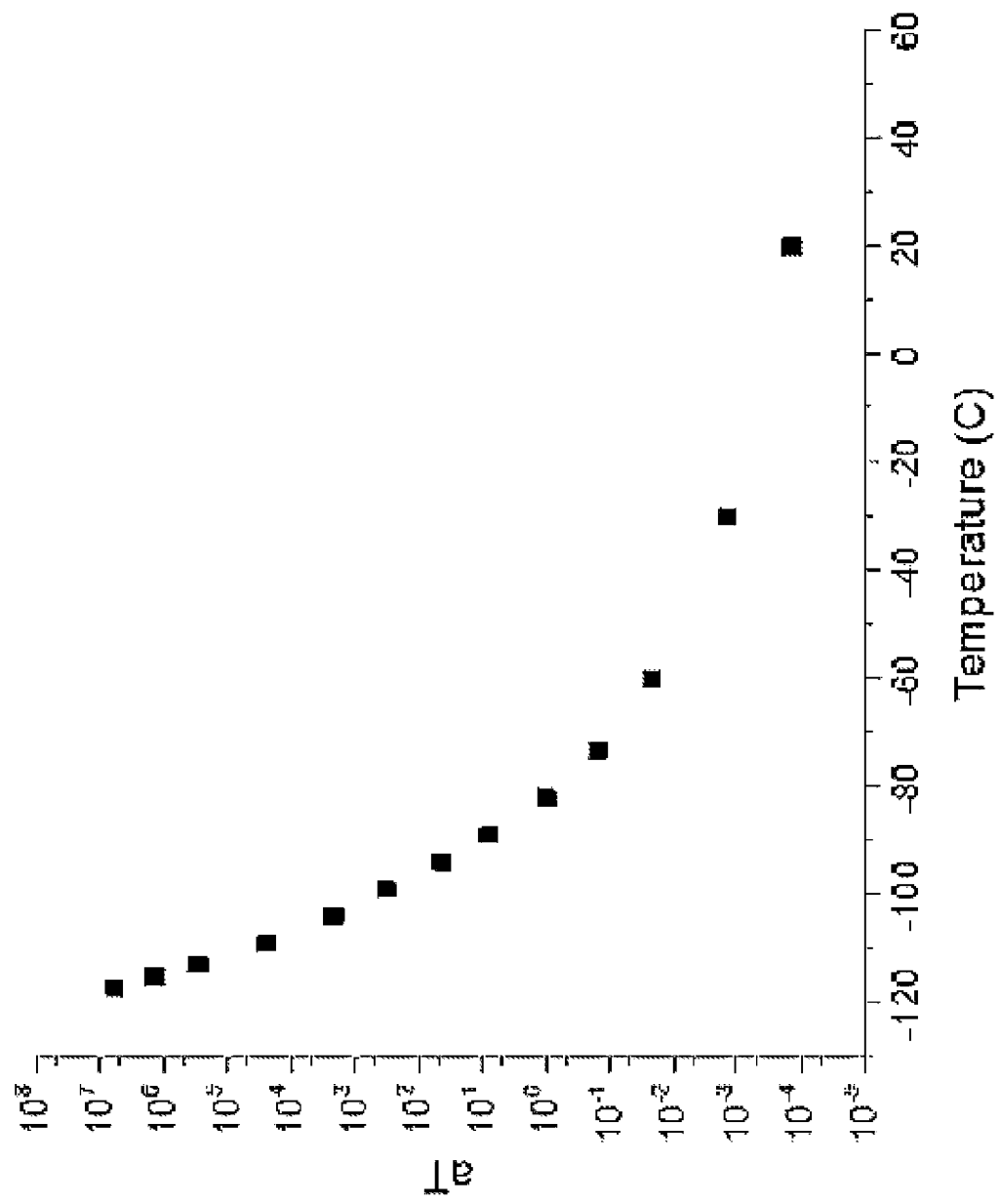
FIG. 11B shows representative time-temperature superposition shift factors used to construct the master curve in FIG. 11A.

Referring to FIG. 11B, time-temperature superposition shift factors were used to construct the master curve in FIG. 11A at reference of $T_{ref}$=$T_g$+150K (298K).

c. Atomic Force Microscopy

The imaging was performed in PeakForce QNM mode using a multimode AFM (Bruker) with a NanoScope V controller and silicon probes (resonance frequency of 50-90 Hz and spring constant of ~0.4 N/m).

The molecular characterization of PDMS bottlebrushes is shown in Table 2 below.

TABLE 2

| Sample | $n_{bb}$ (NMR)[1] | $n_{bb}$ (AFM)[2] | $M_n$ (g/mol) | $M_w$ (g/mol) | Đ (AFM)[2] |
|---|---|---|---|---|---|
| PDMS-600 | 602 | 585 ± 40 | 585000 | 680000 | 1.16 |
| PDMS-900 | 938 | 902 ± 70 | 902000 | 1061000 | 1.18 |
| PDMS-1200 | 1065 | 1163 ± 90 | 1163000 | 1267000 | 1.08 |

[1]Number average degree of polymerization of bottlebrush backbone (nbb determined by $^1$H NMR;
[2] $n_{bb}$ and dispersity of bottlebrush backbone determined by AFM (FIG. 18) as $n_{bb}$ = $L_n/l_0$, where $L_n$ is number average contour length and $l_0$ = 0.25 nm is the length of the monomeric unit. Contour length is measured via in-house software. Typically, 300 molecule ensembles were analyzed to ensure standard deviation of the mean below 10%.

d. Mechanical Properties (i) Uniaxial Tensile Stress Strain Measurements

Dog bone-shaped samples with bridge dimensions of 12 mm×2 mm×1 mm were loaded into an RSA-G2 DMA (TA Instruments) and subjected to uniaxial extension at 25° C. and constant strain rate of 0.005 s$^{-1}$, which is in the elastic regime. Samples were stretched until rupture, revealing the entire mechanical profile (FIG. 6-34). In each case, tests were conducted in triplicate to ensure accuracy of the data. Stress strain curves were fitted in accordance with fitting procedures and are displayed in FIG. 23. To verify elasticity of deformation, the samples were subjected to repeated loading-unloading cycles (FIG. 10A and FIG. 10B). All stress-strain curves show dependence of the true stress σ on the elongation (deformation) ratio λ shown in eq. S6.18 at small and intermediate deformation range but switch to a linear scaling with λ at the later stages of deformation. The elongation ratio λ for uniaxial network deformation is defined as the ratio of the sample's instantaneous size L to its initial size $L_0$, λ=$L/L_0$.

Referring to FIG. 6A-F, stress-strain curves (left) and corresponding differential modulus curves (right) of multiple PMMA-bbPDMS-PMMA series are shown. Different degrees of polymerization of the PDMS bottlebrush backbone and volume factions of PMMA linear chains are as indicated (FIG. 23). The samples (thin films) were cast from toluene.

Figure 9:
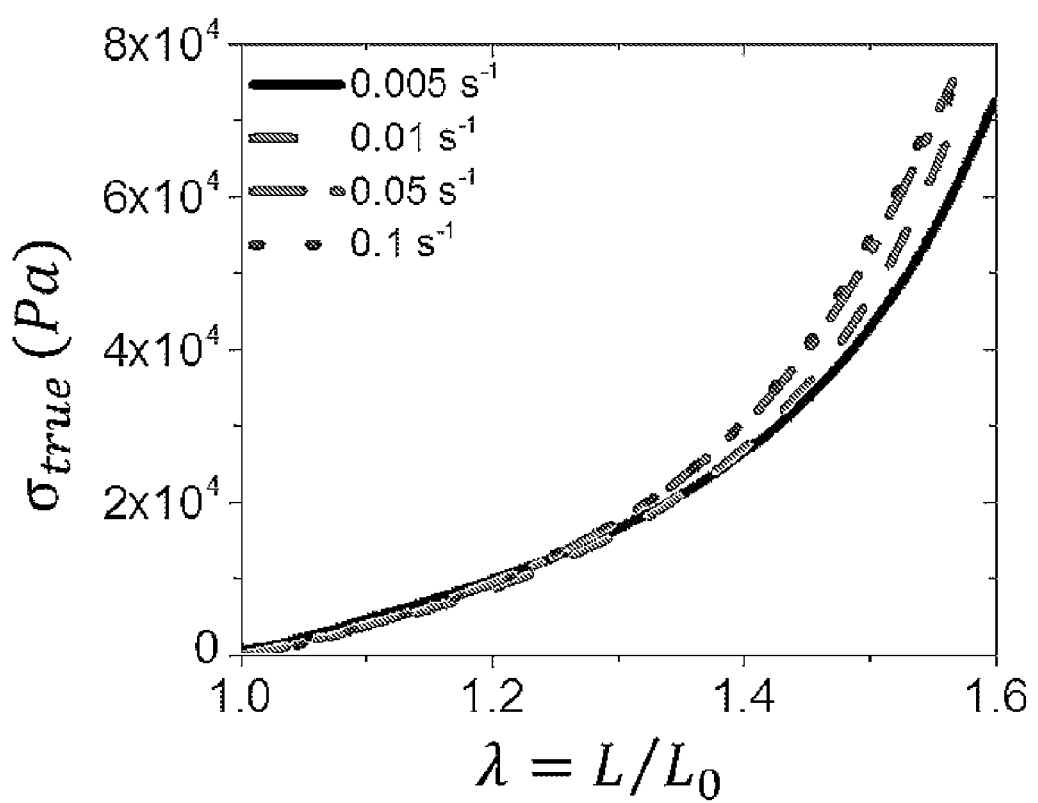
FIG. 9 shows representative data illustrating the strain rate dependence of the mechanical properties for M300-4 (see FIG. 23).
Figure 10B:
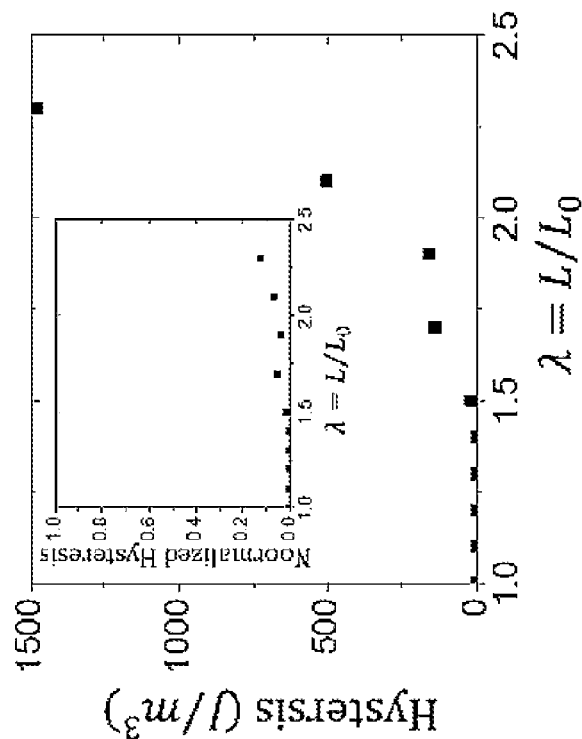
FIG. 10B shows representative data illustrating hysteresis energy as a function of elongation for the corresponding stress-strain cycles from FIG. 10A.
Figure 10A:
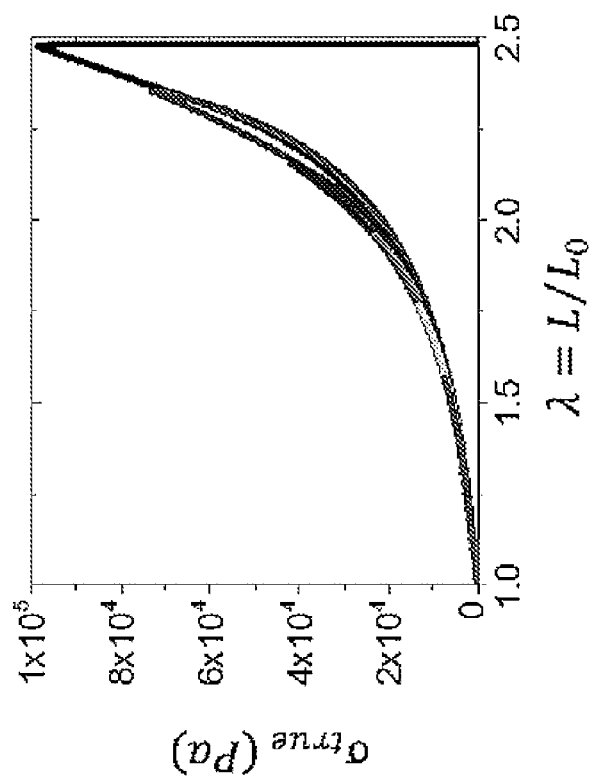
FIG. 10A shows representative cyclic loading-unloading curves for different elongations of sample M1200-4 (see FIG. 23).

Referring to FIG. 9, strain rate dependence on mechanical properties for M300-4 (FIG. 23) is shown. No strain-rate dependence was observed during the elastic phase of deformation ($\lambda<1.3$). In contrast, stress increases with the strain rate in the yielding regime ($\lambda<1.3$).

Referring to FIG. 10A and FIG. 10B, cyclic loading-unloading curves of M1200-4 (FIG. 23) were recorded for different $\lambda_{max}$ values: 1.6 (magenta), 1.75 (cyan), 1.9 (green), 2.15 (blue), and 2.35 (red). Stress-strain curves reveal the emergence of a hysteresis approximately halfway before rupture at $\lambda \cong 1.8$ (FIG. 10A). Hysteresis energy as a function of elongation is shown in FIG. 10B (inset: hysteresis normalized to the area under the corresponding stress-strain curve).

Figures 3A, 3B:
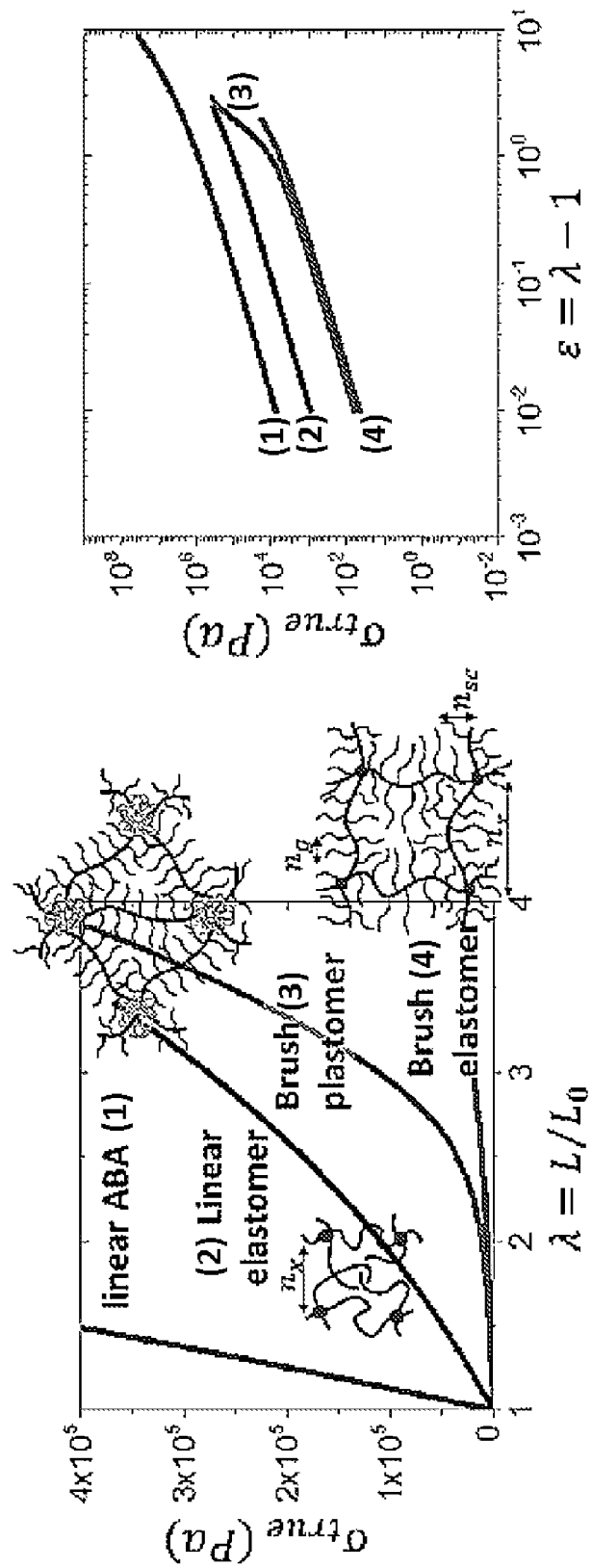
FIG. 3A and FIG. 3B show representative stress-strain curves of PDMS linear-chain elastomer, PMCL-PLLA-PMCL thermoplastic elastomer, brush-like elastomer, and a thermoplastic brush elastomer (M900-2).

Referring to FIG. 3A, FIG. 3B, and Table 3, stress-strain curves of PDMS linear-chain elastomer (black), PMCL-PLLA-PMCL thermoplastic elastomer (blue), brush-like elastomer (red), (Vantankhah-Vamosfaderani et al. (2017) *Adv. Mater.* 29: 1604209) and a thermoplastic brush elastomer (MP900-2) (green) are shown. Even though both brush-like networks show similar Young's modulus at small deformations, the plastomer sample demonstrates a much stronger strain-stiffening with deformation due to larger value of the strand extensibility ratio $\beta$.

c. S4 X-Ray Studies

Ultra-small-angle X-ray scattering (USAXS) measurements were carried out at the ID02 beamline of the ESRF (Grenoble, France). The measurements were conducted in transmission geometry using a photon energy of 12.46 keV. The monochromatic incident X-ray beam was collimated to a footprint of 100×200 μm² (V×H) on the sample. The total photon flux on the sample is estimated to $9.10^{11}$ photons per second allowing for single frame acquisition times less than 100 ms per frame. The accessed q values, with $q=4\pi\sin(\beta)\lambda$, cover a range from $7.5\times10^{-3}$ nm$^{-1}$ to 3 nm$^{-1}$ using 2 different sample-to-detector distances of 2.5 and 10 m. A Rayonix MX170HS implemented in a 35 m long vacuum flight tube was applied for recording of SAXS and USAXS intensities. For optimization of the signal with respect to signal noise ratio a binning of 2×2 pixel was applied leading to an effective pixel size of 89 μm in both directions. The recorded 2D data were calibrated and regrouped using the SAXS utilities platform (Sztucki and Narayanan (2007) *J. Appl. Cryst.* 40: S459). The analysis of the SAXS and USAXS data was performed using the SANS & USANS data reduction and analysis package provided by NIST (Kline (2006) *J. Appl/Cryst.* 39: 859-900) for the IgorPro environment from WaveMetrics.

The plastomer dimensions and spacing from USAXS measurements are shown in Table 5 below.

TABLE 5

| Sample | $n_{bb}$ | $n_A$ | $\phi_A$ | $d_3$ (nm) [1] | $d_2$ (nm) [2] | $d_1$ (nm) [3] | Q [4] | A (nm²) [5] |
|---|---|---|---|---|---|---|---|---|
| M600-3 | 602 | 677 | 0.16 | 74.4 | 45.6 | 3.42 | 703 | 9.3 |
| M1200-3 | 1065 | 810 | 0.10 | 77.4 | 45.8 | 3.36 | 561 | 11.7 |
| M1500-3 | 1483 | 867 | 0.09 | 86.3 | 50.4 | 3.40 | 622 | 12.8 |
| M1800-3 | 1765 | 780 | 0.07 | 123.2 | 63.4 | 3.44 | 1042 | 12.1 |
| M900-1 | 938 | 190 | 0.03 | 56.0 | 24.4 | 3.47 | 283 | 6.6 |
| M900-2 | 938 | 325 | 0.05 | 60.0 | 32.4 | 3.43 | 387 | 8.5 |
| M900-3 | 938 | 656 | 0.10 | 79.6 | 50.8 | 3.42 | 739 | 11.0 |
| M900-4 | 938 | 1235 | 0.18 | 140.0 | NA [6] | 3.43 | NA | NA |

[1] Position of the main interference peak. In the case of dense packing of spheres, it corresponds to the interdomain distance as $d_3/0.816$;
[2] Diameter of spherically-shaped A-domains;
[3] Distance between neighboring bottlebrush strands;
[4] Aggregation number, i.e., number of linear blocks in A-domains calculated as $Q = \pi d_2^3/(6n_A v_A)$, where $v_A = 0.141$ nm³ is MMA monomer volume;
[5] Interfacial area per bottlebrush strand calculated as $A = \pi d_2^2/Q$;
[6] The morphology switches to cylindrical shape.

Figure 16A:
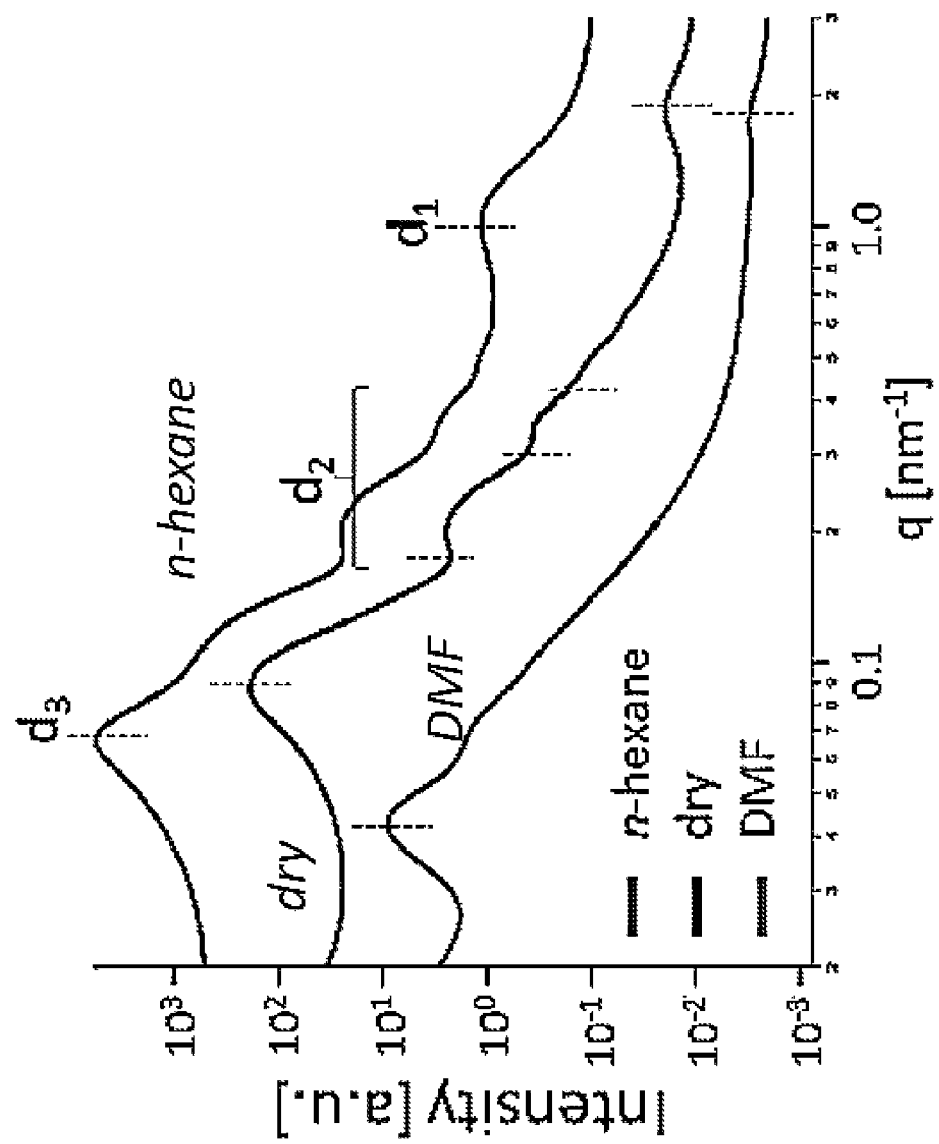
FIG. 16A shows a representative USAXS spectra of M300-4 sample dry, swollen in hexane, and swollen in DMF.

Referring to FIG. 16A, USAXS spectra of M300-4 swollen in n-hexane and DMF—selective solvents for PDMS and PMMA, respectively, are shown.

Figure 16B:
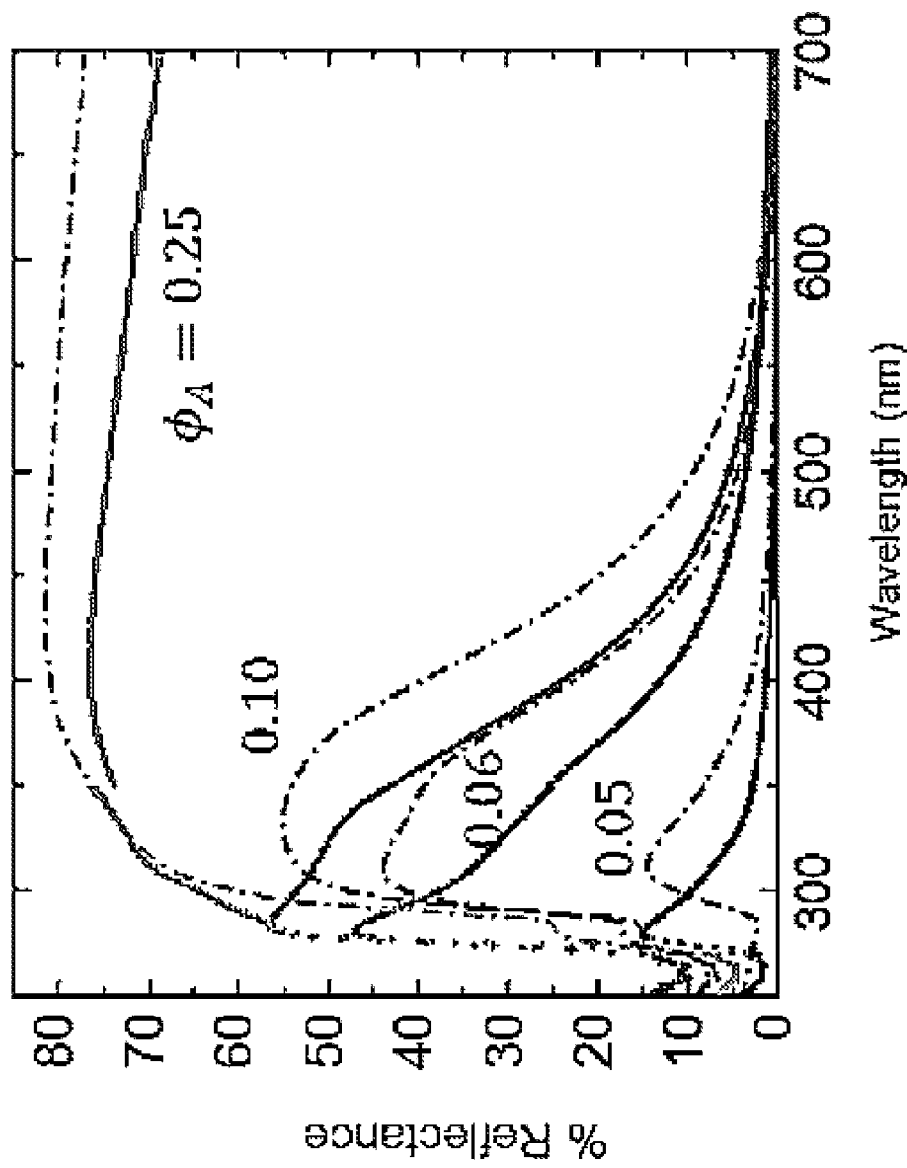
FIG. 16B shows a representative reflectance spectra of PBzMA-PDMS-PBzMA in a dry state (solid lines) and swollen in PDMS macromonomer (dashed lines).

Referring to FIG. 16B, reflectance spectra of PBzMA-PDMS-PBzMA in a dry state (solid lines) and swollen in PDMS macromonomer (dashed lines) are shown. Films of PBzMA-PDMS-PBzMA elastomer were prepared by casting from a toluene solution to a Teflon petri-dishes (Welch Fluorocarbon) followed by drying in the fume hood for 3 days. A small piece of the film was cut and placed onto a glass slide for optical measurements. Reflectance was measured by Carry5000 UV-Vis-NIR with Agilent diffuse reflectance accessory instrument, using Labsphere Spectralon as standard.

f. Mechanical Properties of Various Biological Tissues

Figure 1A:
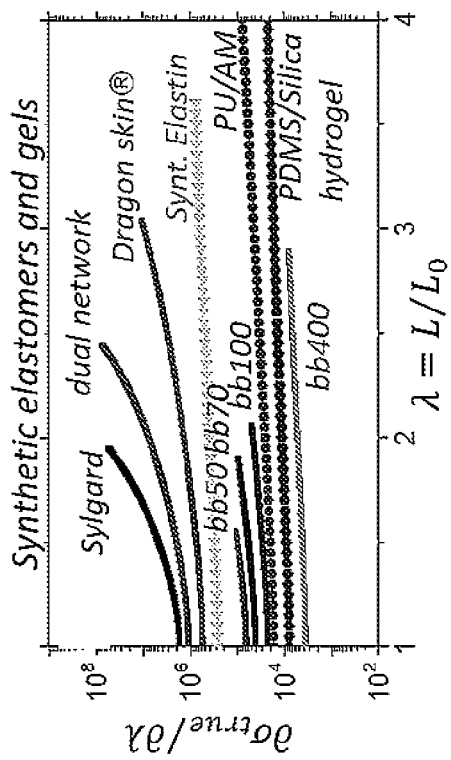

Table 6 displays fitting parameters E and P from stress-strain curves of assorted synthetic materials in FIG. 1A. Table 7 displays fitting parameters E and 3 from stress-strain curves of various biological tissues used for comparison to plastomers in FIG. 1B and FIG. 13. All curves were digitized, converted to true tensile stress vs elongation and fit following plastomer fitting procedures.

TABLE 3

| Sample | E (kPa) | β | $E_0$ (kPa) |
|---|---|---|---|
| PMCL-PLLA-PMCL ($\varphi_{PLLA} = 0.08$) | 768.5 | 0.0008 | 776.8 |
| Linear PDMS elastomer | 91.2 | 0.012 | 92.7 |
| Bottlebrush plastomer (900-2) | 4.0 | 0.258 | 6.2 |
| Bottlebrush elastomer ($n_x = 400$) | 4.0 | 0.094 | 4.6 |

TABLE 4

| | E (kPa) | β | $E_0$ (kPa) |
|---|---|---|---|
| PMMA-PBD-PMMA | | | |
| 6-80-60 | 1099.5 | 0.008 | 1110.6 |
| 14-80-14 | 2396.1 | 0.013 | 2438.7 |
| 20-80-20 | 5220.0 | 0.013 | 5310.0 |
| PMCL-PLLA-PMCL | | | |
| $\Phi_{PLLA} = 0.28$ | 3000.0 | 0.026 | 3108.3 |
| $\Phi_{PLLA} = 0.17$ | 1573.5 | 0.017 | 1610.1 |
| $\Phi_{PLLA} = 0.08$ | 768.6 | 0.008 | 776.7 |

TABLE 6

| Tissue Sample | E (kPa) | β | $E_0$ (kPa) | $\lambda_{max}$ | Ref |
|---|---|---|---|---|---|
| Sylgard ® 184 | 1273 | 0.46 | 3335 | 1.8 | 39 |
| Dual Network | 564 | 0.34 | 1054 | 2.4 | 40 |
| Dragon Skin ® | 443 | 0.18 | 586 | 3.0 | 41 |
| Synthetic Elastin | 263 | 0.02 | 271 | 3.6 | 42 |
| PDMS Bottlebrush [(1)] | 40.5 | 0.28 | 65.6 | 1.5 | 5 |
| PDMS Bottlebrush [(2)] | 30.0 | 0.23 | 43.7 | 1.9 | 5 |
| PDMS Bottlebrush [(3)] | 18.6 | 0.17 | 24.2 | 2.1 | 5 |
| PDMS Bottlebrush [(4)] | 3.3 | 0.08 | 3.7 | 3.5 | 5 |
| Polyurethane/acrylamide | 16.5 | 0.04 | 17.3 | 5.3 | 43 |
| PDMA/Silica Hydrogel | 8.09 | 0.006 | 8.2 | 10.4 | 44 |

PDMS bottlebrush elastomers with different degrees of polymerization of the backbone in the network strands: [(1)] $n_x = 50$; [(2)] $n_x = 70$; [(3)] $n_x = 100$; [(4)] $n_x = 400$.

TABLE 7

| Tissue Sample | E (kPa) | β | $E_0$ (kPa) | $\lambda_{fit}$ | $\lambda_{max}$ | Ref |
|---|---|---|---|---|---|---|
| Chicken Gut | 3.4 | 0.29 | 5.6 | 2.75 | 3.14 | 45 |
| Procine Aorta | 19.8 | 0.67 | 127 | 1.35 | 1.65 | 46 |
| Dog Lung | 0.3 | 0.69 | 1.8 | 1.40 | 1.96 | 47 |
| Brain | 0.06 | 0.75 | 2.0 | 1.20 | 1.45 | 48 |
| Blood Vessel | 3.4 | 0.75 | 40.0 | 1.30 | 1.50 | 49 |
| Fetal Membrane | 1.3 | 0.79 | 19.8 | 1.39 | 1.64 | 50 |
| Back Skin | 36.1 | 0.90 | 2417 | 1.23 | 1.72 | 51 |
| Lens Capsule | 10.8 | 0.90 | 722 | 1.22 | 1.72 | 52 |
| Heart Muscle | 0.02 | 0.96 | 6.3 | 1.13 | 1.19 | 53 |
| Human back skin | 36.1 | 0.90 | 2417 | 1.23 | 1.7 | [51] |
| Human abdominal skin | 1.2 | 0.93 | 168 | 1.22 | 1.4 | 54 |
| Eel skin | 7.8 | 0.84 | 205 | 1.33 | 2.3 | 55 |
| Mice skin | 2.6 | 0.90 | 174 | 1.27 | 1.5 | 56 |
| Porcine parallel | 5.8 | 0.74 | 59.2 | 1.85 | 1.6 | 57 |
| Porcine perpendicular | 10.6 | 0.46 | 27.8 | 1.36 | 2.4 | [57] | g. Design of Solvent-Free, Super-Soft Chromogenic Elastomers

Figure 2A:
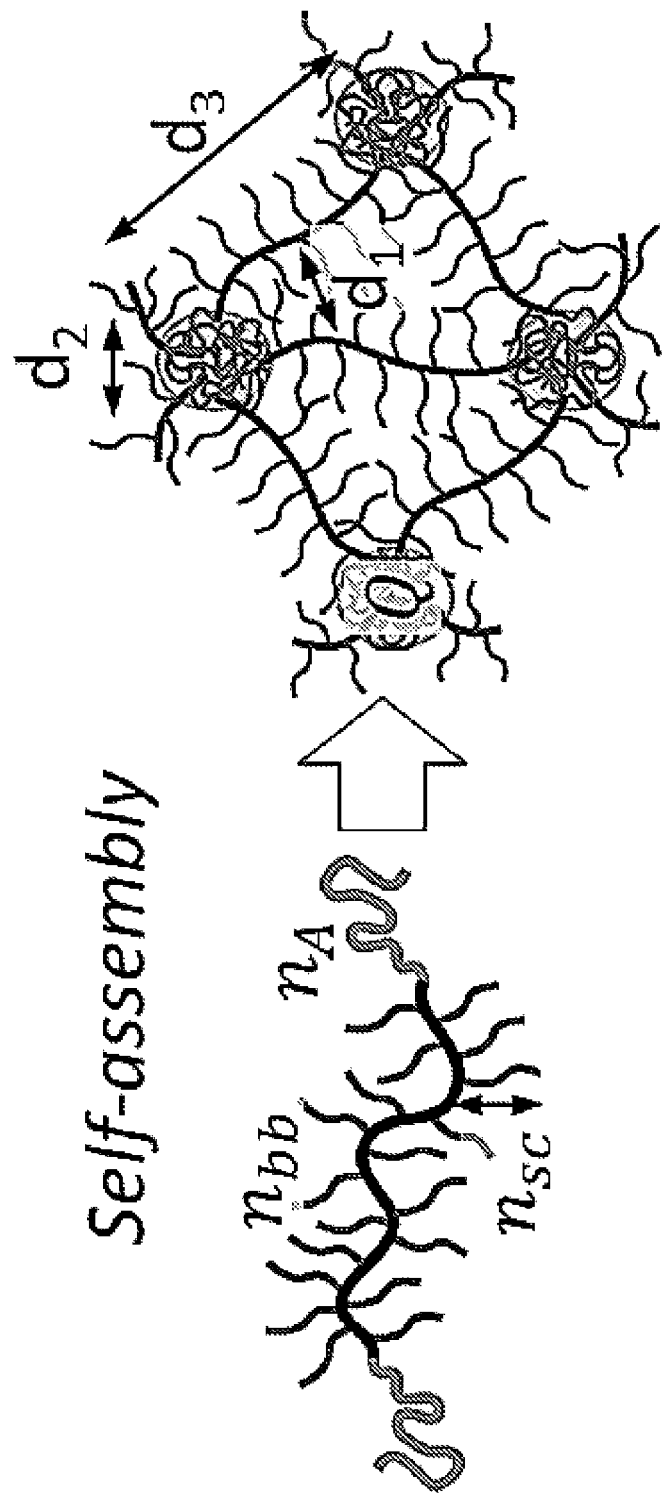
FIG. 2A shows the mechanism of network formation through self-assembly and microphase separation of ABA linear-brush-linear block copolymers.

Herein, the design of solvent-free, super-soft ($E_0 \sim 10^3$-$10^5$ Pa), strongly strain-stiffening ($E_c^{-1} \equiv \sigma_{true}/\equiv\lambda \sim 1$-$10^2$), chromogenic elastomers formed by microphase-separation of linear-bottlebrush-linear ABA triblock-copolymers is disclosed (FIG. 2A). Thus, the symbiosis of two blocks that are both chemically and physically distinct is explored: (i) flexible linear chains that aggregate into rigid domains and (ii) stiff bottlebrush strands that form a super-soft matrix. This interplay of rigid-while-flexible and soft-while-stiff, which is oxymoronic upon first glance, is actually representative of the unique potential of architectural control over materials' mechanical and optical properties. Elucidating how both building blocks not only play individual roles in this control, but also synergize with each other to enhance biomimetic performance is a central feature of this study. Specifically, it is shown that aggregation of linear blocks yields physical networks, while bottlebrush strands provide these networks with a low modulus. Further, the strong segregation of the chemically dissimilar blocks (So et al. (2014) Adv. Funct. Mater. 24: 7197-7204) augments the architectural pre-strain of the bottlebrush blocks (Sheiko et al. (2006) Nature 440: 191-194) and thereby significantly improves the networks' strain-stiffening characteristics (see FIG. 3A and FIG. 3B). This enables replication of the mechanical response of porcine skin and to achieve significant progress in replicating that of human skin as discussed below.

Referring to Figure FIG. 2A, the self-assembly of linear-bottlebrush-linear ABA triblock copolymers yields physical networks: A-domains of linear blocks embedded in a B-matrix of bottlebrush strands, where $n_A$, $n_{bb}$, $n_{sc}$ and are degrees of polymerization of the linear block, bottlebrush backbone, and bottlebrush side chains, respectively. The microphase separated structure is described by interbrush distance ($d_1$), diameter of the spherically-shaped PMMA domains ($d_2$), and interdomain distance ($d_3$).

Figure 14:
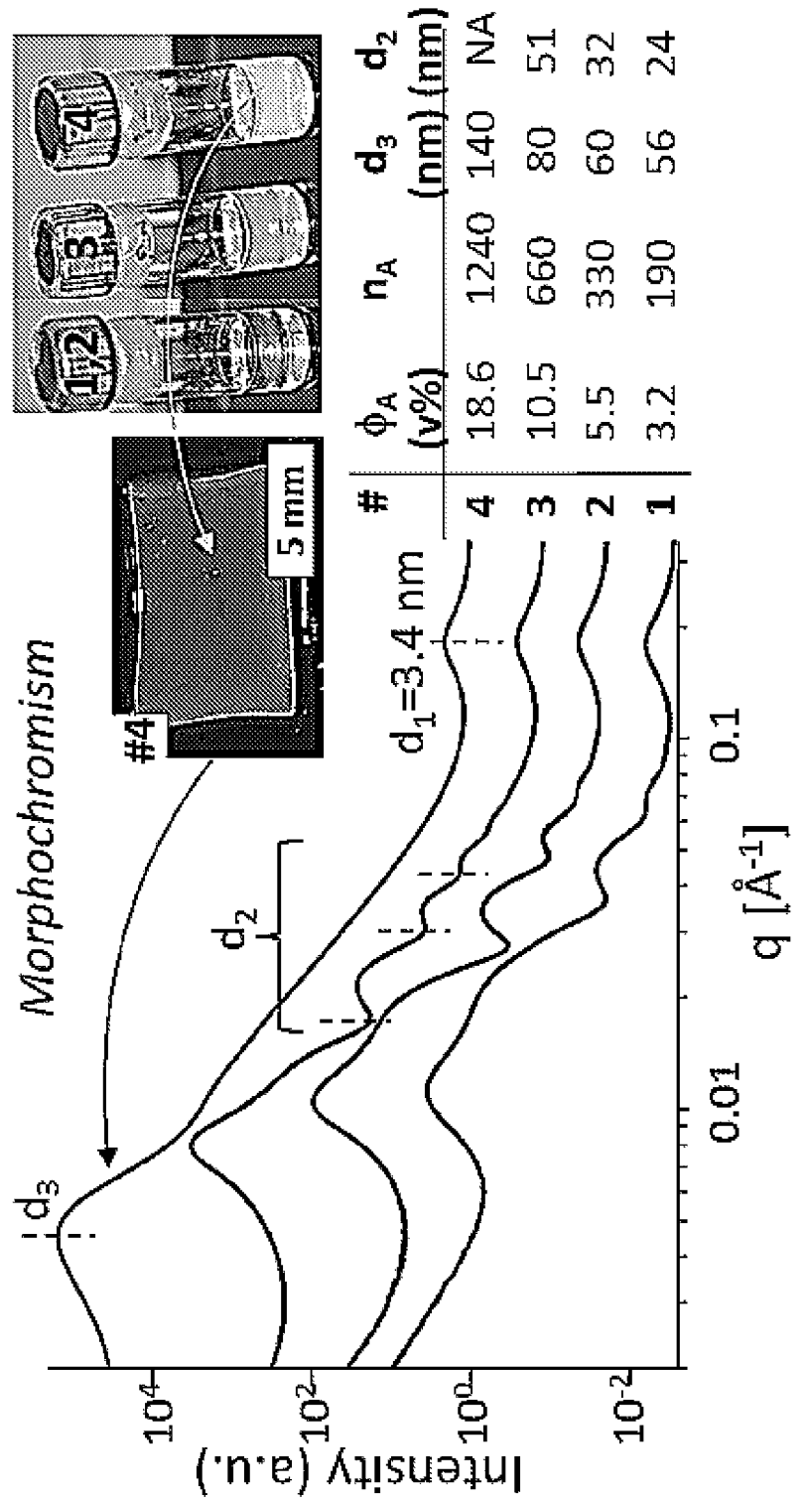
FIG. 14 shows representative data illustrating the structural coloration of plastomers.

To validate this concept, several series of linear-bottlebrush-linear ABA triblock-copolymers were synthesized with different degrees of polymerization (DP) of the bottlebrush backbone ($n_{bb} \approx 300$-$1800$) and identical DP of polydimethylsiloxane (PDMS) side chains ($n_{sc}=14$) (FIG. 17-19, FIG. 2A, and FIG. 23). Each series contains molecules with different DPs of linear A-block ($n_A \approx 30$-$1200$) corresponding to volume fractions $\phi_A=0.03$-$0.3$, where the A-block may be poly(methyl methacrylate) (PMMA), poly(benzyl methacrylate) (PBzMA), or poly(oligo(ethylene glycol) monomethyl ether methacrylate) (P(OEOMA)). For physical tests, thin films were prepared by solution casting. During solvent evaporation, microphase separation results in thermoplastic elastomers (plastomers) with characteristic coloration produced by constructive interference of light waves reflected by domain interfaces. Both color and mechanical properties depend on plastomer morphology, which was characterized by differential scanning calorimetry (DSC) and atomic force microscopy (AFM) (FIG. 2B and Table 2) and ultra-small-angle X-ray scattering (USAXS) (FIG. 14). This combination of techniques provided the interbrush distance ($d_1=3.4$ nm), domain diameter ($d_2=20$-$40$ nm), aggregation number ($0 \approx 300$-$100'$), and interdomain distance ($d_3=40$-$150$ nm) as summarized in Table 5 for different copolymer compositions.

Figure 2B:
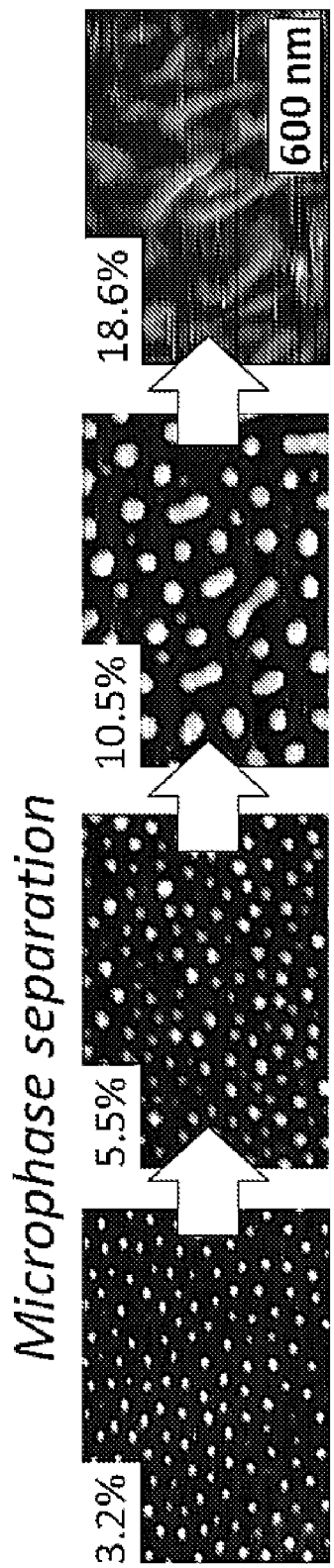
FIG. 2B shows AFM micrographs of the microphase-separated morphology for different ABA samples with different fraction of block A.

Referring to FIG. 2B, AFM height micrographs corroborate microphase separation of PMMA-bbPDMS-PMMA plastomers with identical $n_{bb}=938$ and varied linear PMMA DP with designated PMMA volume fraction $\phi_A$ (series M900-x in FIG. 23).

Referring to FIG. 14, USAXS patterns of the above plastomers display characteristic length scales as depicted in FIG. 2A and summarized in Table 5. Concentrated solutions (25 wt %) of the corresponding plastomers are also shown (top right). Evaporation of turquoise solution 4 (M900-4) yields a blue colored film.

Corresponding analysis revealed that plastomers' block dimensions ($n_{bb}$, $n_A$, $\phi_\lambda$) strongly impact their mechanical properties (FIG. 5A, FIG. 5B, and FIG. 6-34), which include (i) low initial modulus $E_0=4$-$50$ kPa (FIG. 23), (ii) intense strain-stiffening depicted as 10-100× increase of the differential modulus within a short strain interval (FIG. 5C and FIG. 5D), and (iii) the characteristic sigmoid shape of the $\equiv\sigma/\equiv\lambda$ curves that is strikingly similar to that of biological tissues. All of these features are a manifestation of a two-phase deformation process, which starts with extension of architecturally pre-strained bottlebrush network strands (elastic regime) followed by uncoiling of linear chains in A-domains (yielding regime). Unlike the elastic phase of deformation, yielding-phase stress depends on strain rate (FIG. 9) and develops small (<10%) hysteresis in loading-unloading cycles (FIG. 10A and FIG. 10B). All three features (reversibility, strain-rate dependence, and hysteresis) are also observed via yielding of collagen assemblies in biological tissues, which provides energy dissipation and additional extensibility (So et al. (2014) Adv. Funct. Mater. 24: 7197-7204; Yang, et al. (2014) Nature Comm. 6: 6649/1-10). Even though plastomers have completely different structure and distinct deformation mechanisms, they display a tissue-like mechanical response. While one may intuitively presume that the pre-strain of the B-blocks would impair network extensibility, uncoiling of the flexible A-blocks compensates for this inherent characteristic. In other words, the A-domains serve as reservoirs of untapped network extension and yield synergy that is muted in (i) all-linear ABAs, wherein the absence of pre-strain diminishes the phase-separation enhancement on strain-stiffening, and (ii) all-brush ABAs, wherein added architectural pre-strain impedes the overall extensibility of the material (So et al. (2014) *Adv. Funct. Mater.* 24: 7197-7204; Yang, et al. (2014) *Nature Comm.* 6: 6649/1-10; Jaspers et al. (2017) *Nature Comm.* 8: 15478; Ducrot et al. (2014) *Science* 344: 186-189).

Figure 5B:
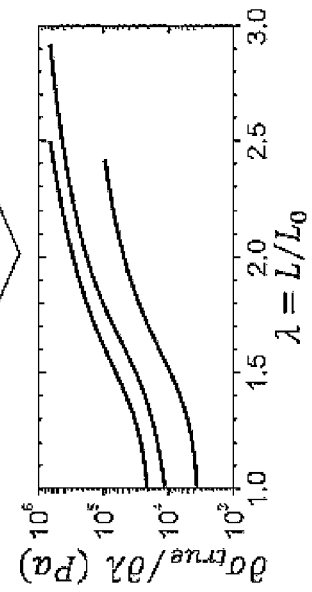
FIG. 5A-D show representative data illustrating the mechanical properties of plastomers as a function of block-copolymer composition.
Figure 5A:
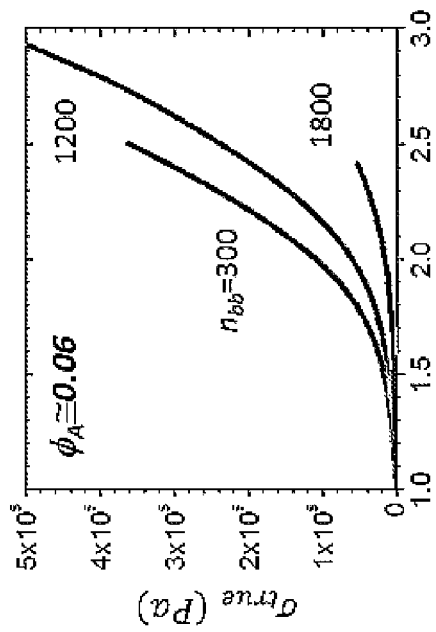

Referring to FIG. 5A, stress-strain curves of PMMA-bbPDMS-PMMA plastomers with identical $n_{bb}$=938 and varied A-block volume fractions ($\phi_A$) (series M900-x in FIG. 23) measured upon uniaxial extension in the elastic regime ($\lambda$=0.005 s$^{-1}$, T=25° C., FIG. 11A and FIG. 11B) are shown.

Referring to FIG. 5B, stress-strain curves of PMMA-bbPDMS-PMMA plastomers with different $n_{bb}$ but similar ($\phi_A \cong 0.0 \in$ are shown.

Figure 5D:
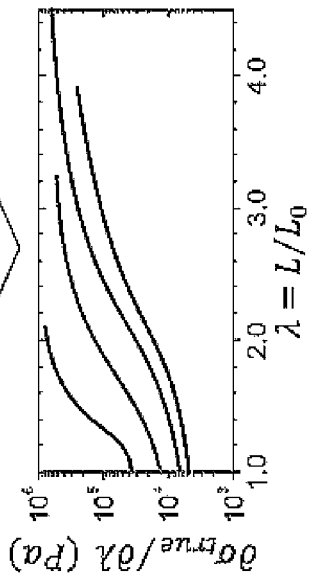
Figure 5C:
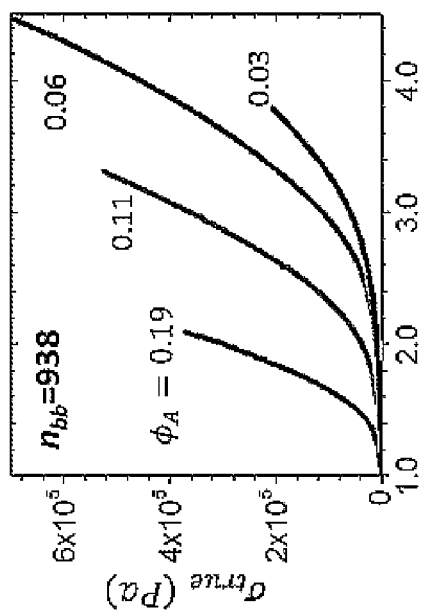
Figure 6A:
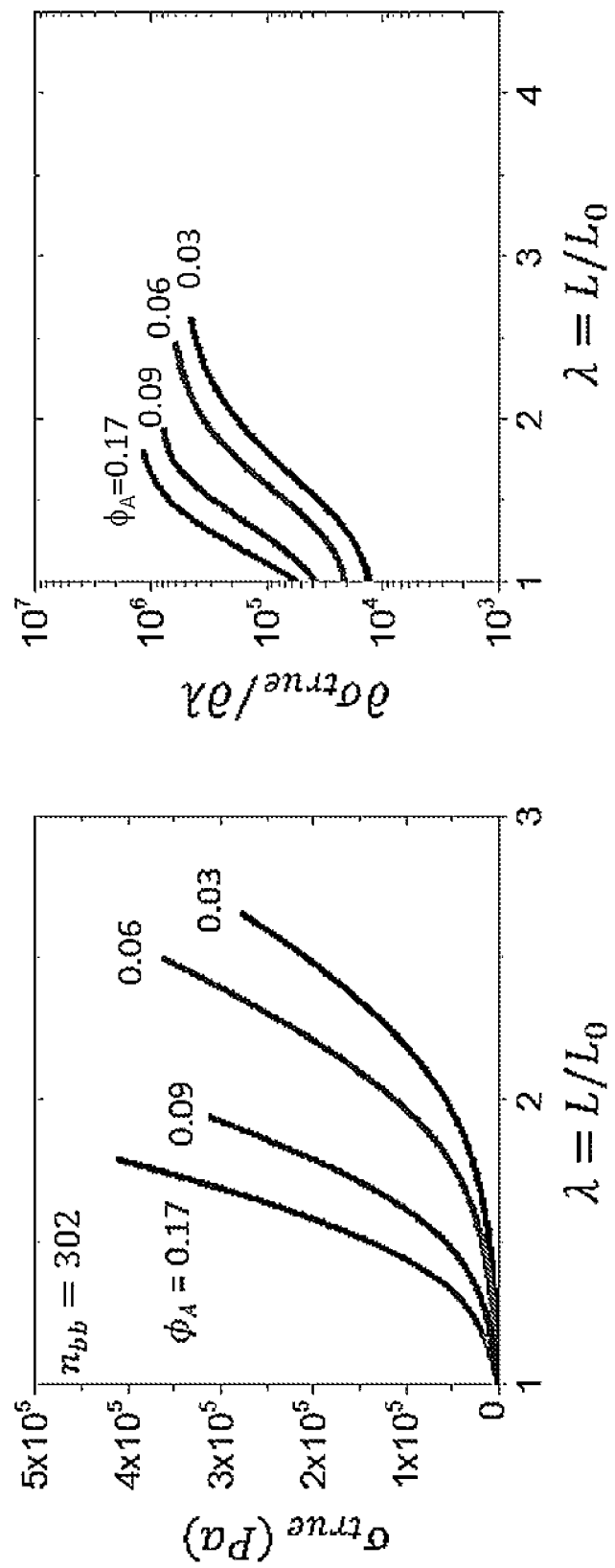
FIG. 6A-F show representative stress-strain curves (left) and the corresponding differential modulus curves (right) of multiple PMMA-bbPDMS-PMMA series with different degrees of polymerization of the PDMS bottlebrush backbone and volume fractions of PMMA linear chains as indicated (see FIG. 23).
Figure 6B:
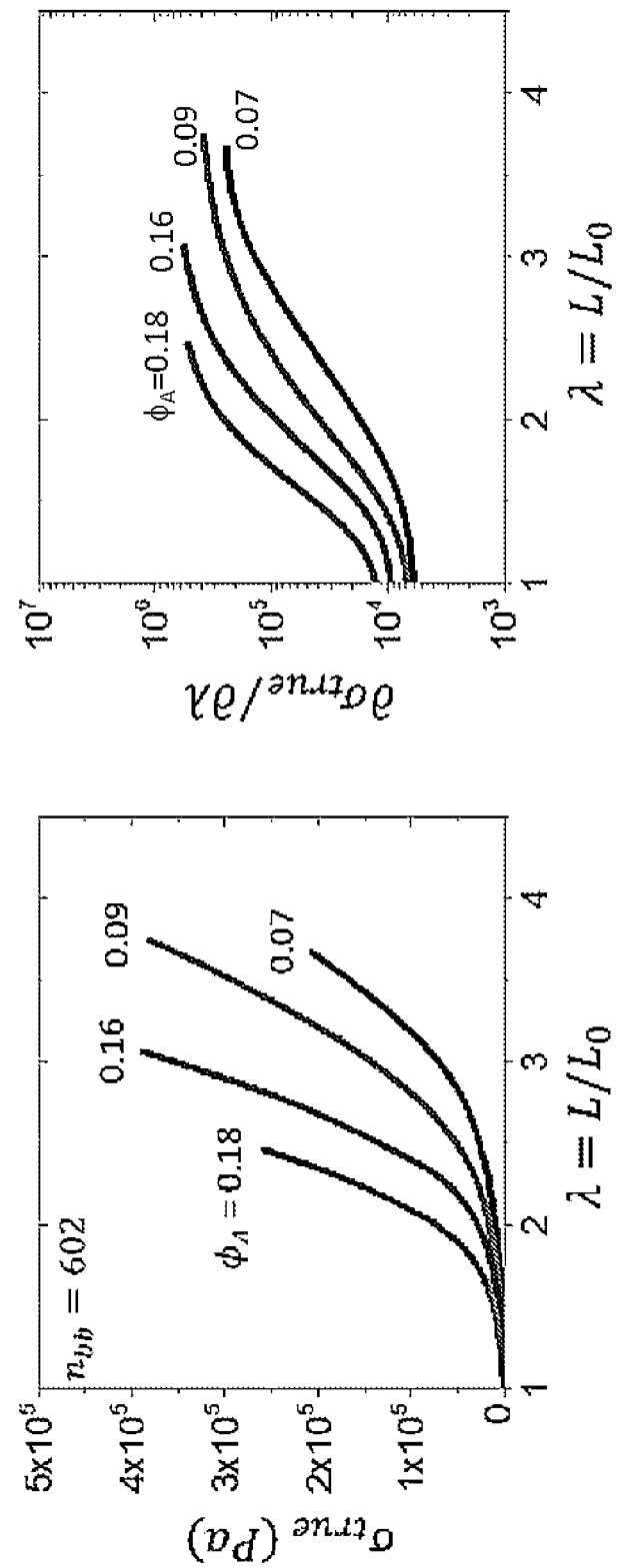
Figure 6C:
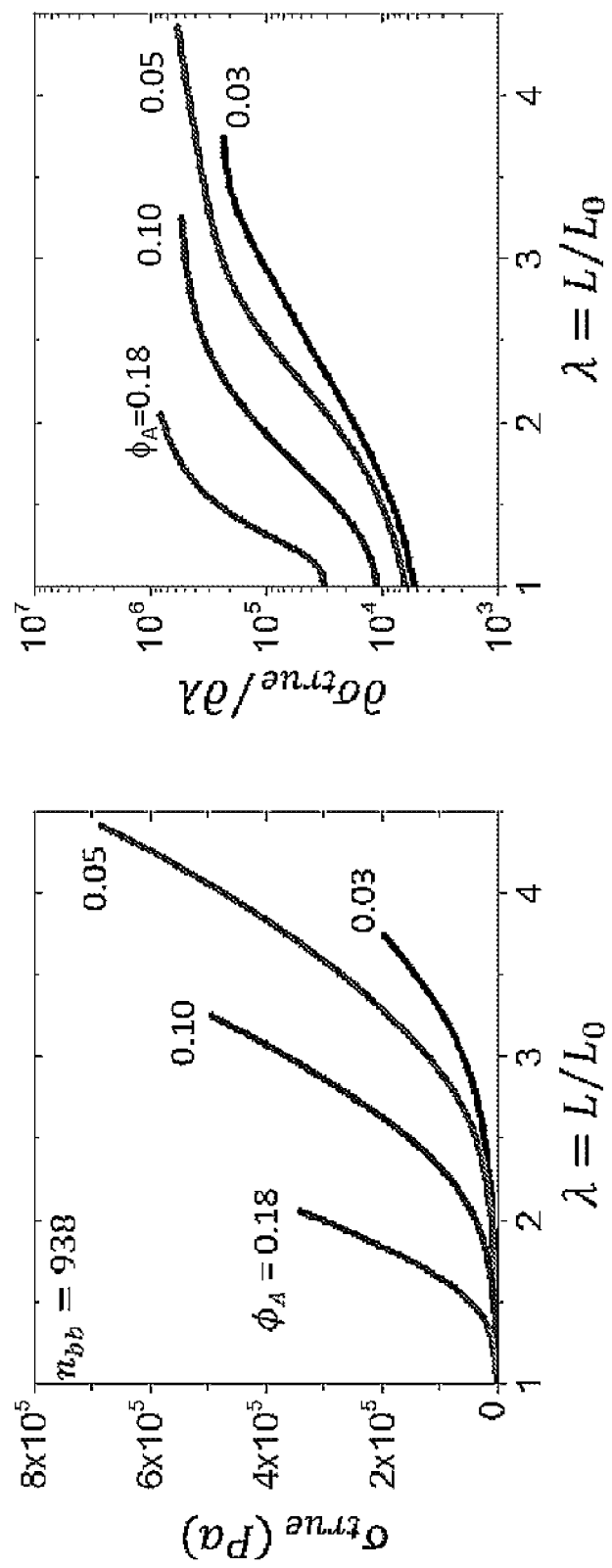
Figure 6D:
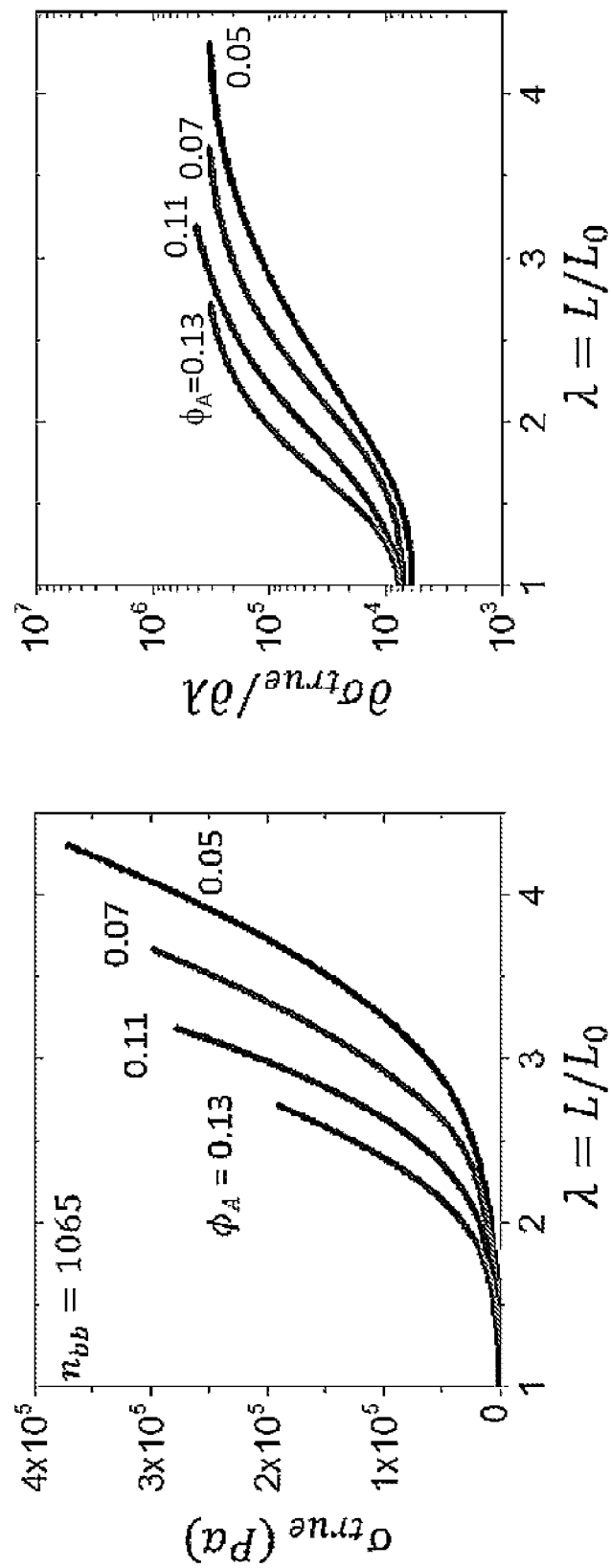
Figure 6E:
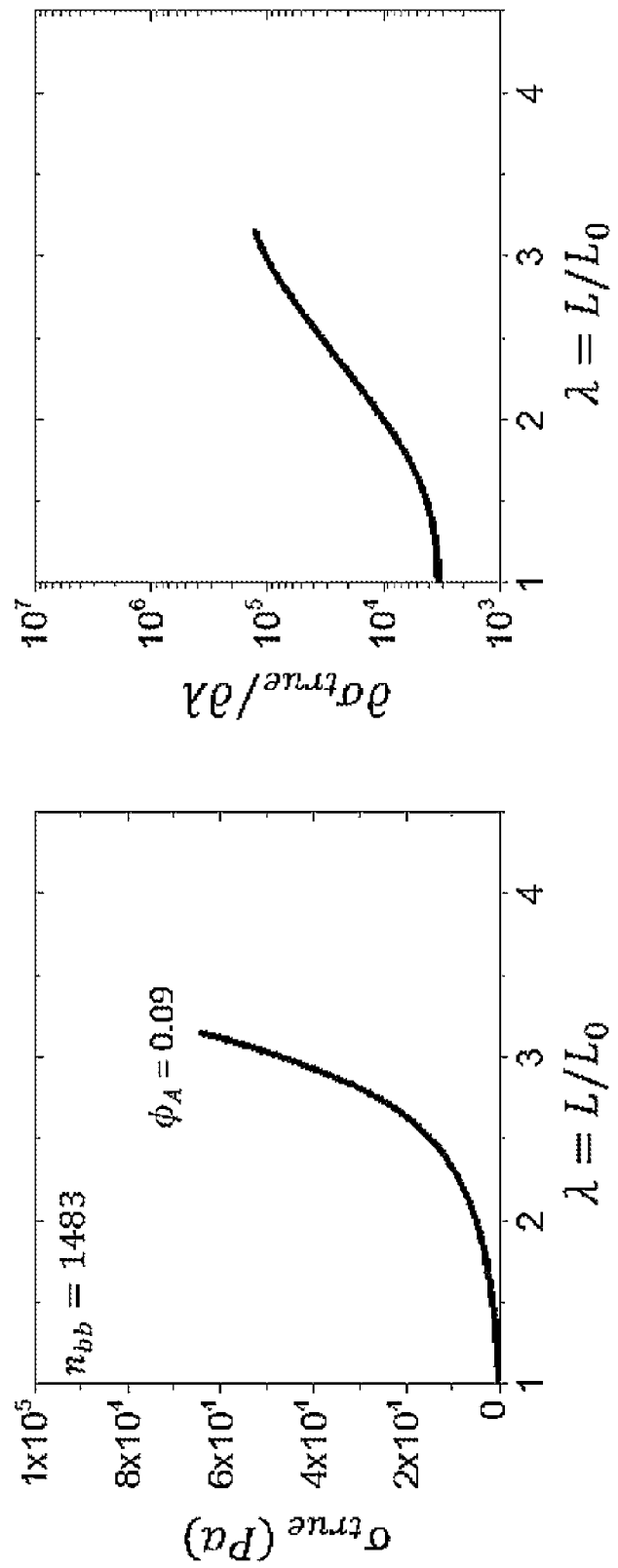
Figure 6F:
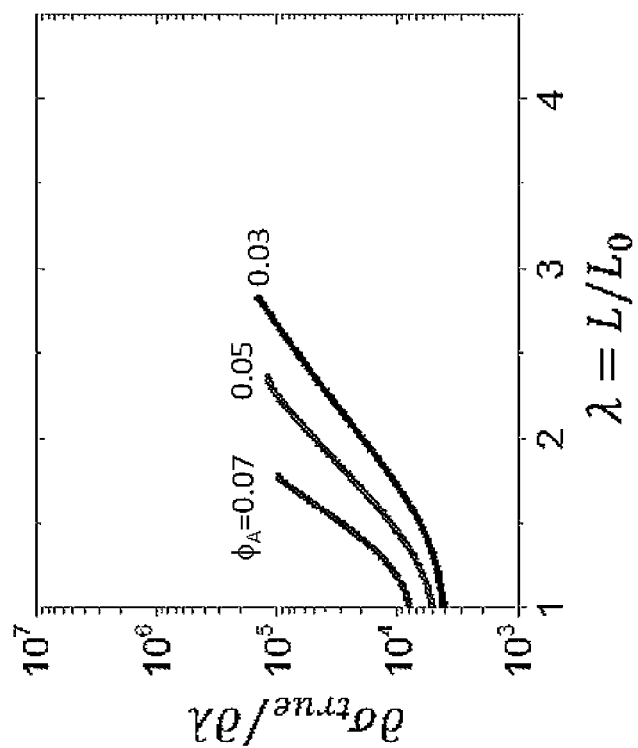
Figure 6F:
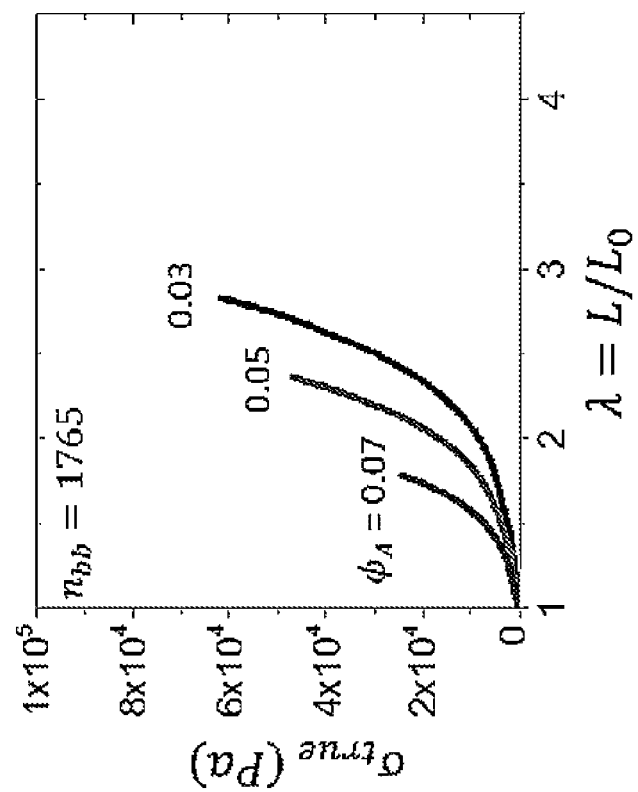

Referring to FIG. 5C and FIG. 5D, differential modulus of plots FIG. 5A and FIG. 5B, respectively, are shown.

For the elastic phase of deformation, the stress-strain curves were analyzed using a constitutive network deformation model (eq S6.18), which has been validated for various polymer networks, including biological gels (Vantankhah-Vamosfaderani et al. (2017) *Nature* 549: 497-501 (2017); Morin et al. (2012) *Science* 337: 828-832; Vantankhah-Varnosfaderani et al. (2017) *Adv. Mat.* 29: 1604209). This model is described by two parameters: (i) structural Young's modulus—a measure of crosslink density (eq S.6.22) and (ii) stain-stiffening parameter—a measure of strand extension as $\beta \cong (R_{in}^2)/R_{max}^2$, where $R_{max}$ is the contour length of a fully extended strand, ($R_{in}^2$) is the mean square end-to-end distance of strands in as-prepared elastomers (eq. S6.19). Parameter $\beta$ is controlled by finite extensibility of network strands with the lower and upper bounds corresponding to networks with coiled ($R_{in} \gg R_{max}, \beta \to 0$) and extended ($R_{in} \cong R_{max}, \beta \to 1$) strands, respectively. For comparison, typical linear-chain elastomers, including linear ABAs (Yu et al. (1996) *Macromolecules* 29: 6090-6099) are characterized by $\beta \cong 0.01$. Although bottlebrush covalent networks allow for a significant increase up to $\beta \cong 0.3$ (Table 6) (Vantankhah-Varnosfaderani et al. (2017) *Adv. Mat.* 29: 1604209), this is nonetheless notably lower than tissue's range of $\beta \cong 0.5$-0.9 (Table 7). Microphase separation in these plastomers results in additional strand extension with $\beta \cong 0.3$-0.8 (FIG. 23), which favorably overlaps with $\beta$=0.69 (lung), $\beta$=0.75 (brain), $\beta$=0.78 (skin), and $\beta$=0.75 (blood vessel) (Table 7).

To highlight the corresponding capacity for predictably controlling strain-stiffening, FIG. 23 summarizes the molecular and mechanical parameters of the studied plastomers. Indeed, the strain-stiffening parameter ($\beta$) follows the theoretically predicted scaling relation $\beta \sim n_A^{2/3} n_b^{-4/3}$ (FIG. 7A), which originates from chain extension $(R_{in}^2) \sim n_A^{2/3} n_{bb}^{2/3}$ (eqs S6.12, S6.17)-well-documented for block-copolymer systems in the strong segregation limit (Bates and Fredrickson (1990) *Annu. Rev. Phys. Chem.*, 41: 525-557). Similarly, the structural modulus follows $E \sim (1-\phi_A) n_A^{2/3} n_{bb}^{-4/3} \sim (1-\phi_A) \beta$ (FIG. 7B and FIG. 8), which originates from pre-stretching of the bottlebrush strands upon microphase separation (eq S6.22). The established structure-property correlations therefore allow for universal presentation of the differential modulus as a function of stress. The observed deviation of $\partial \sigma_{true}/\partial \lambda$ curves in the yielding regime occurs at different elongations due to the difference in finite extensibility of the various ABA network strand lengths (FIG. 5C and FIG. 5D). Since chain withdrawal proceeds at a constant force $(f \sim \sigma_{eng})$, the true stress in the yielding regime scales linearly with $\lambda$ as $\sigma_{true} \sim \lambda$.

In other words, the stress-strain behavior of different plastomers follow a universal trend that is architecturally controlled.

Figure 7B:
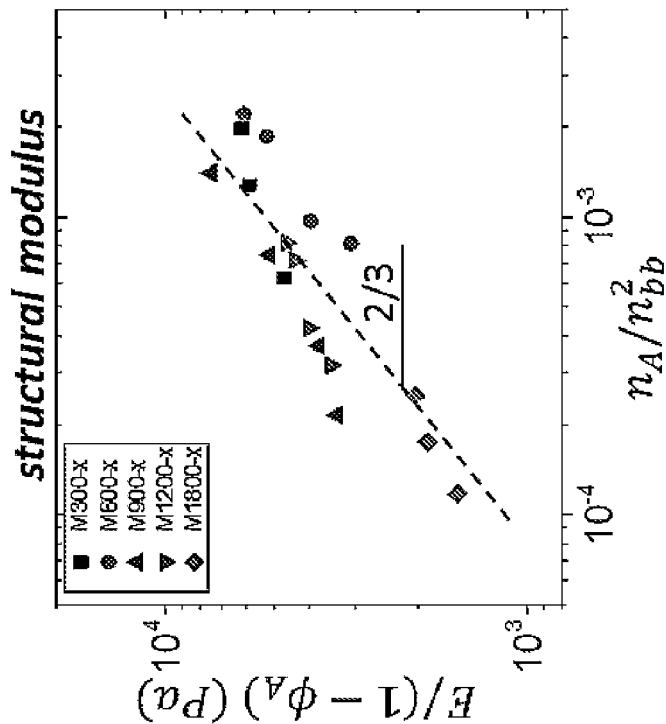
FIG. 7A and FIG. 7B show representative data illustrating the mechanical properties of plastomers as a function of block-copolymer composition.
Figure 7A:
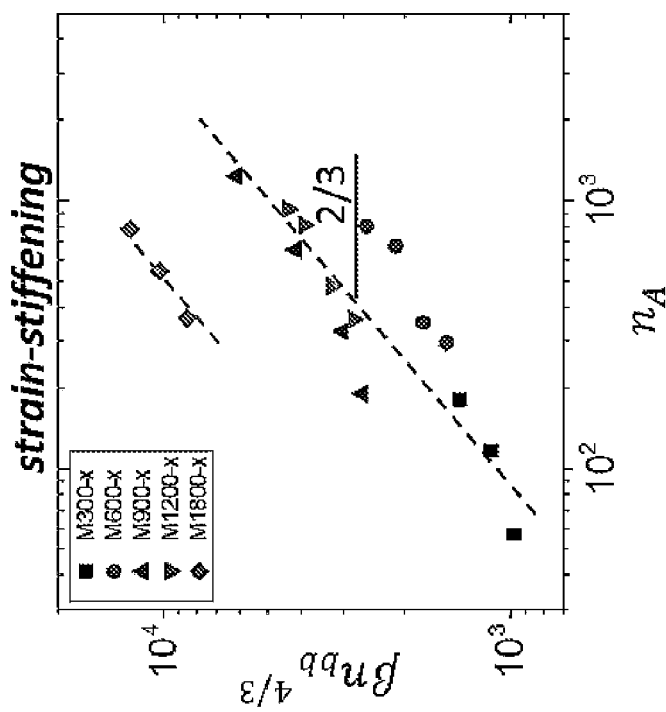
Figure 8:
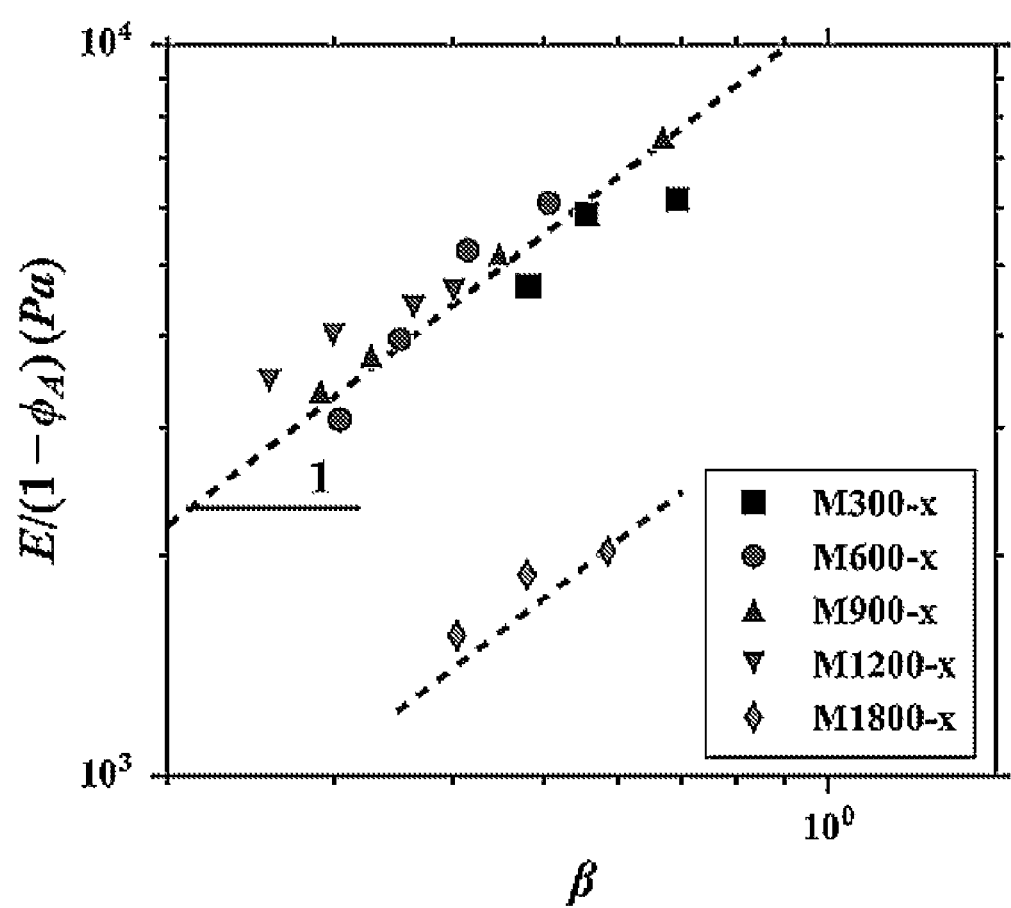
FIG. 8 shows a representative diagram illustration that the structural Young's modulus $E=3G$ increases linearly with the strand extension ratio $\beta$.

Referring to FIG. 7A, normalized strain-stiffening parameter #increases with DP of linear PMMA blocks as $\beta_n^{4/3}{}_{bb} \sim n^{2/3}{}_A$.

E and $\beta$ values are obtained by fitting stress-strain curves using eq S6.18 in the elastic phase of network deformation.

Referring to FIG. 7B, structural Young's modulus decreases with $n_{bb}$, and increases with $n_A$ as $E \sim n^{2/3}{}_A n^{-4/3}{}_{bb}$.

The data in E and F are mean with a standard deviation of 5-15% (FIG. 23).

Figure 13:
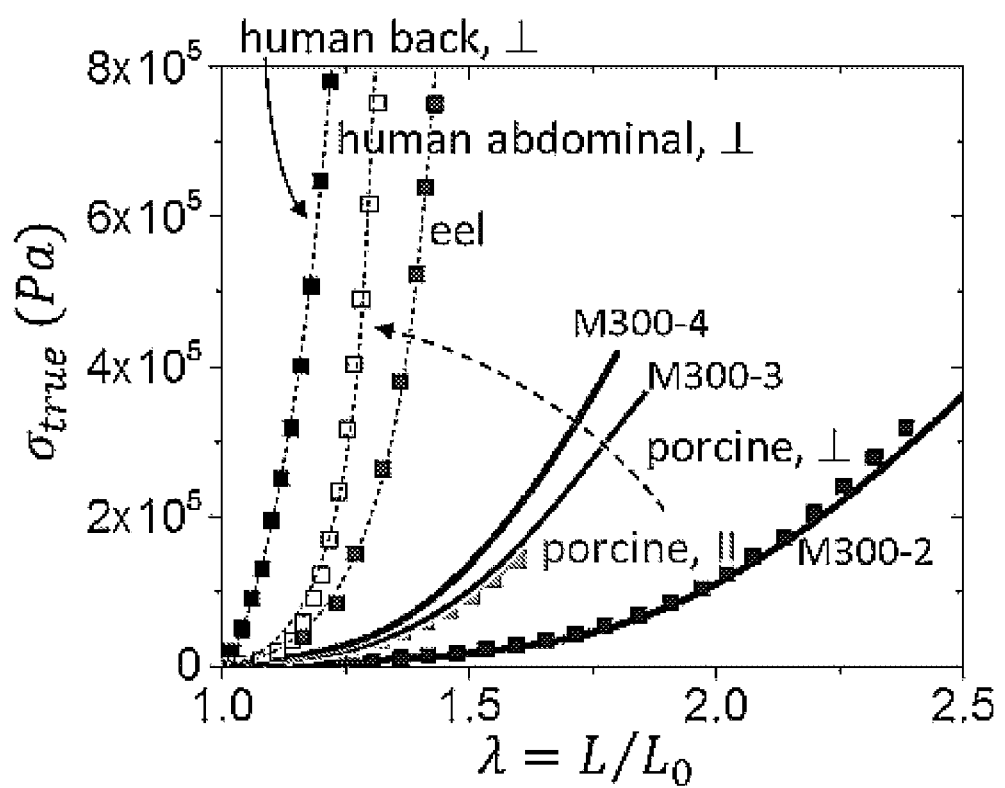
FIG. 13 show representative data illustrating the mimicking of skin tissue.
Figure 15B:
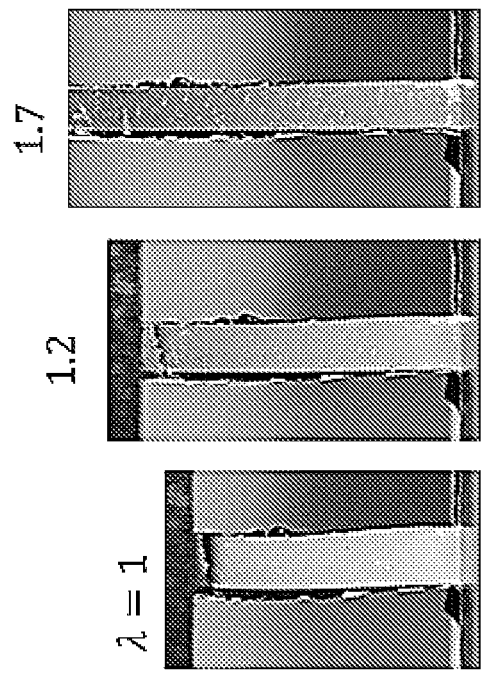
FIG. 15A-D show representative data illustrating structural coloration of as-prepared samples (A), upon deformation (B,C), and upon swelling (D).

Tensile stress-strain curves of assorted skin tissues exhibit, like those of plastomers, exhibit broad variation of mechanical properties defined by (i) low modulus E=0.4-12 kPa and significant strain-stiffening, with $\mu$=0.5-0.9 (FIG. 13 and Table 7). This parallel is exemplified by comparing the stress-strain curves of samples M300-2 and M300-3 to those of porcine skin measured perpendicular and parallel to the spine, respectively. The precise overlap thereof demonstrates that plastomers can replicate the deformation response of certain strain-stiffening tissues completely and precisely. Furthermore, elongation results in a blue shift of sample color (FIG. 15A) due to the corresponding decrease of interdomain distance ($d_3$) (FIG. 15B). This deformation does not affect domain size ($d_2$) and underlines the robust nature of the physical network. Similarly, solvent swelling results in omni-directional expansion between domains with an observed red-shift in color, which is consistent with USAXS (FIG. 16A) and reflectance measurements of plastomers in selective solvents (FIG. 16B). Inhomogeneous swelling (or drying) thus demonstrates spectacular visuals that resemble the optical complexity of natural systems like Earth and blue poison dart frogs (FIG. 15C). This also highlights how the same network structure that lends plastomers their mechanical characteristics also imbues them with adaptive structural coloration.

Referring to FIG. 13, true stress-elongation curves of assorted skin tissues (human back, human abdominal, eel, and porcine in Table 7) (dots) and M300-x plastomers cast from tetrahydrofuran with identical $n_{bb}$=302 and varied DP of linear PMMA block (lines) are shown. Current progress towards mimicking human skin is highlighted by the dashed arrow.

Figure 15A:
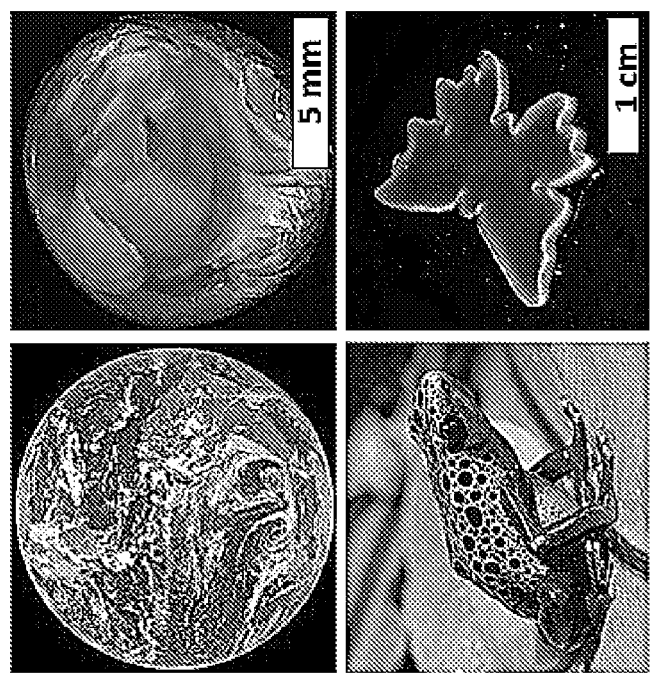
Figure 15D:
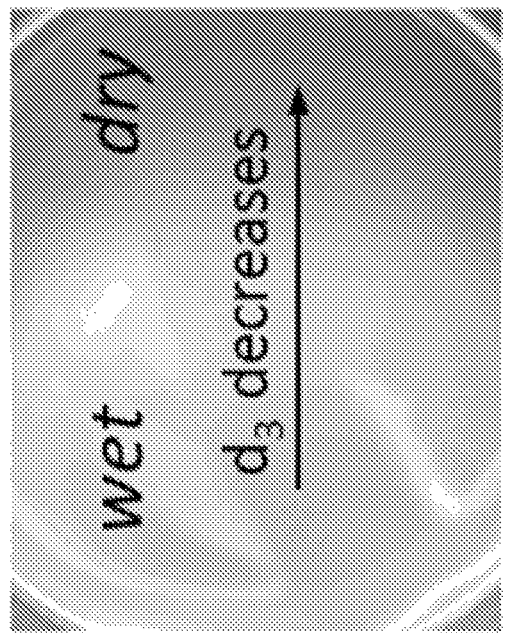
Figure 15C:
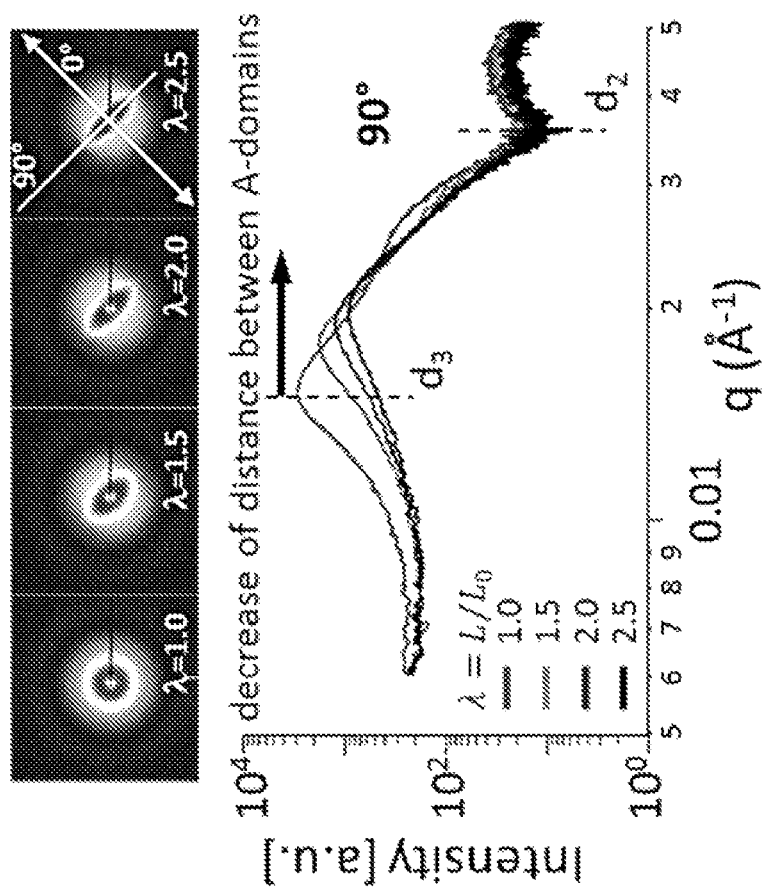

Referring to FIG. 15A, 2D USAXS patterns corresponding to different extension ratios exemplified for M300-2 is shown. Sections of the USAXS patterns are measured perpendicular (90°) to stretching direction at different elongation ratios. Elongation shifts the main interference maximum, which suggests a shortening between a PMMA domain's nearest neighbors ($d_3$ in FIG. 2A). Deformation has no effect on A-domain form-factor ($d_2$).

Referring to FIG. 15B, an observed color alteration from turquoise to dark blue during uniaxial stretching of a 2 mm thick (G900-1) P(OEOMA)-bbPDMS-P(OEOMA) film is shown.

Referring to FIG. 15C, top panel, a satellite image of Earth (left) and a drop of P(OEOMA)-bbPDMS-P(OEOMA) solution in toluene during drying (right) are shown. Referring to FIG. 15C, bottom panel, a blue poison dart frog (left) and a thin butterfly cutout of a PBzMA-bbPDMS-PBzMA plastomer B1000-2 (FIG. 23) with edges swollen with linear PDMS for contrast on a glass substrate (right) are shown. The back side of the glass substrate was painted black to enhance reflectance.

In conclusion, it has been established that the self-assembly of linear-bottlebrush-linear triblock copolymers (plastomers) empowers the integration of strain-adaptive stiffening and strain-induced coloration. It was further demonstrated that this class of materials enables the replication of the mechanical response of strongly strain-stiffening tissues, using porcine skin as an example and showing that human skin is within reach.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A copolymer block comprising a first linear polymer block, a brush-like polymer block, and a second linear polymer block, wherein the brush-like polymer block is positioned between the first and second linear polymer blocks, and wherein each linear block is amorphous.

2. The copolymer block of claim 1, wherein each linear block is either a methacrylate derivative, an acrylate derivative, a styrene derivative, or a norbornene derivative.

3. The copolymer block of claim 1, wherein each linear block is independently selected from poly(methyl methacrylate), poly(benzyl methacrylate), polystyrene, poly(vinyl acetate), polycarbonate, and poly(oligo(ethylene glycol) monomethyl ether methacrylate).

4. The copolymer block of claim 1, wherein the brush-like polymer block comprises the reaction product of:

a) a first monomer having a structure represented by a formula:

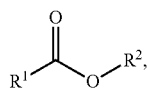

wherein $R^1$ is a structure represented by a formula selected from:

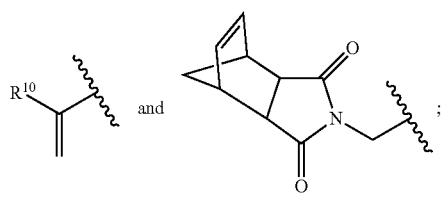

wherein $R^{10}$, when present, is selected from hydrogen and methyl;

wherein $R^2$ is a first linear polymer residue; and b) a diluent monomer.

5. The copolymer block of claim 4, wherein the first linear polymer residue is a residue of a polymer selected from poly(butyl acrylate), poly(butyl methacrylate), poly(butyl norbornene), polystyrene, polydimethylsiloxane, and polyethylene glycol.

6. The copolymer block of claim 4, wherein the second linear polymer residue is a residue of a polymer selected from polydimethylsiloxane, polycaprolactone, and poly(butyl acrylate).

7. The copolymer block of claim 4, wherein the diluent monomer is selected from an alkyl acrylate monomer, a methacrylate monomer, and a norbornene monomer.

8. The copolymer block of claim 1, wherein the brush-like polymer block comprises at least one residue having a structure represented by a formula selected from:

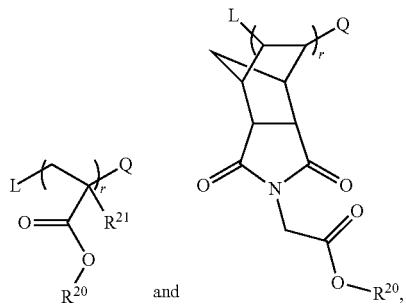

wherein r is an integer selected from 2 to 800;

wherein L is an active site of polymerization or a residue of a radical initiator;

wherein Q is an active site of polymerization or a residue of a radical initiator;

wherein each occurrence of $R^{20}$ is independently selected from a first linear polymer residue and a diluent monomer residue, provided that at least one occurrence of $R^{20}$ is a first linear polymer residue and at least one occurrence of $R^{20}$ is a diluent monomer residue; and wherein each occurrence of $R^{21}$, when present, is independently selected from hydrogen and methyl.

9. The copolymer block of claim 1, wherein the brush-like polymer block is a polydimethylsiloxane derivative.

10. The copolymer block of claim 1, wherein the copolymer block is a tri-block copolymer.

11. The copolymer block of claim 10, wherein the tri-block copolymer is represented by a formula A-B-A', wherein A is the first linear polymer block, B is the brush-like polymer block, and A' is the second linear polymer block.

12. A polymer network comprising a plurality of the copolymer blocks of claim 1.

13. The polymer network of claim 12, wherein the polymer network has been formed as a medical device.

14. The polymer network of claim 13, wherein the medical device is selected from an implant, a microneedle array, a wound dressing pad, a tissue adhesive, a tissue sealant, a dermal filler, a vascular graft, or a catheter.

15. The polymer network of claim 12, wherein the polymer network has been formed as a coating, a gasket, or an adhesive layer.

16. An article comprising the polymer network of claim 12.

* * * * *